(12) United States Patent
Parietti et al.

(10) Patent No.: US 11,198,845 B2
(45) Date of Patent: Dec. 14, 2021

(54) SYSTEM, METHOD, AND APPARATUS FACILITATING AUTOMATED MODULAR MANUFACTURE OF CELL THERAPY

(71) Applicant: Multiply Labs Inc., San Francisco, CA (US)

(72) Inventors: Federico Parietti, San Francisco, CA (US); Kameron C. Chan, San Francisco, CA (US); Alice Melocchi, Dalmine (IT); Jeffrey Ackerman Curhan, Warwick, RI (US); Michelle Chen, San Francisco, CA (US); Nolan Dickey, San Francisco, CA (US); Joaquin Giraldo-Laguna, San Francisco, CA (US); Roger Lo, San Francisco, CA (US); Lawrence Zachary Bright, Palo Alto, CA (US); Sam Ihns, Cambridge, MA (US); Umberto Scarfogliero, San Francisco, CA (US)

(73) Assignee: Multiply Labs Inc., San Francisco, CA (US)

( * ) Notice: Subject to any disclaimer, the term of this patent is extended or adjusted under 35 U.S.C. 154(b) by 0 days.

(21) Appl. No.: 17/234,753

(22) Filed: Apr. 19, 2021

(65) Prior Publication Data

US 2021/0324318 A1 Oct. 21, 2021

Related U.S. Application Data

(60) Provisional application No. 63/011,927, filed on Apr. 17, 2020.

(51) Int. Cl.
*C12M 3/00* (2006.01)
*C12M 1/34* (2006.01)

(52) U.S. Cl.
CPC .......... *C12M 23/42* (2013.01); *C12M 23/44* (2013.01); *C12M 41/40* (2013.01)

(58) Field of Classification Search
CPC ....... C12M 23/42; C12M 23/44; C12M 41/40
See application file for complete search history.

(56) References Cited

U.S. PATENT DOCUMENTS

| 5,096,676 A | * | 3/1992 | McPherson | C30B 7/00 117/206 |
| 5,738,825 A | * | 4/1998 | Rudigier | B01L 3/5085 422/425 |

(Continued)

FOREIGN PATENT DOCUMENTS

WO   WO 2008109880 A1   9/2008

OTHER PUBLICATIONS

International Search Report with Written Opinion corresponding to International Patent Application No. PCT/US21/18927, dated Jul. 14, 2021, 8 pages.

*Primary Examiner* — Shogo Sasaki
(74) *Attorney, Agent, or Firm* — Morgan, Lewis & Bockius LLP

(57) ABSTRACT

A rigid cartridge for housing and removably coupling with a soft body bioreactor is provided. The rigid cartridge includes rigid walls defining a rigid housing. The rigid walls expose a fixed interior configured to house the soft body. An interior surface of a first rigid wall includes a first mating mechanism to engage a second mating mechanism of the soft body to removably coupled with the rigid cartridge and accommodate the soft body in the fixed interior of the rigid cartridge. A rigid wall includes a planar upper surface including an aperture. Each aperture is encompassed by an annular hood protruding upwardly from the substantially planar upper surface and integrally formed with the at least one rigid wall. The aperture is configured to receive and (Continued)

fixed engage a corresponding connector. Each connector includes a rigid coupling mechanism that provides communication with a corresponding plurality of ports of the soft body.

13 Claims, 24 Drawing Sheets

(56) References Cited

U.S. PATENT DOCUMENTS

| | | | |
|---|---|---|---|
| 7,674,435 B2* | 3/2010 | Pastel | B01L 3/5085 |
| | | | 422/552 |
| 7,682,570 B2* | 3/2010 | Nishimura | C12M 23/12 |
| | | | 422/401 |
| 7,740,806 B2* | 6/2010 | Natarajan | B01J 19/0046 |
| | | | 422/404 |
| 7,776,609 B2* | 8/2010 | Pastel | G01N 35/00594 |
| | | | 436/165 |
| 7,901,643 B2* | 3/2011 | Shimizu | G01N 21/05 |
| | | | 422/417 |
| 10,688,493 B2* | 6/2020 | Kim | F04B 43/12 |
| 2003/0031829 A1* | 2/2003 | Tanner | C09J 5/00 |
| | | | 428/131 |
| 2005/0170498 A1* | 8/2005 | Dolley | B01L 3/5085 |
| | | | 435/288.4 |
| 2006/0141527 A1* | 6/2006 | Caracci | G01N 21/7743 |
| | | | 435/7.1 |
| 2006/0257956 A1 | 11/2006 | Basset et al. | |
| 2015/0322397 A1 | 11/2015 | Cornforth et al. | |

\* cited by examiner

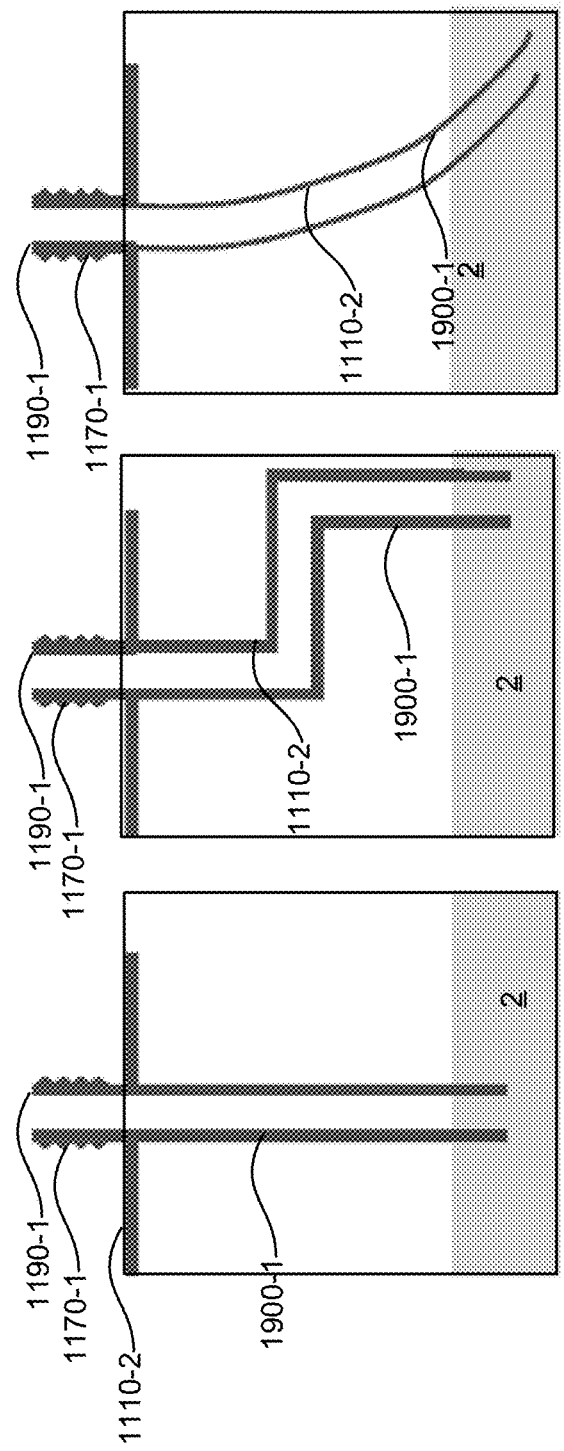

SYSTEM, METHOD, AND APPARATUS FACILITATING AUTOMATED MODULAR MANUFACTURE OF CELL THERAPY

CROSS-REFERENCE TO RELATED APPLICATION

This application claims priority to U.S. Provisional Patent Application No. 63/011,927, entitled "Modular Robotic System and Modular Closed-System Architecture for the Parallel, Automatic Manufacturing of Cell Therapies," filed Apr. 17, 2020, which is hereby incorporated by reference in its entirety for all purposes.

TECHNICAL FIELD

The present disclosure generally relates to systems and methods for facilitating modular and parallelized manufacturing at a biological foundry. More particularly, the present disclosure relates to systems and methods designed to facilitate implementing one or more workflows at a biological foundry.

BACKGROUND

Cell therapies are next-generation drugs where live cells are used to treat a subject. This is in contrast with traditional small-molecule and biologic drugs, where small or large molecules—but not whole living cells—are used to treat patients. Many of the most recent and promising innovations in medicine are represented by cell therapies in which the cells of a subject (either the patient or a donor) are extracted, genetically engineered in a lab, grown in an incubator, and finally infused in the patient in order to achieve a therapeutic effect. However, despite the life-saving effects of many cell therapies, there are significant bottlenecks to their widespread adoption. For instance, one obstacle is represented by the current limits in manufacturing capacity for cell therapies. Conventional cell therapy production processes are still largely labor-based and inefficient.

Traditionally, cell therapies are produced with labor-intensive processes. These conventional processes require not only a large number of manufacturing operators, but also the employment of highly skilled (and expensive) technicians. These constraints make it particularly difficult to manufacture cell therapies at an industrial scale. Cell therapy manufacturing processes are low-scale and labor-intensive because they were originally developed in the context of academic research. The original lab processes—which were developed to demonstrate the feasibility of cell therapies—were then hastily modified and retrofitted in order to fulfill regulatory requirements and achieve good manufacturing practices.

This conventional approach allowed drug manufacturers to bring to the market the first approved cell therapies. However, this labor-intensive, lab-oriented approach is unsuitable to achieve industrial scale. At their core, current cell manufacturing processes were designed to be manually completed by highly trained personnel—such as the researchers that conduct scientific experiments in an academic environment. Requiring this type of skillset becomes a disadvantage in an industrial setting. Cell manufacturing processes depend on highly trained, highly educated manual labor, and this makes them incompatible with the efficiency of mass-manufacturing industrial processes.

The dominant conventional approach to cell manufacturing is based on a set of separate individual pieces of manufacturing equipment placed on a clean room bench. This manufacturing process still looks exactly like a research laboratory, where all the machinery is manually operated and directly supervised by highly skilled operators. In order to execute the cell manufacturing processes, these skilled operators gown up, enter a clean room, and manually activate the machines. The operators also transfer the batch material from machine to machine, manually sample the batches to perform quality control testing, ensure that reagents are delivered to the cells, and ensure that waste material is removed. This labor-based conventional approach is very different from the organization of industrial-scale processes, where most tasks are autonomously executed by specialized machinery, which is supervised by ordinary manufacturing technicians (not engineers, nor scientists).

As such, the conventional labor-based approach to cell therapy manufacturing has at least three fundamental limits. First, the conventional approach is not scalable and not robust to operator variability. Because the conventional approach is extremely labor-intensive, cell therapy manufacturing is limited to small-scale applications. Increasing throughput beyond a few hundred products per year has proven extremely difficult, because such an effort would require hiring, training, retaining, and managing a large number of highly skilled, expensive operators. Moreover, labor-based processes are typically unable to reach industrial scale, and cell manufacturing is not an exception. This pronounced reliance of labor presents additional disadvantages, including the fact that—because of operator variability—the yield and the features of the finished cell therapy product are hard to predict and to control. This operator variability makes scaling the process of manufacturing cell therapy products even harder—particularly in terms of margins, in which a higher number of rejected batches increases the cost per batch.

Additionally, the conventional approach to manufacturing cell therapy products is inefficient. Since individual machines for the cell therapy manufacturing process are utilized in series (e.g., the machines are used one at a time, with a single batch manually moved from a piece of machinery to the next), when a machine is active all the others are idle. This results in a low utilization rate for all machines, since most of the machines are waiting for the batch to arrive, while a single machine is being used. The problem of a very low utilization rate is particularly evident for cell manufacturing processes, which are characterized by machines with markedly different cycle times. More specifically, systems like bioreactors process a single batch for weeks, while machines like thawing and freezing systems are only used for a few hours on a single batch. This results in utilization rates that are even lowed for the faster machines—because the slower machines are the bottleneck and limit the rate of the rest of the serial process.

Finally, the conventional approach to manufacturing cell therapy products has low throughput. Because the process is managed and executed by human operators, only one batch can be produced at any given time on a serial production line. For instance, if two batches were manufactured at the same time on the same production line, in fact, there would be high risk of cross-contamination or of mix-up errors by the operators. Since all the serial machines are used for just one product at a time, the resulting throughput of the production line is extremely low. As a reference, typically a cell therapy product takes two to three weeks to be manufactured. This means that, in order to avoid mix-ups, a whole production line must be reserved for a single product for about half of a month—a rate that is incompatible with industrial scale. Because of this temporal constraint, a whole manufacturing suite (typically consisting of about 1,000 square feet of clean room space) must be reserved for a single serial production line. Therefore, the only way to increase throughput via this conventional approach is by creating facilities with multiple independent suites that replicate the same process. However, each suite can only handle one product at a time, occupies significant clean room space, and is entirely operated by skilled labor. As such, this conventional approach is not scalable, and not suitable to manufacture more than a few hundreds of cell therapies per year—with very high production costs.

One solution to this conventional approach are closed system cell therapy machines that have been developed to attempt to address the shortcomings of the traditional approach. However, even this solution is still labor-intensive and inadequate to reach industrial scale. For instance, this solution can be described as an end-to-end serial system that is contained into a single machine. Different parts of the same machine perform the different steps of the production process. In other words, a single piece of equipment contains all the sub-systems that are needed to perform the cell manufacturing process. An intricate set of tubes connects all of these systems, so that the cell therapy product (which is typically in liquid form) can be transferred from one subsystem to the next without being exposed to the external environment, which provides the closed system.

However, these end-to-end, closed systems are sold as a unique piece of machinery. As such, the machinery cannot be modified by the buyer: once a system is bought, the buyer is constrained to run the exact process for which that machine was designed. Additionally, the machinery still needs to be operated by a highly skilled technician, who needs to perform a complicated set of actions to set up, monitor, and manage the manufacturing process. More specifically, highly trained operators set up the intricate network of tubes that is required by each batch. These operators are also tasked with opening and closing the valves that regulate the flow of material from one part of the system to the next. Furthermore, technicians also manually sample the batch, whenever testing is needed for quality control.

As such, this prior closed system solution suffers disadvantages, in that the closed system solution is overcomplicated. Setting up dozens of tubes, liquid reservoir bags, and reagents requires highly trained labor. This setting up process also takes a long time—even for a skilled technician—to set up, operate, and supervise the machinery. This results in the need for a number of operators that increases proportionally to the number of production system—making it impossible to achieve industrial scale and contain manufacturing costs.

Furthermore, the prior closed system solution is inefficient. Since the architecture of the closed system is still serial, this approach suffers of the same efficiency constraints as the dominant (bench-based) approach. At any given time, most of the subsystems inside of the end-to-end machine are unused. This happens because only one system can be used at a time—this is a serial production line with the hard limit of a single product per production run. Moreover, since some parts of the process are particularly slow (for example, the expansion of the cells into a bioreactor), the "aster subsystems are characterized by an even lower utilization rate than the slower subsystems of the machinery.

Additionally, this closed system lacks design flexibility. This inflexibility drawback is typical of closed systems that are built specifically to execute a particular process. Once the machinery is bought, it is not possible to replace an outdated subsystem with a better one (for example, a subsystem that performs a task better, or with a higher throughput). Any modification to the original closed system machinery requires massive engineering and retooling costs, comparable to building a whole new end-to-end system from scratch. This lack of flexibility is particularly disadvantageous in the case of cell therapy manufacturing—where processes are often tuned and improvement at all stages of clinical development.

Moreover, since each closed system is end-to-end and can only manufacture a single product at a time, the only way to increase throughput is to buy more of these closed systems. This in turn worsens the above-mentioned complexity and underutilization problems. In other words, deploying more complex systems increases the need for skilled operators, which in turn increases the cost of manufacturing. Since each machine is largely underutilized (only one subsystem is active at any given time), chronic underutilization also characterizes a facility that is equipped with multiple end-to-end systems. Furthermore, conventional docking station designs does lend themselves to application in cell therapy manufacturing. For instance, conventional docking stations do not include passive compliance and passive damping systems. Instead, conventional docking stations utilize rigid features, jigs, pins, chamfers, and the like.

Prior solutions, like wedges and chamfers, are easy for robotic systems to interface with. However, wedges and chamfers can only keep a part in place due to gravity. This is inadequate when there are vibrations (i.e., the wedge could move the part outside of the docking station), or when forces perpendicular to gravity could be exerted on the part. For example, if the part is pushed from the side, it can easily slide out of a chamfered docking station. On the other hand, prior solutions like locating pins are hard to operate for robots, because: the locating pins require high accuracy; and the locating pins have a high rigidity, which means that they are not tolerant to misalignments. This affects negatively the repeatability of the process, which would present a higher risk of failure for pick and/or place operations conducting during the manufacture of cell therapies.

Additionally, a major problem of labor-based cell manufacturing processes is that human operators need to sample each batch manually. In cell manufacturing processes, sterility must be always ensured. This is particularly important, because cell therapies cannot be sterilized at the end of the manufacturing process (that would kill the cells). At the same time, guaranteeing the quality of cell manufacturing processes requires a large number of quality control steps. And, in order to perform quality control tests, the cell therapy products must be frequently sampled (i.e. a part of the product must be removed from the batch, while ensuring the sterility of both the sample and the product). In conventional cell manufacturing processes, sampling tasks are executed by human operators.

One disadvantage of this conventional approach to sampling is that human operators are a significant potential source of contamination for cell therapy products. Every time a batch is sampled manually, there is a high risk of contamination because the operator must manually remove a part of the liquid containing the cell product. Even semi-automated sampling procedures, where an operator activates a system that performs the sampling task, present significant risk of contamination due to requiring the presence of a human technicians in close proximity to the process.

Another critical issue is that sampling procedures are performed extremely frequently in cell manufacturing processes. Cell therapy products are sometimes sampled multiple times during a single day. Since cell manufacturing processes have a long completion time (most require more than a week, and many can take up to fifteen to twenty days), manual sampling is repeated dozens of times for every single batch. Repeating risky sampling procedures with this extreme frequency greatly increases the risk of contamination.

Given the above background, there is a need in the art for improved systems, methods, and apparatuses for facilitating an improved manufacture of cell therapies that addresses these dilemmas.

The information disclosed in this background section is only for enhancement of understanding of the general background of the invention and should not be taken as an acknowledgement or any form of suggestion that this information forms the prior art already known to a person skilled in the art.

SUMMARY

Advantageously, the systems and methods detailed in the present disclosure address the shortcomings in the prior art detailed above.

Systems, methods, and apparatuses for broadly implementing a manufacture of a cellular-cellular engineering target at a biological foundry system are provided.

Specifically, exemplary systems, methods, and apparatuses of the present disclosure directly apply to both manufacturing systems for producing small-cellular engineering targets, high-mix cellular engineering targets, personalized cellular engineering targets, or just-in-time production of such targets.

One aspect of the present disclosure is directed to providing a modular biological foundry system for the manufacture of cellular engineering targets, such as cell therapy products. The modular biological foundry system is a fully autonomous manufacturing system that includes multiple modules accommodated by a frame. Each module performs a task in the manufacturing process of the cellular engineering targets. The cellular engineering targets are moved from a first module to a second module by a robotic material transfer system until the manufacture of the cellular engineering target is deemed completed. In some embodiments, the robotic material transfer system includes an articulated handling robot and, optionally, a transport path coupled to the articled handling robot, which is surrounded by the frame. The modules are kept in place by the frame, which also creates a clean-room, sterile environment inside the modular biological foundry system. This modular architecture provided by the frame and the modules allows for efficiently manufacturing individualized cellular engineering targets in a sterile environment. Moreover, the modules are also fault-tolerant and flexible in design, in that modules can be swapped as the manufacture process improves, without affecting the rest of the modular biological foundry system. Inside the modular biological foundry system, the cellular engineering targets are always accommodated inside of modular, sterile closed systems, as known as a rigid cartridge. These cartridges enable the robotic material transfer system to autonomously operate the instruments that perform the manufacturing process.

Another aspect of the present disclosure is directed to providing a modular clean room biological foundry system for producing one or more cellular engineering targets. The modular clean room biological foundry system includes a controller and a communications interface in electrical communication the controller and a plurality of peripheral devices. The plurality of peripheral devices includes an articulated handling robot and a power supply. The articulated handling robot is configured to move a cell therapy cartridge between at least a first biological foundry instrument and a second biological foundry instrument in a plurality of biological foundry instruments configured to produce a portion of the one or more cellular engineering targets. The modular clean room system includes a frame surrounding the articulated handling robot. The frame includes at least two modules in a plurality of modules. A first module in the at least two modules is configured to accommodate a respective biological foundry instrument in the plurality of biological foundry instructions. Moreover, each module in the plurality of modules includes a plurality of elongated members. Each module in the plurality of modules further includes a first plurality of coupling mechanisms for coupling at least two elongated members in the plurality of elongated members. Additionally, each module in the plurality of modules includes a second plurality of coupling mechanisms for removably coupling a respective elongated member in the plurality of elongated members with the frame. Furthermore, each module in the plurality of modules includes a plurality of walls engaged with and supported by the at least two elongated members in the plurality of elongated members. Accordingly, the plurality of walls forms an internal volume of a respective module sealed from an environment, such that a modular clean room biological foundry system is provided.

In some embodiments, the modular clean room biological foundry system further includes a transport path coupled to the articulated handling robot and in electrical communication with the communications interface. The transport path extends from a first end portion of a first wall in the plurality of walls to a second end portion of a second wall in the plurality of walls.

In some embodiments, the transport path provides one degree of freedom of movement to articulated handling robot.

In some embodiments, a first wall in the plurality of walls is configured as an air inflow port and a second wall in the plurality of walls is configured as an air outflow port.

In some embodiments, the first wall includes an air filter mechanism.

In some embodiments, the internal sealed volume is in a range from about 0.3 cubic meters ($m^3$) to about 1.5 $m^3$.

In some embodiments, a second module in the at least two modules is disposed above the first module in the at least two modules.

In some embodiments, the first plurality of coupling mechanism includes a gasket.

Yet another aspect of the present disclosure is directed to providing a docking device for receiving a portable cell therapy cartridge. The docking device includes a base including a substantially planar upper surface configured to support a lower surface of a portable cell therapy cartridge. The docking device further includes an array of a plurality of engagement members protruding upwardly from the substantially planar upper surface of the base. Each engagement member in the array of the plurality of engagement members includes a fixed body protruding upwardly from the substantially planar upper surface of the base. Moreover, each engagement member in the array of the plurality of engagement members includes a spring integrally formed with the fixed body and extending inwardly from an upper end portion of the fixed body oblique to both the substantially planar upper surface of the base and the fixed body. From this, a deformable gap is formed interposing between a surface of the fixed body and a lower end surface of the spring. Accordingly, an upper end surface of the spring is configured to engage a surface of the portable cell therapy cartridge.

In some embodiments, the array of the plurality of engagement members includes at least three engagement members.

In some embodiments, the array of the plurality of engagement members includes twelve engagement members.

In some embodiments, each respective engagement member in the array of the plurality of engagement members opposes a corresponding engagement member in the plurality of engagement members.

In some embodiments, a first distance from a first end portion of a first engagement member in the array of the plurality of engagement members to a second end portion of a second engagement member in the array of the plurality of engagement members is less than a length of the portable device.

In some embodiments, a maximum width of the deformable gap in an unengaged state is in range of from about 0.2 mm to about 1.5 mm.

In some embodiments, a minimum width of the deformable gap in an engaged state is in range of from about 0 mm to about 1.0 mm.

In some embodiments, the spring of each engagement member in the array of the plurality of engagement members is a leaf spring.

In some embodiments, an upper surface of the spring of each engagement member in the array of the plurality of engagement members includes a downward slope towards the substantially planar surface of the base.

In some embodiments, each engagement member in the array of the plurality of engagement members includes an elastic material.

In some embodiments, each engagement member in the array of the plurality of engagement members removably couples with the base.

In some embodiments, a thickness of the spring each engagement member in the array of the plurality of engagement members is in a range of from 2 mm to 15 mm.

In some embodiments, the thickness of the spring is constant along a length of the engagement member in the array of the plurality of engagement members.

In some embodiments, each engagement member in the array of the plurality of engagement members includes polylactic acid (PLA), acrylonitrile butadiene styrene (ABS), polyethylene terephthalate (PET), PET glycol-modified (PETG), polyethylene cotrimethylene terephthalate (PETT), thermoplastic elastomer (TPE), thermoplastic polyurethane (TPU), thermoplastic copolyester (TPC), nylon, polycarbonate (PC), brass, copper, bronze, aluminum, or iron.

In an exemplary embodiment, the invention is directed to providing a rigid cartridge for housing and removably coupling with a soft body bioreactor. An exemplary rigid cartridge includes a plurality of rigid walls defining a fixed interior. The plurality of rigid walls includes a plurality of rigid side walls. At least two adjacent edges in a plurality of edges formed by the plurality rigid side walls includes a radius of curvature greater than zero. A substantially planar upper rigid wall connected to an upper edge portion of each rigid side wall in the plurality of rigid side walls. The substantially planar upper rigid wall includes a plurality of apertures. Each respective aperture in the plurality of apertures is configured to receive and fixedly engage a corresponding connector, which, in an exemplary embodiment, is a member of a group consisting of at least three connectors. Moreover, each respective connector in the at least three connectors in such an embodiment provides communication with a corresponding port in a plurality of ports of the soft body bioreactor. In some embodiment, each respective aperture in a first subset of apertures in the plurality of apertures is encompassed by a corresponding annular hood protruding upwardly from the substantially planar upper rigid wall by a first height greater than or equal to a second height of the corresponding connector of the at least three connectors and integrally formed with the substantially planar upper rigid wall. Additionally, the plurality of apertures includes the first subset of apertures. Each respective aperture in the first subset of apertures is configured to receive and fixedly engage a fluidic connector of the at least three connectors configured to provide fluidic communication with at least a first port in the plurality of ports of the soft body bioreactor, and a second subset of apertures. Furthermore, in various embodiments, each respective aperture in the second subset of apertures is configured to receive and fixedly engage an electrical connector of the at least three connectors configured to provide electrical communication with at least a second port in the plurality of ports of the soft body bioreactor. An exemplary rigid cartridge further includes a seamless lip defined by a lower edge portion of each rigid side wall in the plurality of rigid side walls. Each interior surface in a pair of opposing interior surfaces of two rigid side walls in the plurality of rigid side walls includes a respective first mating mechanism configured to engage a corresponding second mating mechanism of the soft body bioreactor, such that a pair of opposing end portions of the soft body bioreactor is removably coupled with the rigid cartridge.

In some embodiments, the electrical connector includes a pressure control mechanism, a pH sensor, a dissolved oxygen sensor, a temperature sensor, a flow rate sensor, a mass sensor, or a combination thereof.

In some embodiments, the fluidic connector includes a pressure control mechanism, an inlet port, a sampling port, an outlet port, or a combination thereof.

In some embodiments, the fluidic connector includes a valve configured to control a flow of a fluid through a corresponding fluidic port.

In some embodiments, a first internal diameter at an upper end portion of a respective connector is less than a second internal diameter at a lower end portion of the respective connector.

In some embodiments, at least one rigid wall in the plurality of rigid walls further includes a gate mechanism configured to provide access to the fixed internal cavity of the rigid housing.

In some embodiments, a length of the gate mechanism is greater than or equal to a cross-sectional area of the soft body bioreactor.

In some embodiments, the gate mechanism is a hinge gate mechanism or a hinge gate mechanism.

In some embodiments, each rigid coupling mechanism protrudes from the substantially upper planar surface of the at least one rigid wall of the rigid housing.

In some embodiments, the rigid cartridge further includes a corresponding cap for each respective connector in the plurality of connectors. The corresponding cap encompasses the respective connector.

In some embodiments, an exterior surface of the corresponding cap includes a third mating mechanism confirmed to engage a fourth mating mechanism of an articulated handling robot.

In some embodiments, the corresponding cap is configured to disengage the respective connector in the plurality of connectors when subject to a lateral force.

In some embodiments, each rigid coupling mechanism of each respective port in the at least one electrical port is a push coupling mechanism.

In various embodiments of the present invention there is provided a rigid cartridge for housing and removably coupling with a soft body bioreactor. An exemplary rigid cartridge includes a plurality of rigid walls defining a rigid housing including an open face forming a seamless lip at a lower end portion of the rigid cartridge. The plurality of rigid walls exposes a fixed interior configured to house the soft body bioreactor. An interior surface of a first rigid wall in the plurality of rigid walls includes a first mating mechanism configured to engage a second mating mechanism of the soft body bioreactor. From this, the soft body bioreactor is removably coupled with the rigid cartridge and accommodates the soft body bioreactor in the fixed interior of the rigid cartridge. Additionally, at least one rigid wall in the plurality of rigid walls includes a substantially planar upper surface comprising at least aperture. Each respective aperture of the at least one aperture is encompassed by an annular hood protruding upwardly from the substantially planar upper surface and integrally formed with the at least one rigid wall. An exemplary at least one aperture is configured to receive and fixed engage a corresponding connector which is a member of a group consisting of at least one connector. Furthermore, each respective connector in the at least one connector includes at least one rigid coupling mechanism that provides communication with a corresponding plurality of ports of the soft body bioreactor. Additionally, the corresponding plurality of ports includes at least one electrical port and at least one fluidic port.

The methods and apparatuses of the present disclosure have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 19A is a side view of another rigid cartridge, in accordance with an embodiment of the present disclosure;

FIG. 19B is a side view of yet another rigid cartridge, in accordance with an embodiment of the present disclosure;

FIG. 19C is a side view of yet another rigid cartridge, in accordance with an embodiment of the present disclosure;

Figure 1:
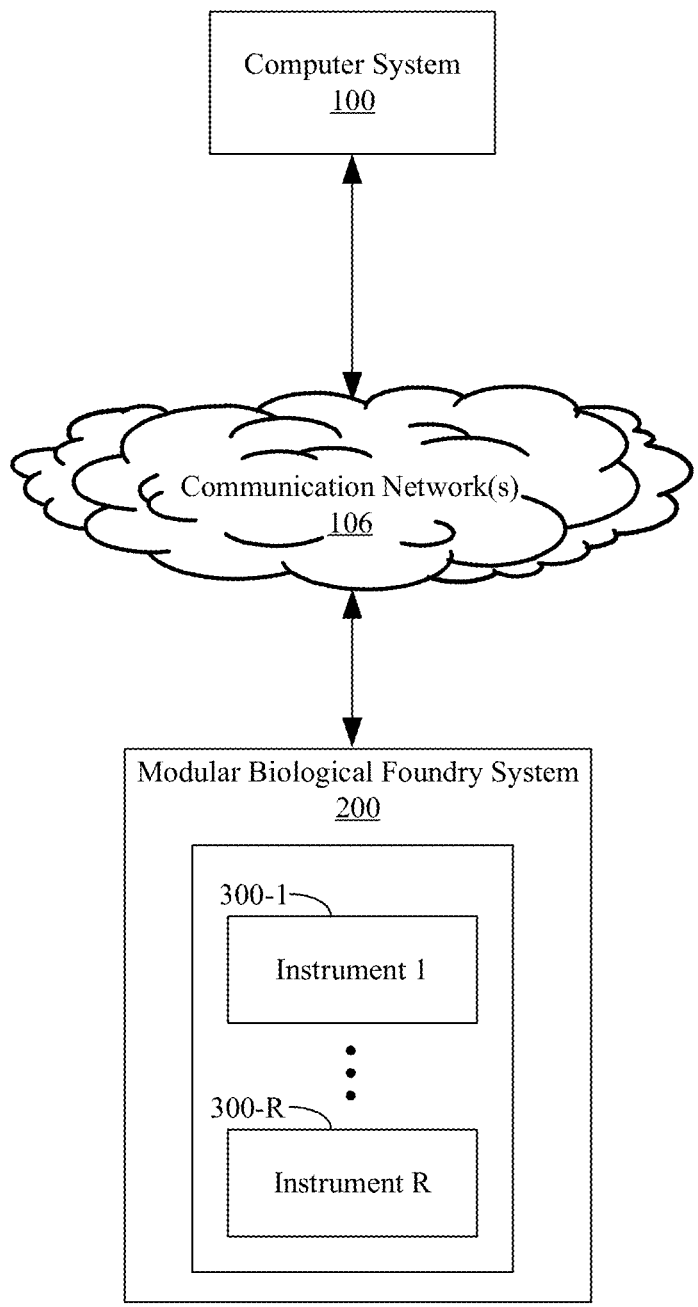
FIG. 1 illustrates an exemplary biological foundry workflow system topology including a computer system and a plurality of instruments associated with a biological foundry, in accordance with an embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present disclosure provides systems, methods, and apparatuses for facilitating automated modular manufacture of cellular engineering targets. Exemplary systems, methods, and apparatuses for the manufacturing of cellular engineering targets of the present disclosure includes the advantages of modularity, flexibility, and scalability. Moreover, exemplary systems, methods, and apparatuses of the present disclosure retain the benefits of a conventional closed-system processes, such as providing a sterile clean room environment, without sacrificing the aforementioned advantages. Furthermore, exemplary systems, methods, and apparatus of the present disclosure leverage advanced robotic features and technologies that enables the transformation of cellular engineering target manufacturing from labor-based and low-throughput processes to fully industrialized, high-throughput processes with high scale, efficiency and repeatability. Accordingly, an exemplary modular biological foundry system provided by the present disclosure offers the advantages of increased throughput, in that multiple separate cellular engineering targets can be produced at the same time within the modular biological foundry system. This is enabled by a parallel architecture of modules of the modular biological foundry system. Adding more copies of modules that facilitate slower processes decreases the overall cycle time of modular biological foundry system. Additionally, the systems, methods, and apparatus of exemplary embodiments provide increased efficiency by reducing bottlenecks when manufacturing a cellular engineering target. Exemplary modules have high utilization rates due to the parallel architecture of the modular biological foundry system. Organizing the modules associated with faster manufacturing processes in groups, while adding more copies of the modules associated with slower manufacturing processes, results in reduction or elimination of production bottlenecks. Furthermore, exemplary systems, methods, and apparatus of the present disclosure provides increased safety, such as improved sterility within a modular biological foundry system. Since the manufacture of cellular engineering targets can be entirely automated and contained in a clean room (e.g., the modular biological foundry system forms an entirely self-contained, sterile clean room space), there are no human sources of contamination around the cellular engineering targets. Additionally, exemplary systems, methods, and apparatus of the present disclosure allows for higher consistency and repeatability when manufacturing cellular engineering targets since the entire cell manufacturing process is executed by a robotic material transfer system within the modular biological foundry system. This fully automated approach ensures more repeatability and traceability for the manufacturing process. Finally, the systems, methods, and apparatus of the present disclosure provide improved flexibility in design. An exemplary modular biological foundry system is designed to allow the addition of new modules, or the removal of old modules. If a more advanced module becomes available, it can be added to modular biological foundry system without influencing the rest of the system. Similarly, if an old module must be removed, it is possible to do so without affecting the rest of the system. This makes it possible to implement different processes (by choosing the appropriate initial set of modules), increase throughput (by adding more modules to a cluster, or by building new copies of a whole modular biological foundry system), and improve a process (by swapping pre-existing modules with improved ones). And since the flow of materials within an exemplary modular biological foundry system is managed by the robotic material transfer system, the sequence of operations in the manufacturing process can simply be updated by updating the software that controls the modular biological foundry system.

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first instrument could be termed a second instrument, and, similarly, a second instrument could be termed a first instrument, without departing from the scope of the present disclosure. The first instrument and the second instrument are both instruments, but they are not the same instrument.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Furthermore, when a reference number is given an "$i^{th}$" denotation, the reference number refers to a generic component, set, or embodiment. For instance, an application termed "application i" refers to the $i^{th}$ application in a plurality of applications.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

An aspect of the present disclosure is directed to providing systems, methods, and apparatuses for facilitating automated modular manufacture of cell therapies.

Figure 2:
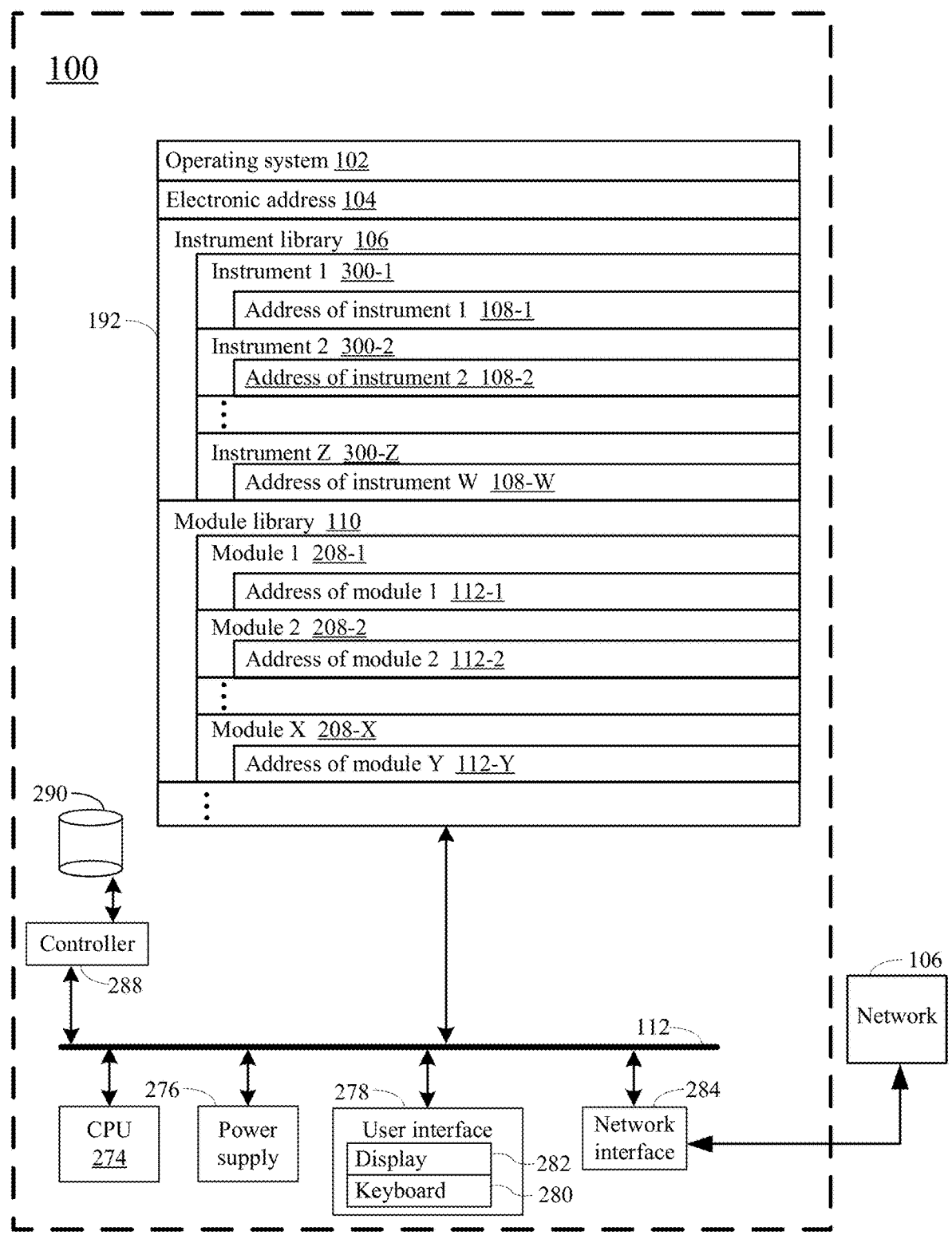
FIG. 2 illustrates various modules and/or components of a computer system, in accordance with an exemplary embodiment of the present disclosure.
Figure 3:
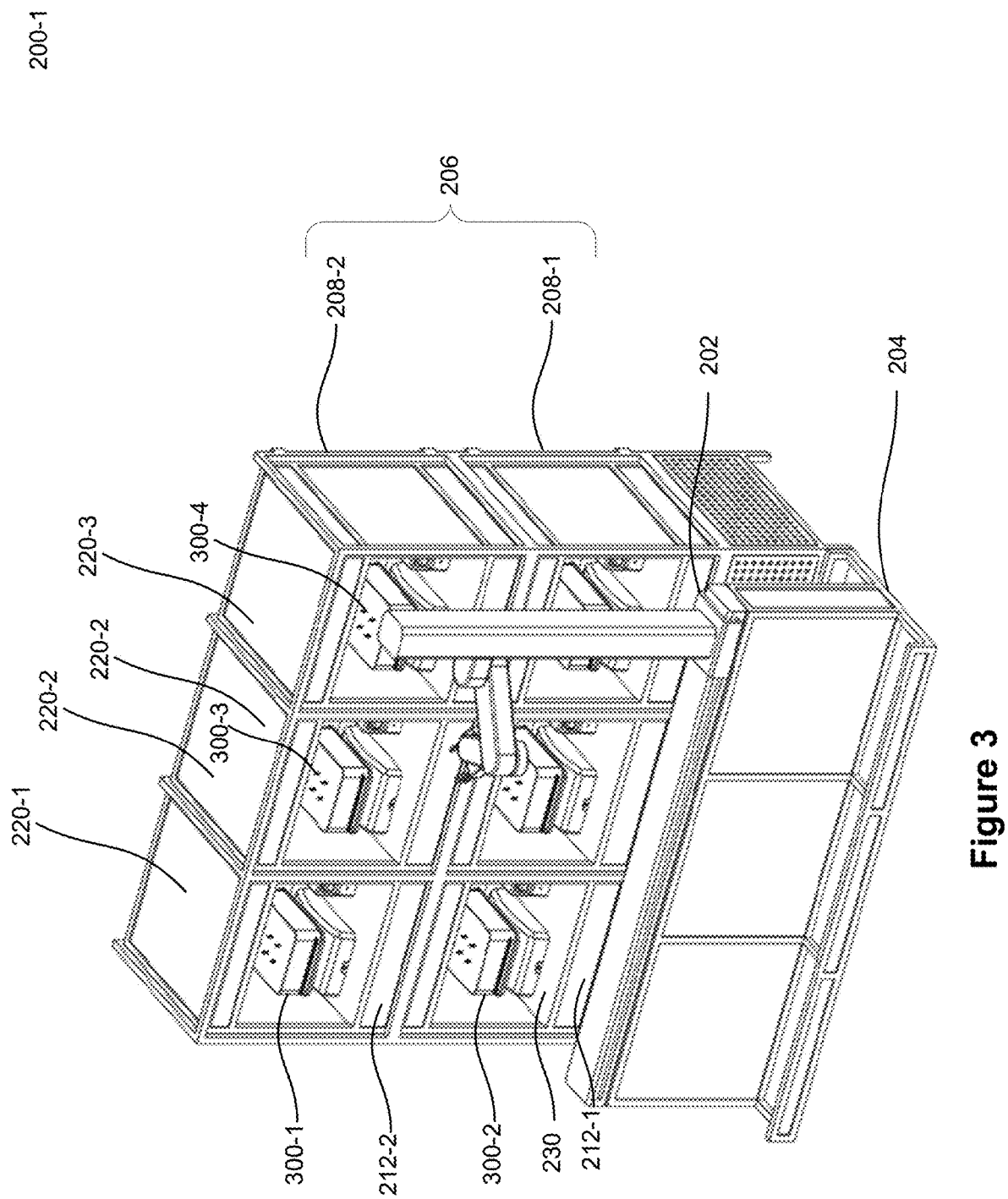
FIG. 3 is a perspective view of a modular clean room biological foundry including a plurality of instruments, in accordance with an embodiment of the present disclosure.
Figure 7:
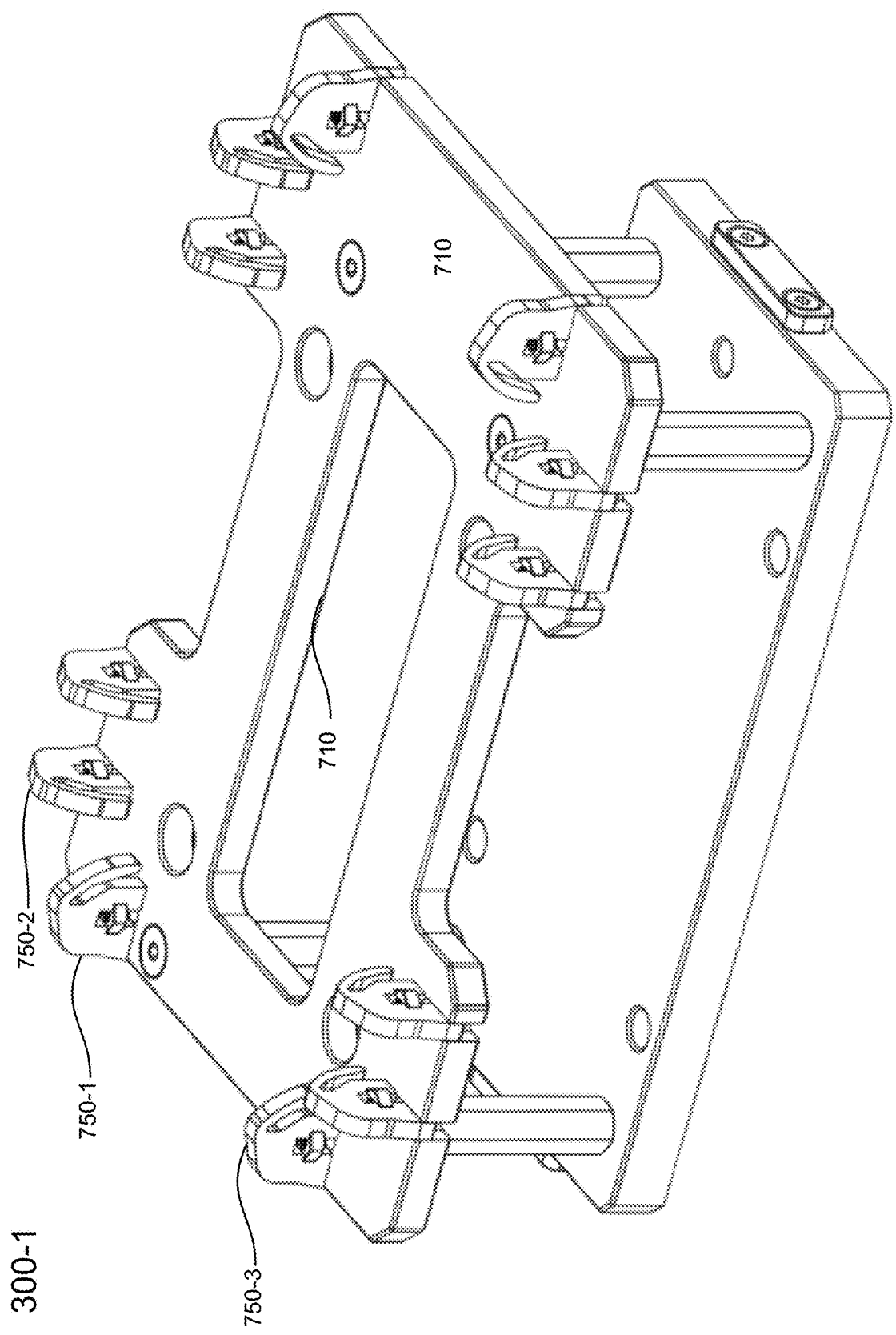
FIG. 7 is a perspective view of a docking device instrument, in accordance with an embodiment of the present disclosure.
Figure 8:
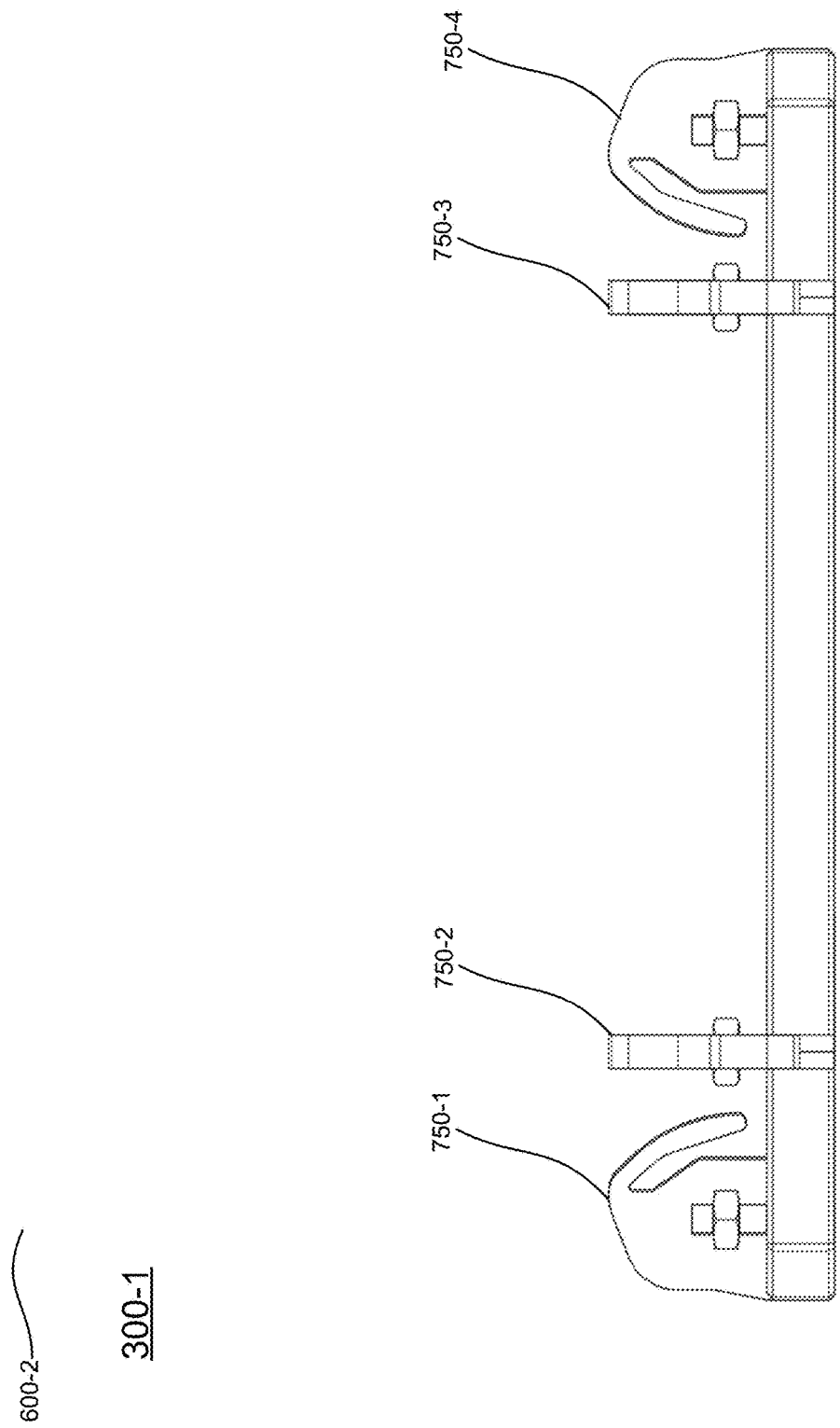
FIG. 8 is a side view of a docking device instrument, in accordance with an embodiment of the present disclosure.

A detailed description of an exemplary system 10 for implementing the automated modular production of cellular engineering targets (e.g., cell therapies) at a biological foundry 200 is described in conjunction with FIG. 1 and FIG. 2. As such, FIG. 1 and FIG. 2 collectively illustrate an exemplary topology of the system 10. In the topology, there is a computer system 100 for generating a workflow that produces a plurality of cellular engineering targets, and providing scheduling of a plurality of instruments (e.g., first instrument 300-1, . . . , instrument 300-R of FIG. 1; instrument 300-1 of FIG. 7, instrument 300-2 of FIG. 8, instrument 300) in correlation with a corresponding plurality of biological foundry operations, and oversight of the manufacture of the plurality of cellular engineering targets at the modular biological foundry system.

In some embodiments, each cellular engineering target (e.g., cellular engineering target 2 of FIG. 18B), in the context of biological engineering at a modular biological foundry system, is one of the objectives of a research and development project that defines the desired biological trait to be achieved. The cellular engineering target can be either quantitative or qualitative. For example, in one embodiment, a cellular engineering target(s) can be a genetic configuration for a biosynthetic pathway that produces more compound of interest than a current level. In another embodiment, the cellular engineering target(s) is a genetic configuration for a microbial host that has a tolerance to an inhibitor over X mg/L.

In some embodiments, each cellular engineering target includes modified immune cells or precursors thereof, such as modified T cells, including a chimeric antigen receptor (CAR). Thus, in some embodiments, the immune cell is genetically modified at a modular biological foundry system to express the CAR. In some embodiments, CARs include an antigen binding domain, a transmembrane domain, a hinge domain, and an intracellular signaling domain.

In some embodiments, the antigen binding domain is operably linked to another domain of the CAR, such as the transmembrane domain or the intracellular domain, for expression in the cellular engineering target. In some embodiments, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains, any of the intracellular domains or cytoplasmic domains, or any of the other domains that may be included in a CAR. In some embodiments, a cellular engineering target CAR of the present disclosure includes a spacer domain. In some embodiments, each of the antigen binding domain, transmembrane domain, and intracellular domain is separated by a linker.

In the present disclosure, the cellular engineering targets generally include mammalian cells, and typically include human cells. In some embodiments, the cellular engineering target is derived from the blood, bone marrow, lymph, or lymphoid organs. In some embodiments, the cellular engineering targets includes cells of the immune system, such as cells of innate or adaptive immunity, e.g., myeloid or lymphoid cells, including lymphocytes, typically T cells and/or NK cells. In some embodiments, the cellular engineering targets include stem cells, such as multipotent and pluripotent stem cells, including induced pluripotent stem cells (iPSCs). The cellular engineering targets typically are primary cells, such as those isolated directly from a subject and/or isolated from a subject and frozen. In some embodiments, the cellular engineering targets include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, degree of differentiation, or a combination thereof. With reference to the subject to be treated, the cellular engineering targets be allogeneic and/or autologous. In some embodiments, the modular biological foundry system facilitates manufacturing the cellular engineering targets by isolating cells from the subject, preparing the cells, processing the cells, culturing the cells, engineering the cells, and re-introducing the cells into the same subject, before or after cryopreservation. In some embodiments, one or more of these steps is performed at modules 208 of modular biological foundry system 200 by utilizing rigid cartridge 1100 and a robot material transfer system.

In some embodiments, among the sub-types and subpopulations of T cells and/or of CD4+ and/or of CD8+ T cells of the cellular engineering targets are naive T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cellular engineering targets are natural killer (NK) cells. In some embodiments, the cellular engineering targets are monocytes or granulocytes, e.g., myeloid cells, macrophages, neutrophils, dendritic cells, mast cells, eosinophils, and/or basophils.

Accordingly, the present disclosure provides systems and methods for producing or generating a cellular engineering target that is a modified immune cell or precursor thereof (e.g., a T cell) of the invention for tumor immunotherapy, e.g., adoptive immunotherapy. The cellular engineering targets generally are engineered by introducing one or more nucleic acids encoding a subject CAR, dominant negative receptor and/or switch receptor, and/or bispecific antibody, and/or combinations thereof.

In some embodiments, one or more nucleic acids encoding the subject CAR, dominant negative receptor and/or switch receptor, and/or bispecific antibody is introduced into a cell by an expression vector. Expression vectors including a nucleic acid sequence encoding a subject CAR, dominant negative receptor and/or switch receptor, and/or bispecific antibody, and/or combinations thereof, of the present disclosure are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the subject CAR, dominant negative receptor and/or switch receptor, and/or bispecific antibody, and/or combinations thereof, in the host cell. In some embodiments, the adenovirus genome is a 36 kb, linear, double stranded DNA, where a foreign DNA sequence (e.g., a nucleic acid encoding a subject CAR, dominant negative receptor and/or switch receptor, and/or bispecific antibody, and/or combinations thereof) may be inserted to substitute large pieces of adenoviral DNA in order to make the expression vector of the present invention. Additional details and information can be found at Danthinne et al., 2002, Gene Therapy, 7(20, pg. 1707, which is hereby incorporated by reference in its entirety.

Another expression vector is based on an adeno associated virus, which takes advantage of the adenovirus coupled systems. This AAV expression vector has a high frequency of integration into the host genome. Moreover, this AAV expression can infect non-dividing cells, thus making it useful for delivery of genes into mammalian cells, for example, in tissue cultures or in vivo. The AAV vector has a broad host range for infectivity.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding a subject CAR, dominant negative receptor and/or switch receptor, and/or bispecific antibody, and/or combinations thereof) into the viral genome at certain locations to produce a virus that is replication defective. Though the retrovirus vectors are able to infect a broad variety of cell types, integration and stable expression of the subject CAR, dominant negative receptor and/or switch receptor, and/or bispecific antibody, and/or combinations thereof, requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a subject CAR, dominant negative receptor and/or switch receptor, and/or bispecific antibody, and/or combinations thereof.

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistic, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell. In some embodiments, one or more of these steps is performed at modules 208 of modular biological foundry system 200 by utilizing rigid cartridge 1100 and a robot material transfer system.

The present invention also provides genetically engineered cells which include and stably express a subject CAR, dominant negative receptor and/or switch receptor, and/or bispecific antibody, and/or combinations thereof, of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

In some embodiments, modified cells (e.g., including a subject CAR, dominant negative receptor and/or switch receptor, and/or expresses and secretes a bispecific antibody, and/or combinations thereof) is produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a subject CAR, dominant negative receptor and/or switch receptor, and/or bispecific antibody, and/or combinations thereof, of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, Sambrook et al, 2001, "Molecular Cloning: A Laboratory Manual," Cold Spring Harbor Laboratory, print, which is hereby incorporated by reference in its entirety. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

In some embodiments, lipids suitable for use in the manufacture of a cellular engineering target at a modular biological foundry system is obtained from commercial sources. Stock solutions of lipids in chloroform or chloroform/methanol can be stored at about −20 degrees C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention. In some embodiments, one or more of these assays is performed at modules 208 of modular biological foundry system 200 by utilizing rigid cartridge 1100 and a robot material transfer system.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

In some embodiments, chemical structures that have the ability to promote stability and/or translation efficiency of the RNA are used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art.

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a subject CAR, dominant negative receptor and/or switch receptor, and/or bispecific antibody, and/or combinations thereof, of the present disclosure will be RNA, e.g., in vitro synthesized RNA. Methods for in vitro synthesis of RNA are known in the art; any known method can be used to synthesize RNA comprising a sequence encoding a subject CAR, dominant negative receptor and/or switch receptor, and/or bispecific antibody, and/or combinations thereof. Methods for introducing RNA into a host cell are known in the art. Introducing RNA comprising a nucleotide sequence encoding a subject CAR, dominant negative receptor and/or switch receptor, and/or bispecific antibody, and/or combinations thereof, into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a subject CAR, dominant negative receptor and/or switch receptor, and/or bispecific antibody, and/or combinations thereof.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. The various parameters including electric field strength required for electroporation of any known cell type are generally known in the relevant research literature as well as numerous patents and applications in the field. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the subject CAR, dominant negative receptor and/or switch receptor, and/or bispecific antibody, and/or combinations thereof. In some embodiments, the cells (e.g. T cells) can be incubated or cultivated prior to, during or subsequent to the introduction of the nucleic acid molecule encoding the subject CAR, dominant negative receptor and/or switch receptor, and/or bispecific antibody, and/or combinations thereof, such as prior to, during or subsequent to the transduction of the cells with a viral vector (e.g. lentiviral vector) encoding the subject CAR, dominant negative receptor and/or switch receptor, and/or bispecific antibody, and/or combinations thereof. In some embodiments, the method includes activating or stimulating cells with a stimulating or activating agent (e.g. anti-CD3/anti-CD28 antibodies) prior to introducing the nucleic acid molecule encoding the subject CAR, dominant negative receptor and/or switch receptor, and/or bispecific antibody, and/or combinations thereof. In some embodiments, one or more of these steps is performed at modules 208 of modular biological foundry system 200 by utilizing rigid cartridge 1100 and a robot material transfer system.

In some embodiments, where the nucleic acid sequences encoding the subject CAR, dominant negative receptor and/or switch receptor, and/or bispecific antibody, and/or combinations thereof, of the present invention reside on one or more separate nucleic acid sequences, the order of introducing each of the one or more nucleic acid sequences may vary. For example, a nucleic acid sequence encoding a subject CAR and dominant negative receptor and/or switch receptor may first be introduced into the host cell, followed by introduction of a nucleic acid sequence encoding a subject bispecific antibody. For example, a nucleic acid sequence encoding a subject bispecific antibody may first be introduced into the host cell, followed by introduction of a nucleic acid sequence encoding a subject CAR and dominant negative receptor and/or switch receptor. In some embodiments, each of the one or more nucleic acid sequences are introduced into the host cell simultaneously. Those of skill in the art will be able to determine the order in which each of the one or more nucleic acid sequences are introduced into the host cell.

Prior to expansion, a source of immune cells is obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some embodiments, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, one or more of these steps is performed at modules 208 of modular biological foundry system 200 by utilizing rigid cartridge 1100 and a robot material transfer system.

In some examples, cells from the circulating blood of a subject are obtained, e.g., by apheresis or leukapheresis. The samples, in some embodiments, contain lymphocytes, including T cells, monocytes, granulocytes, B cells, other nucleated white blood cells, red blood cells, and/or platelets, and, in some embodiments, contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient. In some embodiments, one or more of these steps is performed at modules 208 of modular biological foundry system 200 by utilizing rigid cartridge 1100 and a robot material transfer system.

In one embodiment, immune cells are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample are removed and the cells directly resuspended in culture media. In some embodiments, one or more of these steps is performed at modules 208 of modular biological foundry system 200 by utilizing rigid cartridge 1100 and a robot material transfer system.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. In some embodiments, one or more of these steps is performed at modules 208 of modular biological foundry system 200 by utilizing rigid cartridge 1100 and a robot material transfer system.

Such separation steps can be based on positive selection, in which the cells having bound the reagents are retained for further use, and/or negative selection, in which the cells having not bound to the antibody or binding partner are retained. In some examples, both fractions are retained for further use. In some embodiments, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker.sup.high) of one or more particular markers, such as surface markers, or that are negative for (marker.sup.−) or express relatively low levels (marker.sup.low) of one or more markers. For example, in some embodiments, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some embodiments, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which, in some embodiments, is particularly robust in such sub-populations. In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some embodiments, it is based on negative selection for cells expressing or highly expressing CD45RA and/or granzyme B. In some embodiments, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections, in some embodiments, are carried out simultaneously and in other aspects are carried out sequentially, in either order. In some embodiments, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some embodiments, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL. In some embodiments, one or more of these steps is performed at modules 208 of modular biological foundry system 200 by utilizing rigid cartridge 1100 and a robot material transfer system.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques. In some embodiments, one or more of these steps is performed at modules 208 of modular biological foundry system 200 by utilizing rigid cartridge 1100 and a robot material transfer system.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immuno-adherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. In some embodiments, one or more of these steps is performed at modules 208 of modular biological foundry system 200 by utilizing rigid cartridge 1100 and a robot material transfer system.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80 degrees C. at a rate of 1 degrees C. per minute and stored in the vapor phase of a liquid nitrogen storage tank. Other methods of controlled freezing may be used as well as uncontrolled freezing immediately at −20 degrees C. or in liquid nitrogen. In some embodiments, one or more of these steps is performed at modules 208 of modular biological foundry system 200 by utilizing rigid cartridge 1100 and a robot material transfer system.

In one embodiment, the population of T cells includes cells such as peripheral blood mononuclear cells, cord blood cells, a purified population of T cells, and a T cell line. In another embodiment, peripheral blood mononuclear cells include the population of T cells. In yet another embodiment, purified T cells include the population of T cells.

In certain embodiments, T regulatory cells (Tregs) is isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. In some embodiments, one or more of these steps is performed at modules 208 of modular biological foundry system 200 by utilizing rigid cartridge 1100 and a robot material transfer system.

Whether prior to or after modification of cells to express a subject CAR, dominant negative receptor, and/or switch receptor, and/or bispecific antibody, and/or combinations thereof, the cells can be activated and expanded in number using methods known to one of skill in the art. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or an antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 and these can be used in the present disclosure as can other methods and reagents known in the art.

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20-fold to about 50-fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein. In some embodiments, one or more of these steps is performed at modules 208 of modular biological foundry system 200 by utilizing rigid cartridge 1100 and a robot material transfer system.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time. In some embodiments, one or more of these steps is performed at modules 208 of modular biological foundry system 200 by utilizing rigid cartridge 1100 and a robot material transfer system.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging. Therefore, the number of population doublings of a culture is greater than the passage number. The expansion of cells (i.e., the number of population doublings) during the period between passaging depends on many factors, including but not limited to the seeding density, substrate, medium, and time between passaging. In some embodiments, one or more of these steps is performed at modules 208 of modular biological foundry system 200 by utilizing rigid cartridge 1100 and a robot material transfer system.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-.alpha. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, .alpha.-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37 degrees C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20-fold to about 50-fold, or more. In one embodiment, human T regulatory cells are expanded via anti-CD3 antibody coated KT64.86 artificial antigen presenting cells (aAPCs). In one embodiment, human T regulatory cells are expanded via anti-CD3 antibody coated K562 artificial antigen presenting cells (aAPCs). In some embodiments, one or more of these steps is performed at modules 208 of modular biological foundry system 200 by utilizing rigid cartridge 1100 and a robot material transfer system.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function. In some embodiments, one or more of these steps is performed at modules 208 of modular biological foundry system 200 by utilizing rigid cartridge 1100 and a robot material transfer system.

Example 1: Methods of Treatment of a Subject Using Cellular Engineering Targets

In some embodiments, the cellular engineering targets is modified cells (e.g., T cells). In some embodiments, a composition for immunotherapy includes the modified cells. In some embodiments, the composition includes a pharmaceutical composition and further include a pharmaceutically acceptable carrier. In some embodiments, a therapeutically effective amount of the pharmaceutical composition include the modified T cells is administered.

In one aspect, the present disclosure includes a method for adoptive cell transfer therapy including administering to a subject in need thereof a cellular engineering target including a modified T cell of the present disclosure. In another aspect, the present disclosure includes a method of treating a disease or condition in a subject including administering to a subject in need thereof a population of modified T cells In some embodiments, a method of treating a disease or condition in a subject in need thereof includes administering to the subject a modified cell (e.g., modified T cell) of the present invention. In one embodiment, the method of treating a disease or condition in a subject in need thereof comprises administering to the subject a modified cell (e.g., a modified T cell) comprising a subject CAR, dominant negative receptor and/or switch receptor, and/or a bispecific antibody, and/or combinations thereof. In one embodiment, the method of treating a disease or condition in a subject in need thereof comprises administering to the subject a modified cell (e.g., a modified T cell) comprising a subject CAR (e.g., a CAR having affinity for PSMA on a target cell) and a dominant negative receptor and/or switch receptor. In one embodiment, the method of treating a disease or condition in a subject in need thereof comprises administering to the subject a modified cell (e.g., a modified T cell) comprising a subject CAR (e.g., a CAR having affinity for PSMA on a target cell), a dominant negative receptor and/or switch receptor, and wherein the modified cell is capable of expressing and secreting a bispecific antibody.

Methods for administration of immune cells for adoptive cell therapy are known and may be used in connection with the provided methods and compositions. In some embodiments, autologous transfer conducts the cell therapy, e.g., adoptive T cell therapy, in which the cells are isolated and/or otherwise prepared from the subject who is to receive the cell therapy, or from a sample derived from such a subject. Thus, in some embodiments, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, by isolating and/or otherwise preparing the cells from a subject other than a subject who is to receive or who ultimately receives the cell therapy, e.g., a first subject. In such embodiments, the method includes administering to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the method includes treating the subject with a therapeutic agent targeting the disease or condition, e.g., the tumor, prior to administering of the cells or composition containing the cells. In some embodiments, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administering the cellular engineering target effectively treats the subject despite the subject having become resistant to another therapy.

In some embodiments, the subject is responsive to the other therapeutic agent, and treatment with the therapeutic agent reduces disease burden. In some embodiments, the subject is initially responsive to the therapeutic agent, but exhibits a relapse of the disease or condition over time. In some embodiments, the subject has not relapsed. In some such embodiments, a determination that the subject is at risk for relapse is provided, such as at a high risk of relapse, and thus the method includes administering cellular engineering target prophylactically, e.g., to reduce the likelihood of or prevent relapse. In some embodiments, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administrating the cellular engineering target effectively treats the subject despite the subject having become resistant to another therapy.

In some embodiments, the method includes administering the modified immune cells of the cellular engineering target of the present disclosure to an animal, preferably a mammal, even more preferably a human, to treat a cancer. In addition, in some embodiments, the cellular engineering target of the present invention is utilized for the treatment of any condition related to a cancer, especially a cell-mediated immune response against a tumor cell(s), where it is desirable to treat or alleviate the disease. The types of cancers with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, carcinomas amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

In some embodiments, sarcomas amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Prostate adenocarcinoma is an extremely common and lethal disease. Prostate cancer is the most common malignancy among men. Prostate cancer is the second-leading cause of cancer-related deaths among men, accounting for an estimated 10% of annual male cancer deaths. PSMA is highly expressed in malignant prostate tissue, with low-levels of expression in some normal human tissues. Under normal physiologic conditions, PSMA is expressed in the prostate gland (secretory acinar epithelium), kidney (proximal tubules), nervous system glia (astrocytes and Schwann cells), and the small intestine (jejunal brush border). PSMA is much more highly expressed in prostate epithelium and is significantly unregulated in malignant prostate tissues. PSMA expression in normal cells has been found to be 100-fold to 1000-fold less than in prostate carcinoma cells. PSMA expression increases significantly during the transformation from benign prostatic hyperplasia to prostatic adenocarcinoma. PSMA expression has been found to be directly correlated with the histologic grade of malignant prostate tissue and increases with more advanced disease (i.e. highest PSMA expression found in prostate cancer metastases in lymph node and bone).

In one embodiment, the methods of the invention are useful for treating prostate cancer, for example advanced castrate-resistant prostate cancer. It should be readily understood by one of ordinary skill in the art that any type of cancer wherein the PSMA tumor antigen is expressed, can be treated using the methods of the present invention. For example, neovascular expression of PSMA was found in non-small cell lung cancer. Accordingly, the methods of the invention may also be useful for treating non-small cell lung cancer (NSCLC).

In certain exemplary embodiments, the modified immune cells of the invention treat prostate cancer. In one embodiment, a method of the present disclosure provides a treatment for castrate-resistant prostate cancer. In one embodiment, a method of the present disclosure provides a treatment for advanced castrate-resistant prostate cancer. In one embodiment, a method of the present disclosure provides a treatment for metastatic castrate-resistant prostate cancer. In one embodiment, a method of the present disclosure provides a treatment for metastatic castrate-resistant prostate cancer, wherein the patient with metastatic castrate-resistant prostate cancer has .gtoreq.10% tumor cells expressing PSMA. In one embodiment, a method of the present disclosure provides a treatment for castrate-resistant prostate adenocarcinoma, wherein the patient has castrate levels of testosterone (e.g., <50 ng/mL) with or without the use of androgen deprivation therapy.

In certain embodiments, the method includes providing the subject with a secondary treatment. Secondary treatments include but are not limited to chemotherapy, radiation, surgery, and medications.

In some embodiments, the method includes administering the cellular engineering in dosages and routes and at times determined based on appropriate pre-clinical and clinical experimentation and trials. In some embodiments, the method includes administering cellular engineering target compositions multiple times at dosages within these ranges. The administrating of the cells of the invention includes other methods useful to treat the desired disease or condition as determined by those of skill in the art.

In some embodiments, administrating of the cellular engineering target of the present disclosure includes any convenient manner known to those of skill in the art. In some embodiments, administrating of the cellular engineering target includes aerosol inhalation, injection, ingestion, transfusion, implantation or transplantation. In some embodiments, administrating of the cellular engineering target compositions includes transarterially, subcutaneously, intradermally, intratumorally, intranodally, intramedullary, intramuscularly, by intravenous (i.v.) injection, or intraperitoneally. In some embodiments, administrating of the cellular engineering target includes injection into a site of the subject, a local disease site in the subject, alymph node, an organ, a tumor, and the like.

In some embodiments, administrating of the cellular engineering target is at a desired dosage, which includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the method includes administering the populations or sub-types of cells, such as CD8.sup.+ and CD4.sup.+ T cells, at or within a tolerated difference of a desired dose of total cells, such as a desired dose of T cells. In some embodiments, the desired dose is a desired number of cells or a desired number of cells per unit of body weight of the subject to whom the cells are administered, e.g., cells/kg. In some embodiments, the desired dose is at or above a minimum number of cells or minimum number of cells per unit of body weight. In some embodiments, among the total cells, the individual populations or sub-types are present at or near a desired output ratio (such as CD4.sup.+ to CD8.sup.+ ratio), e.g., within a certain tolerated difference or error of such a ratio.

In some embodiments, the method includes administrating of the cellular engineering target at or within a tolerated difference of a desired dose of one or more of the individual populations or sub-types of cells, such as a desired dose of CD4+ cells and/or a desired dose of CD8+ cells. In some embodiments, the desired dose is a desired number of cells of the sub-type or population, or a desired number of such cells per unit of body weight of the subject to whom the cells are administered, e.g., cells/kg. In some embodiments, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4.sup.+ to CD8$^+$ cells, and/or is based on a desired fixed or minimum dose of CD4$^+$ and/or CD8$^+$ cells.

In some embodiments, the method includes administrating of the cellular engineering target to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1 \times 10^5$ cells/kg to about $1 \times 10^{11}$ cells/kg, $10^4$, and at or about $10^{11}$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1 \times 10^5$ T cells/kg, $1.5 \times 10^5$ T cells/kg, $2 \times 10^5$ T cells/kg, or $1 \times 10^6$ T cells/kg body weight. In other exemplary embodiments, a suitable dosage range of modified cells for use in a method of the present disclosure includes, without limitation, from about $1 \times 10^5$ cells/kg to about $1 \times 10^6$ cells/kg, from about $1 \times 10^6$ cells/kg to about $1 \times 10^7$ cells/kg, from about $1 \times 10^7$ cells/kg about $1 \times 10^8$ cells/kg, from about $1 \times 10^8$ cells/kg about $1 \times 10^9$ cells/kg, from about $1 \times 10^9$ cells/kg about $1 \times 10^{10}$ cells/kg, from about $1 \times 10^{10}$ cells/kg about $1 \times 10^{11}$ cells/kg. In an exemplary embodiment, a suitable dosage for use in a method of the present disclosure is about $1 \times 10^8$ cells/kg. In an exemplary embodiment, a suitable dosage for use in a method of the present disclosure is about $1 \times 10^7$ cells/kg. In other embodiments, a suitable dosage is from about $1 \times 10^7$ total cells to about $5 \times 10^7$ total cells. In some embodiments, a suitable dosage is from about $1 \times 10^8$ total cells to about $5 \times 10^8$ total cells. In some embodiments, a suitable dosage is from about $1.4 \times 10^7$ total cells to about $1.1 \times 10^9$ total cells. In an exemplary embodiment, a suitable dosage for use in a method of the present disclosure is about $7 \times 10^9$ total cells. In an exemplary embodiment, a suitable dosage is from about $1 \times 10^7$ total cells to about $3 \times 10^7$ total cells.

In some embodiments, the dose of total cells and/or dose of individual sub-populations of cells is within a range of between at or about $1 \times 10^5$ cells/m$^2$ to about $1 \times 10^{11}$ cells/m$^2$. In an exemplary embodiment, the dose of total cells and/or dose of individual sub-populations of cells is within a range of between at or about $1 \times 10^7$/m$^2$ to at or about $3 \times 10^7$/m$^2$. In an exemplary embodiment, the dose of total cells and/or dose of individual sub-populations of cells is within a range of between at or about $1 \times 10^8$/m$^2$ to at or about $3 \times 10^8$/m$^2$. In some embodiments, the dose of total cells and/or dose of individual sub-populations of cells is the maximum tolerated dose by a given patient.

In some embodiments, the method includes administrating the cellular engineering target at or within a certain range of error of between at or about $10^4$ and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1 \times 10^5$ CD4$^+$ and/or CD8$^+$ cells/kg, $1.5 \times 10^5$ CD4$^+$ and/or CD8$^+$ cells/kg, $2 \times 10^5$ CD4$^+$ and/or CD8$^+$ cells/kg, or $1 \times 10^6$ CD4$^+$ and/or CD8$^+$ cells/kg body weight. In some embodiments, the cells are administered at or within a certain range of error of, greater than, and/or at least about $1 \times 10^6$, about $2.5 \times 10^6$, about $5 \times 10^6$, about $7.5 \times 10^6$, or about $9 \times 10^6$ CD4$^+$ cells, and/or at least about $1 \times 10^6$, about $2.5 \times 10^6$, about $5 \times 10^6$, about $7.5 \times 10^6$, or about $9 \times 10^6$ CD8+ cells, and/or at least about $1 \times 10^6$, about $2.5 \times 10^6$, about $5 \times 10^6$, about $7.5 \times 10^6$, or about $9 \times 10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the method includes administrating the cellular engineering target with a toleration range of a desired output ratio of multiple cell populations or sub-types, such as CD4+ and CD8+ cells or sub-types. In some embodiments, the desired ratio is a specific ratio or can be a range of ratios, for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some embodiments, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, the method includes administrating the cellular engineering target a dose of modified cells in a single dose or multiple doses. In some embodiments, administrating the cellular engineering includes multiple doses, e.g., once a week or every 7 days, once every 2 weeks or every 14 days, once every 3 weeks or every 21 days, once every 4 weeks or every 28 days. In an exemplary embodiment, administrating the cellular engineering includes a single dose of modified cells, such as by rapid intravenous infusion.

In some embodiments, for the prevention or treatment of disease, the appropriate dosage depends on the type of disease, the type of cells or recombinant receptors, the severity and course of the disease, whether administrating the cells for preventive or therapeutic purposes, previous therapy, the subject's clinical history and response to the cellular engineering target, and the discretion of the attending physician. In some embodiments, the method includes administrating the compositions and cells once or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In some embodiments, the method includes determining the biological activity of the cellular engineering target, e.g., by any of a number of known methods. In some embodiments, one or more parameters utilized in such a determination include specific binding of an engineered or natural T cell or other immune cell to antigen, in vivo, e.g., by imaging, or ex vivo, e.g., by ELISA or flow cytometry. In certain embodiments, the method includes determining the ability of the engineered cells to destroy target cells using any suitable method known in the art, such as cytotoxicity assays. In certain embodiments, the method includes determining the biological activity of the cells by assaying expression and/or secretion of one or more cytokines, such as CD 107a, IFNy, IL-2, and TNF. In some embodiments, the method includes determining the biological activity by assessing clinical outcome, such as reduction in tumor burden or load.

In some embodiments, the method includes providing a specific dosage regimen that includes a lymphodepletion step prior to the administration of the modified T cells. In an exemplary embodiment, the lymphodepletion step includes administrating cyclophosphamide and/or fludarabine.

In some embodiments, the administrating of lymphodepletion includes administrating cyclophosphamide at a dose of between about 200 mg/m.sup.2/day and about 2000 mg/m.sup.2/day (e.g., 200 mg/m.sup.2/day, 300 mg/m.sup.2/day, or 500 mg/m.sup.2/day). In an exemplary embodiment, the dose of cyclophosphamide is about 300 mg/m.sup.2/day. In some embodiments, the lymphodepletion step includes administration of fludarabine at a dose of between about 20 mg/m.sup.2/day and about 900 mg/m.sup.2/day (e.g., 20 mg/m.sup.2/day, 25 mg/m.sup.2/day, 30 mg/m.sup.2/day, or 60 mg/m.sup.2/day). In an exemplary embodiment, the dose of fludarabine is about 30 mg/m.sup.2/day.

In some embodiment, the administrating of lymphodepletion includes administrating cyclophosphamide at a dose of between about 200 mg/m.sup.2/day and about 2000 mg/m.sup.2/day (e.g., 200 mg/m.sup.2/day, 300 mg/m.sup.2/day, or 500 mg/m.sup.2/day), and fludarabine at a dose of between about 20 mg/m.sup.2/day and about 900 mg/m.sup.2/day (e.g., 20 mg/m.sup.2/day, 25 mg/m.sup.2/day, 30 mg/m.sup.2/day, or 60 mg/m.sup.2/day). In an exemplary embodiment, the administrating of lymphodepletion includes administrating cyclophosphamide at a dose of about 300 mg/m.sup.2/day, and fludarabine at a dose of about 30 mg/m.sup.2/day.

In an exemplary embodiment, a subject has a diagnosis for castrate-resistant prostate cancer, the method includes administrating lymphodepleting chemotherapy prior to administrating of the modified T cellular engineering target. In an exemplary embodiment, for a subject having castrate-resistant prostate cancer, the subject receives lymphodepleting chemotherapy including at or about 500 mg/m.sup.2 to at or about 1 g/m.sup.2 of cyclophosphamide by intravenous infusion. In an exemplary embodiment, for a subject having castrate-resistant prostate cancer, the subject receives lymphodepleting chemotherapy including at or about 500 mg/m.sup.2 to at or about 1 g/m.sup.2 of cyclophosphamide by intravenous infusion about 3 days (.+-0.1 day) prior to administration of the modified T cells. In an exemplary embodiment, for a subject having castrate-resistant prostate cancer, the subject receives lymphodepleting chemotherapy including at or about 500 mg/m.sup.2 to at or about 1 g/m.sup.2 of cyclophosphamide by intravenous infusion up to 4 days prior to administration of the modified T cells. In an exemplary embodiment, for a subject having castrate-resistant prostate cancer, the subject receives lymphodepleting chemotherapy including at or about 500 mg/m.sup.2 to at or about 1 g/m.sup.2 of cyclophosphamide by intravenous infusion 4 days prior to administration of the modified T cells. In an exemplary embodiment, for a subject having castrate-resistant prostate cancer, the subject receives lymphodepleting chemotherapy including at or about 500 mg/m.sup.2 to at or about 1 g/m.sup.2 of cyclophosphamide by intravenous infusion 3 days prior to administration of the modified T cells. In an exemplary embodiment, for a subject having castrate-resistant prostate cancer, the subject receives lymphodepleting chemotherapy including at or about 500 mg/m.sup.2 to at or about 1 g/m.sup.2 of cyclophosphamide by intravenous infusion 2 days prior to administration of the modified T cells.

In an exemplary embodiment, the method includes, a subject having castrate-resistant prostate cancer, administrating lymphodepleting chemotherapy including 300 mg/m.sup.2 of cyclophosphamide by intravenous infusion 3 days prior to administrating the modified T cells. In an exemplary embodiment, for a subject having castrate-resistant prostate cancer, the method includes administrating lymphodepleting chemotherapy including 300 mg/m.sup.2 of cyclophosphamide by intravenous infusion for 3 days prior to administrating the modified T cells.

In an exemplary embodiment, for a subject having castrate-resistant prostate cancer, the method includes administrating lymphodepleting chemotherapy including fludarabine at a dose of between about 20 mg/m.sup.2/day and about 900 mg/m.sup.2/day (e.g., 20 mg/m.sup.2/day, 25 mg/m.sup.2/day, 30 mg/m.sup.2/day, or 60 mg/m.sup.2/day). In an exemplary embodiment, for a subject having castrate-resistant prostate cancer, the method includes administrating lymphodepleting chemotherapy including fludarabine at a dose of 30 mg/m.sup.2 for 3 days.

In an exemplary embodiment, for a subject having castrate-resistant prostate cancer, the method includes administrating lymphodepleting chemotherapy including cyclophosphamide at a dose of between about 200 mg/m.sup.2/day and about 2000 mg/m.sup.2/day (e.g., 200 mg/m.sup.2/day, 300 mg/m.sup.2/day, or 500 mg/m.sup.2/day), and fludarabine at a dose of between about 20 mg/m.sup.2/day and about 900 mg/m.sup.2/day (e.g., 20 mg/m.sup.2/day, 25 mg/m.sup.2/day, 30 mg/m.sup.2/day, or 60 mg/m.sup.2/day). In an exemplary embodiment, for a subject having castrate-resistant prostate cancer, the method includes administrating lymphodepleting chemotherapy including cyclophosphamide at a dose of about 300 mg/m.sup.2/day, and fludarabine at a dose of 30 mg/m.sup.2 for 3 days.

It is known in the art that one of the adverse effects following infusion of CAR T cells is the onset of immune activation, known as cytokine release syndrome (CRS). CRS is immune activation resulting in elevated inflammatory cytokines. Clinical and laboratory measures range from mild CRS (constitutional symptoms and/or grade-2 organ toxicity) to severe CRS (sCRS; grade.gtoreq.3 organ toxicity, aggressive clinical intervention, and/or potentially life threatening). Clinical features include high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the present disclosure provides for, following the diagnosis of CRS, appropriate CRS management strategies that mitigate one or more physiological symptoms of uncontrolled inflammation without dampening the antitumor efficacy of the cellular engineering target (e.g., CAR T cells). CRS management strategies are known in the art. For example, in some embodiments, the method includes administrating systemic corticosteroids to rapidly reverse symptoms of sCRS (e.g., grade 3 CRS) without compromising initial antitumor response.

In some embodiments, the method includes administrating an anti-IL-6R antibody. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administrating of tocilizumab has demonstrated near-immediate reversal of CRS.

In some embodiments, the method includes selecting and treating a subject having failed at least one prior course of standard of cancer therapy. For example, a suitable subject may have had a confirmed diagnosis of relapsed prostate cancer. In some embodiments, the method includes selecting and treating a subject having had at least one prior course of standard of cancer therapy. For example, a suitable subject may have had prior therapy with at least one standard 17.alpha. lyase inhibitor or second-generation anti-androgen therapy for the treatment of metastatic castrate resistant prostate cancer.

In an exemplary embodiment, a suitable subject is a subject having metastatic castrate resistant prostate cancer. In an exemplary embodiment, a suitable subject is a subject having metastatic castrate resistant prostate cancer having .gtoreq.10% tumor cells expressing PSMA as determined by immunohistochemistry analysis on fresh tissue.

In some embodiments, a suitable subject is a subject that has radiographic evidence of osseous metastatic disease and/or quantifiable, non-osseous metastatic disease (nodal or visceral).

In some embodiments, a suitable subject includes an ECOG performance status of 0-1.

In some embodiments, a suitable subject exhibits adequate organ function, as defined by: serum creatinine.ltoreq.1.5 mg/dl or creatinine clearance.gtoreq.60 cc/min; and/or serum total bilirubin<1.5.times.ULN; serum ALT/AST<2.times.ULN.

In some embodiments, a suitable subject exhibits adequate hematologic reserve as defined by: Hgb>10 g/dl; PLT>100 k/ul; and/or ANC>1.5 k/ul.

In some embodiments, a suitable subject is not transfusion dependent.

In some embodiments, a suitable subject is a subject that has evidence of progressive castrate resistant prostate adenocarcinoma, as defined by: castrate levels of testosterone (<50 ng/ml) with or without the use of androgen deprivation therapy; and/or evidence of one of the following measures of progressive disease: soft tissue progression by RECIST 1.1 criteria, osseous disease progression with 2 or more new lesions on bone scan (as per PCWG2 criteria), increase in serum PSA of at least 25% and an absolute increase of 2 ng/ml or more from nadir (as per PCWG2 criteria).

In some embodiments, a suitable subject has had previous treatment with at least one second-generation androgen signaling inhibitor. In some embodiments, a suitable subject has had previous treatment with abiraterone. In some embodiments, a suitable subject has had previous treatment with enzalutamide.

In some embodiments, a suitable subject includes .gtoreq.10% tumor cells expressing PSMA by immunohistochemistry (IHC) on a metastatic tissue biopsy.

In some embodiments, a suitable subject includes radiographic evidence for metastatic disease (osseous or nodal/visceral).

In some embodiments, a suitable subject includes .ltoreq.4 lines of therapy for metastatic CRPC.

Additional details and information regarding the manufacture of cellular engineering targets can be found at U.S. Pat. No. 10,780,120, entitled "Prostate-specific membrane antigen cars and methods of use thereof," filed Mar. 5, 2019; U.S. Pat. No. 10,839,945, entitled "Cell processing method," filed Jul. 6, 2015; U.S. Pat. No. 10,428,351, entitled "Methods for transduction and cell processing," filed Nov. 4, 2015; U.S. Pat. No. 10,877,055, entitled "Parallel cell processing method and facility," filed Jan. 11, 2019, each of which is hereby incorporated by reference in its entirety for all purposes.

Referring to FIG. 2, the computer system 100 is configured to store an instrument library 106 describing a plurality of instruments 52 of a respective modular biological foundry system, 200.

In some embodiments, the server 200 receives the data elements wirelessly through radio-frequency (RF) signals. In some embodiments, such signals are in accordance with an 802.11 (Wi-Fi), Bluetooth, or ZigBee standard.

In some embodiments, the computer system 100 is not proximate to the biological foundry 200 and/or does not have wireless capabilities or such wireless capabilities are not used for the purpose of providing instructions to the instruments 300 of the biological foundry 200. In such embodiments, a communication network 106 is utilized to communicate an update for executing a respective instance of a corresponding compiled workflow from the service to the biological foundry. In some embodiments, the communication network 106 is utilized to communicate a result of a manufacture of a respective cellular engineering target produced at the biological foundry 200 to the computer system 100.

Examples of communication networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 10 other than the one depicted in FIG. 1 are possible. For instance, in some embodiments, rather than relying on a communications network 106, the computer system 100 wirelessly transmits information directly to the biological foundry 200. Further, in some embodiments, the computer system 100 constitutes a portable electronic device, a server computer, or in fact constitute several computers that are linked together in a network or are instantiated as one or virtual machines and/or containers in a cloud-computing context. As such, the exemplary topology shown in FIG. 1 merely serves to describe the features of an embodiment of the present disclosure in a manner that will be readily understood to one of skill in the art.

Additional details and information regarding workflows at a biological foundry system can be found at International Patent Application no.: PCT/US2021/018927, entitled "Systems and Methods for Facilitating Modular and Parallelized Manufacturing at a Biological Foundry," filed Feb. 19, 2021, which is hereby incorporated by reference in its entirety.

Accordingly, one aspect of the present disclosure is directed to providing systems, methods, and apparatuses that facilitates providing a modular biological foundry system. The modular biological foundry system includes a controller and a communications interface that is in electrical communication with the controller. Moreover, the modular biological foundry system includes a plurality of peripheral devices, which in turn includes an articulated handling robot and a power supply. The articulated handling robot is configured to move a cell therapy cartridge between at least a first biological foundry instrument and a second biological foundry instrument in a plurality of biological foundry instruments configured to produce a portion of the one or more cellular engineering targets. The modular system includes a frame surrounding the articulated handling robot. The frame includes at least two modules in a plurality of modules. A first module in the at least two modules is configured to accommodate a respective biological foundry instrument in the plurality of biological foundry instructions. Moreover, each module in the plurality of modules includes a plurality of elongated members. Each module in the plurality of modules further includes a first plurality of coupling mechanisms for coupling at least two elongated members in the plurality of elongated members. Additionally, each module in the plurality of modules includes a second plurality of coupling mechanisms for removably coupling a respective elongated member in the plurality of elongated members with the frame. Furthermore, each module in the plurality of modules includes a plurality of walls engaged with and supported by the at least two elongated members in the plurality of elongated members. Accordingly, the plurality of walls forms an internal volume of a respective module sealed from an environment, such that a modular biological foundry system is provided.

In some embodiments, the modular biological foundry system further includes a transport path coupled to the articulated handling robot and in electrical communication with the communications interface. The transport path extends from a first end portion of a first wall in the plurality of walls to a second end portion of a second wall in the plurality of walls.

Turning to FIG. 3 through FIG. 6 with the foregoing in mind, consider that a manufacturing process for a cellular engineering target is divided into a plurality of steps. In each step, a different manufacturing task or sub-process is carried out. For instance, in some embodiments, the different manufacturing task includes incubation of cell culture, isolation of one or more types of cells, viral transduction, freezing, thawing, etc. Accordingly, the present disclosure provides a modular clean room biological foundry system that utilizes a separate module (e.g., module 208-1 of FIG. 3) to conduct each step of the manufacturing process.

Figure 15:
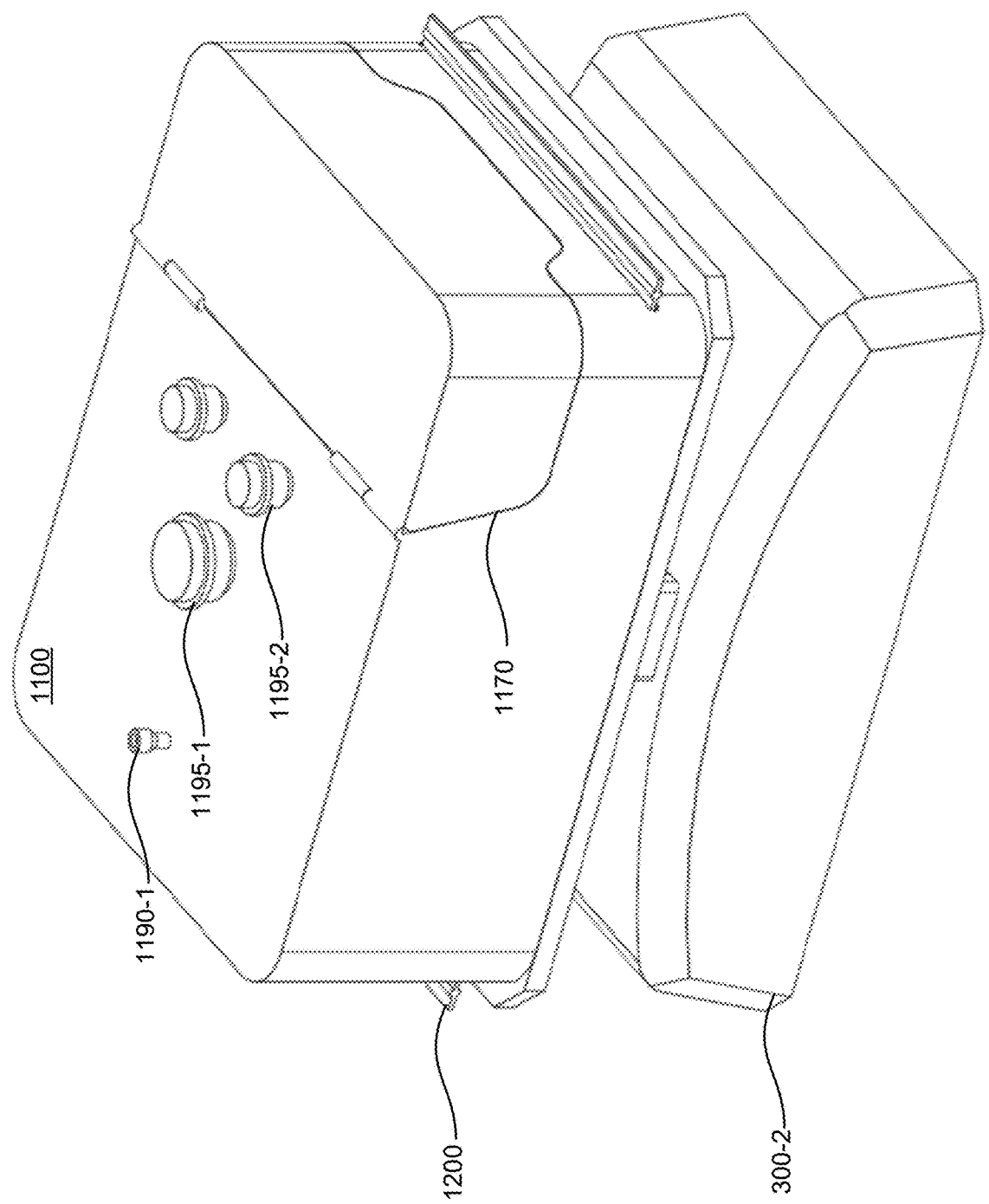
FIG. 15 is another perspective view of a plurality of instruments of a biological foundry including a rigid cartridge, in accordance with an embodiment of the present disclosure.

Each module 208 includes an instrument (e.g., instrument 300 of FIG. 1, instrument 300 of FIG. 7, instrument 300-2 of Figure of FIG. 15, etc.) that performs a particular step (or set of steps) in a cellular engineering target manufacturing process. Accordingly, in some embodiments, each module includes both the instrument that carries out the task, and/or one or more support instruments for that task. Support instruments includes air filtering systems (e.g., air filtering system 220 of FIG. 4), electronic systems (e.g., electronic systems 212 of FIG. 3), processors (e.g., CPU 202 of FIG. 2), cloud connectivity devices (e.g., communications network 106 of FIG. 1), and one or more reservoirs of raw material or waste material of the manufacturing process. A module has a well-defined shape formed through elongated members (e.g., elongated members 216 of FIG. 6), which allows for the module to change positions within the modular biological foundry without requiring modification to the frame of the modular biological foundry system. Accordingly, a plurality of modules, together, realize the manufacturing process for producing a plurality of cellular engineering targets.

Figure 14:
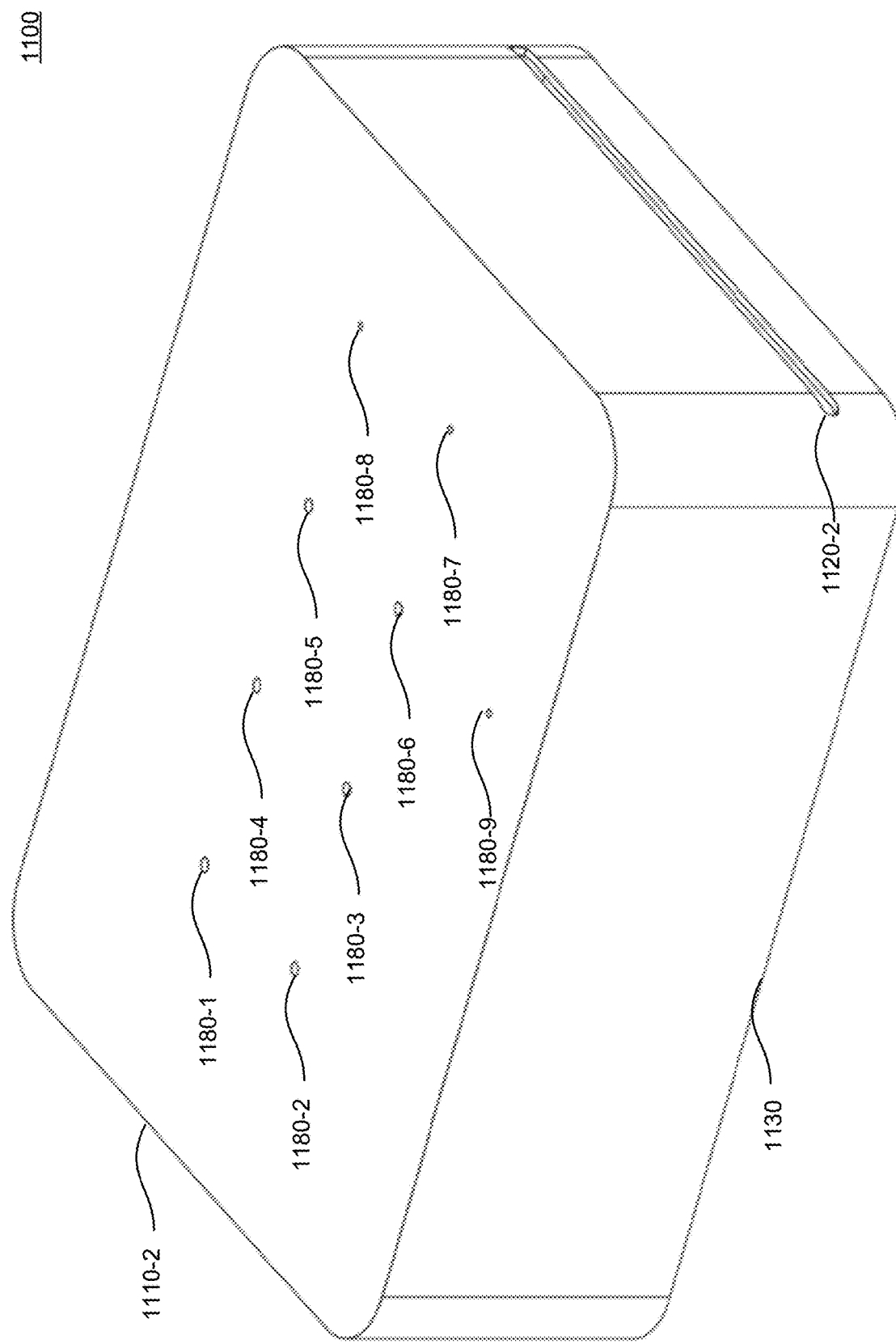
FIG. 14 is a perspective view of a rigid cartridge, in accordance with an embodiment of the present disclosure.

The modular clean room biological foundry system 200 includes a frame (e.g., frame 206 of FIG. 3, frame 206 of FIG. 5, etc.), such that each module 208 removably couples with the frame 206. In some embodiments, the frame is formed from a plurality of elongate members (e.g., elongated members 216 of FIG. 3), such that each elongated member forms an edge of the frame and couples to a different elongated member. In some embodiments, the frame is located in proximity of a robotic material transfer system (e.g., articulated handling robot 202 of FIG. 3, transport path 204 of FIG. 4, etc.) that is able to move a portion of a cellular engineering target, such as a rigid cartridge accommodating the cellular engineering target (e.g., rigid cartridge 1100 of FIG. 14), among the different modules of the modular clean room biological foundry system. For example, when manufacturing a new cellular engineering target, the robotic material transfer system brings a plurality of initial reagents to a first module 208-1 that is necessary for an initial process of the manufacture of the new cellular engineering target. Once the first module has performed its task, the material transfer system moves the cellular manufacturing target to the second module required by the manufacture process. In some embodiments, these steps are repeated (e.g., moving a portion of a cellular engineering target from a first module to a second module of the frame) for each successive task in the manufacture, until the manufacture of the cellular engineering target is complete.

Since this biological foundry system is modular, additional modules 2087 can be added to frame 206 if needed. For example, in some embodiments, additional modules added to the increases production capacity at modular biological foundry system 200. Should a new manufacturing task be required to realize a new or modified cellular engineering target, the modules of the modular biological foundry system allow for adding and/or removing modules in order to facilitating the manufacture of the new or modified cellular engineering targets. Additionally, this modular architecture enables parallel production. Additionally, in some embodiments, unique engineering targets in a plurality of cellular engineering targets can be realized by the modular biological foundry system at the same time, if there are enough individual modules 208 to carry out all the required tasks simultaneously. In some embodiments, one or more buffers is added to the modular biological foundry system, in order to increase the capacity of the modular biological foundry system to manufacture a plurality of cellular engineering targets at the same time.

In some embodiments, modules 208 are placed in frame 206 that is equipped with a plurality of coupling mechanism (e.g., coupling mechanism 216 of FIG. 4) that facilitating holding a respective module in place within the frame. Accordingly, in some embodiments, the frame facilitates accommodating a plurality of modules on a plurality of rows and/or columns of modules. For example, referring briefly to FIG. 5, in some embodiments, two or three modules 208 is stacked vertically and/or horizontally into a plurality of rows and/or columns and supported in place by the frame. This configuration would respectively support two or three times more modules than a configuration with a single column and/or row. In some embodiments, the frame allows accommodating a plurality of module side by side, either along straight lines (e.g. modules are side by side in a row, such as forming a substantially rectangular shape) or along a curved line (e.g. modules are disposed in a substantially circle shape around articulated handling robot 202 and/or transport path 204). In this way, the frame makes it easy to accommodate modules within the frame, add new modules to the frame, and removable couple modules that are no longer needed from the frame, thus providing a modular biological foundry system. Because of the frame, the biological foundry system can be continuously adapted and adjusted by modify a first subset of modules in without affecting a second subset of modules that are not being modified.

Accordingly, in some embodiments, the modular biological foundry system includes the modules, the frame, and the robotic material transfer system (e.g., articulated handling robot, transport path). Moreover, in some embodiments, the biological foundry system includes one or more support instruments (e.g. air filtering and discharge systems 220, electronics 212, power supply, controller, communications interface, etc.) that is included in the modules and/or the frame, or physically attached to them.

Figure 6:
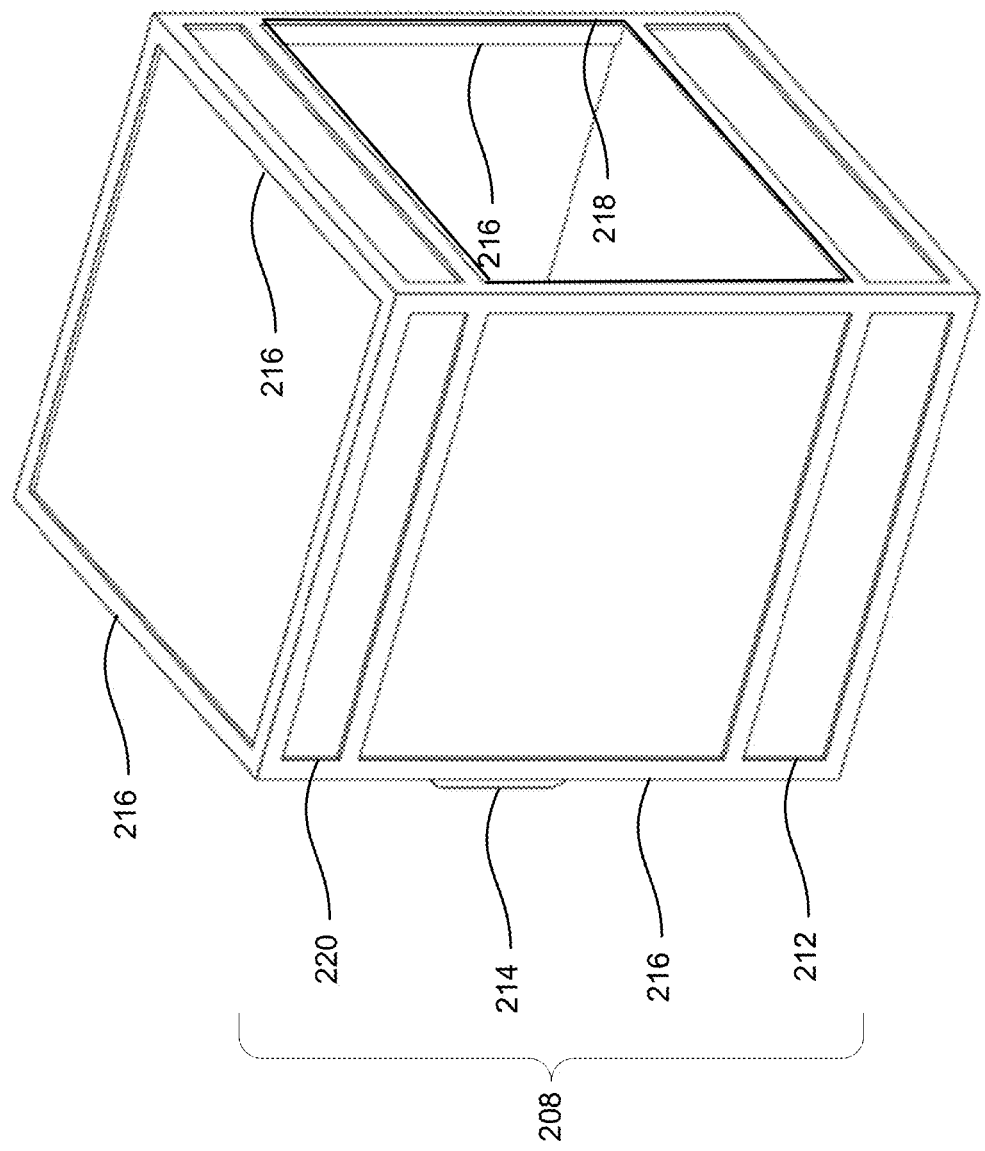
FIG. 6 is a perspective view of a module of a modular clean room biological foundry system, in accordance with an embodiment of the present disclosure.
Figure 13:
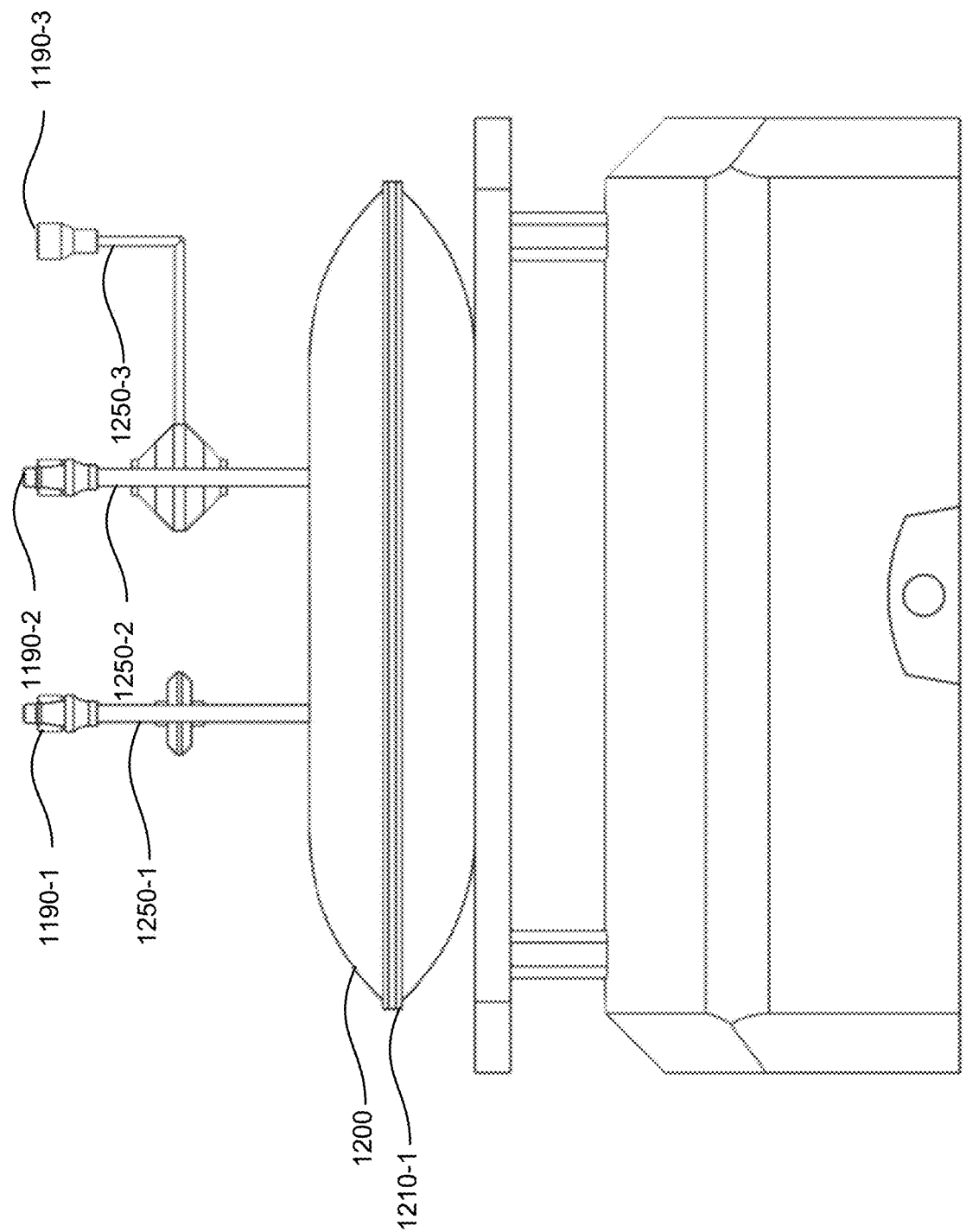
FIG. 13 is a side view of a plurality of instruments of a biological foundry including a soft body bioreactor, in accordance with an embodiment of the present disclosure.

Each module 208 includes an external structure that includes a plurality of elongated members (e.g., elongate members 216 of FIG. 6). Collectively, the plurality of elongated members couple at respective end portions to form an interior of the module that accommodates a corresponding instrument. In this way, the elongated members form the edges of each module 208. The instrument is utilized for carrying out a step (or set of steps) in the manufacture of a cellular engineering target, such as a soft body bioreactor (e.g., soft body bioreactor 1200 of FIG. 13). In some embodiments, this soft body bioreactor is placed inside of a respective module. The respective module will then provide a controlled environment for the soft body bioreactor to operate in, and provide electrical power one or more mechanisms (e.g., sensors) that facilitates obtaining data elements as inputs and/or outputs for the soft body bioreactor. This way, both custom-built and commercially available instruments can be integrated into a respective module of the modular biological foundry system.

In some embodiments, except for a respective instrument 300 accommodated by each module (e.g., instrument that performs a manufacture task), each module shares the same external structure, such that the frame can accommodate each respective module in a plurality of modules at a position of the frame. As used here, an external structure of a respective module is a "shell" of the respective module. Accordingly, the shell provides the respective module with a base platform (e.g., base 230 of FIG. 3), on which an instrument 300 is supported. In addition to providing a base for the respective module, the shell can also provide a plurality support functions that support the biological foundry system and/or instrument of the respective module in the manufacture of cellular engineering targets. These support functions include air filtering systems, air removal systems, power supply, controller(s), computing devices (e.g., computer system 100 of FIG. 2), cloud connectivity devices (e.g., communications network 106 of FIG. 1), or a combination thereof. However, the present disclosure is not limited thereto.

In some embodiments, the shell of the respective module 208 is selected from a group consisting of at least two types of shells, at least three types of shells, at least four types of shells, at least five types of shells, at least ten types of shells, or a combination thereof.

In some embodiments, a shell of a respective module includes a base platform and a plurality of elongated members (e.g., forming a hollow box shell). Each end portion of an elongated member 216 is coupled to another end member of a second elongated member, to form the edges of the module and/or frame. Collective, the elongated members and/or base form the frame. In such embodiments, the shell of the respective module includes a substantially flat base on which an instrument is supported and elongated members that surrounds the instrument on all sides. In some embodiments, a front side of the instrument is exposed, such as module 208-2 of FIG. 3 exposing instrument 300-4 through front side facing articulated robot 202). In such embodiments, the shell of the respective module provides an interior that protects the instrument from all sides except for the front, where it presents an access opening for the robotic material transfer system. This shell type also allows the respective module to be precisely mounted on the frame of the modular biological foundry system. For instance, in some embodiments, the base and/or the elongated members of the respective module is removably coupled to the frame with a coupling mechanism, such as one or more clamps, one or more bolts, or the like.

Figure 5:
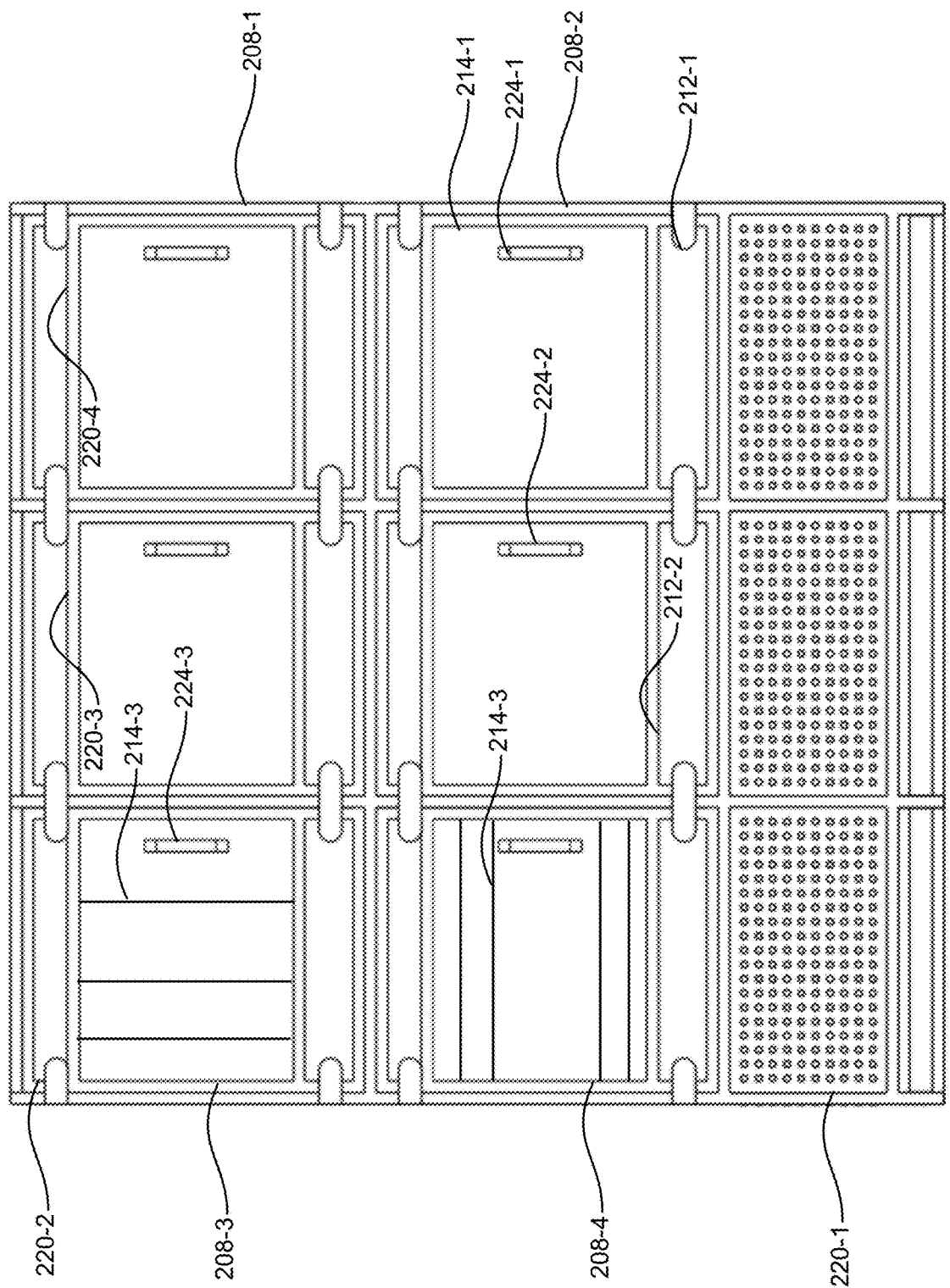
FIG. 5 is a front view of a modular clean room biological foundry system, in accordance with an embodiment of the present disclosure.

In some embodiments, the shell includes an electronics enclosure (e.g., electronic cabinet 212 of FIG. 5). The electronics enclosure includes an interior portion of the respective module that is separated from the rest of the respective module (e.g., by base platform 230). The electronic enclosure provides the interior portion for accommodating a plurality of electronic associated with the instrument and/or biological foundry system, such as controller(s), power supply, and communications network interface (e.g., network interface 284 of FIG. 2). In some embodiments, the electronics enclosure is typically positioned at a bottom end portion of the module below the base platform on which an instrument is accommodated. From this, wires from/to the instrument can be routed through an aperture of the base platform (e.g., with sealed joints), and then reach electronics of the electronics solution. Accordingly, this configuration provides superior ease of assembly and testing, while also protecting electronics from fluids or reagents that could be spilled as a result of a manufacturing and/or cleaning process conducted inside and/or surrounding a module. However, one of skill in the art will appreciate that the present disclosure is not so limited.

For instance, in some embodiments, the shell of the respective module 208 includes an air filtering system 220. The air filtering system provides the respective module with a controlled flow of clean air, and, optionally, removes (e.g., exhaust) waste air from the respective module when needed. In some embodiments, the air filtering system is disposed in an upper end portion of the shell of the respective module. This way, the air filtering system can generate a top-down flow of clean air above an instrument in the respective module, such as a laminar flow of fluid through the modular biological foundry system. In alternative embodiments, the air filtering system is disposed in a lateral portion of the respective module, such that the air filtering system provides a horizontal flow of fluid (e.g., horizontal laminar flow through biological foundry system). In such embodiments, the fluid (e.g., air) that is pushed and/or drawn by the air filtering system exits the respective module through an open side portion of the respective module, such as the front side of the respective module, which is the same opening through which the robotic material transfer system accesses the module. However, the present disclosure is not limited thereto. In some embodiments, the base platform and/or a side portion of the respective module includes a second air filtering system that facilitates waste removal. In some embodiments, the air filtering systems includes one or more perforated side panels coupled to the elongated members of the module, filtering membranes, filtering ducts, louver vents, and the like. One of skill in the art will appreciate that the present disclosure is not so limited. This way, in some embodiments, fluid that is pushed in from an upper end portion of the respective module by the air filtering system is then removed at a bottom end portion of the respective module by the second air filtering system for waste removal. Accordingly, the air filtering system provides a module with a clean room environment, because the fluid inside of the module is filtered and controlled (e.g., by controller 288 of FIG. 2).

As described supra, modules 208 are held in place by frame 206. A structure of the frame makes it simple and quick removably couple modules with the frame. For instance, in some embodiments, modules are slid into the frame with one or more guiding mechanism, such as one or more jigs, one or more linear guides, one or more stoppers, one or more rails, one or more bearings, or the like.

In some embodiments, each respective module includes a sealing mechanism 218, such as a gasket, that creates a seal between an interior of a respective module and the modular biological foundry system. In some embodiments, once a respective module 208 has been disposed at a position within frame 206, the module is then pressed onto a gasket (e.g., gasket 218 of FIG. 6) that is located in front of the module (e.g., open front side of module 208 of FIG. 6). In some embodiments, gasket 218 surrounds a perimeter of a side of a module, such as continuously on the whole perimeter of the front face of the module. In some embodiments, the side of the module including the gasket is the same side where there is an opening that allows the robotic material transfer system access to the interior of the module. In such embodiments, the gasket is positioned around this opening, so that when the module is disposed in the frame, the module is pressed against the gasket and the frame to create a clean-room grade seal between the module and the frame. In other words, if the frame of the modular biological foundry system is a clean room environment, adding a module to the frame and ensuring that the gasket is engaged will not compromise the environmental controls on the clean room of a central space of the modular clean room biological foundry system, such as space 222 of FIG. 4 that accommodates an articulated handling robot 202 and transport path 204. Accordingly, the module that is added to the frame will constitute an addition to the clean room space 222 of the modular biological foundry system without risking contamination to the clean room space and/or other modules of the frame.

In some embodiments, coupling mechanism 216 apply a force to the module 208 against the frame 206, and therefore the gasket 218, connecting the module to the frame in a clean-room-compatible manner. These coupling mechanisms, exerting a force on a rear portion (or on other regions) of the module and pushing the module towards the gasket, include one or more clamps (mechanism 216 of FIG. 4), one or more screws, one or more levers, one or more detent mechanisms, or a combination thereof.

In some embodiments, once module 208 has been connected to frame 206 with sealing mechanism 218, the module can also be removed from the frame without destroying the clean room conditions of the modular biological foundry system. The disposal and removal processes for each module is equally simple and rapid. The module reduces the engineering and retooling costs associated with modifying the configuration of the modular biological foundry system. More modules can be added to the frame when desired or needed. For instance, modules that are no longer useful in the manufacture of a cellular engineering target can be removed from the frame to make room for other modules. If a new manufacturing task needs to be performed, an appropriate new module can be added to the frame. All these operations are executed quickly, without engineering or retooling costs, given the uniformity of the modules and the frame. The result is a flexible manufacturing system (i.e., the modular biological foundry system) that can adapt to different processes and different production scales as needed. This level of flexibility and scalability is impossible with traditional serial production systems, which are "locked in" in the initial configuration.

In some embodiments, each module 208 is separated from frame 206 of modular biological foundry system 200 by a second sealing mechanism (e.g., sealing mechanism 214 of FIG. 5). Sealing off a module from the modular biological foundry system is essential when a module is removed from modular biological foundry system. For example, if a first module malfunctions—or if it must be replaced with a second module different than the first module—it is important to remove the first module without affecting the regular clean-room operational conditions of the modular biological foundry system, such as disturbing a third module and/or a rigid cartridge. This is achieved with second sealing mechanism 214 that is activated before removing the module from the frame. The second sealing mechanism creates a physical barrier between the module and the modular biological foundry system, such as space 222 of FIG. 4. By doing so, the second sealing mechanism ensures that the module to be removed from the frame does not affect the clean room conditions inside the modular biological foundry system.

Figure 4:
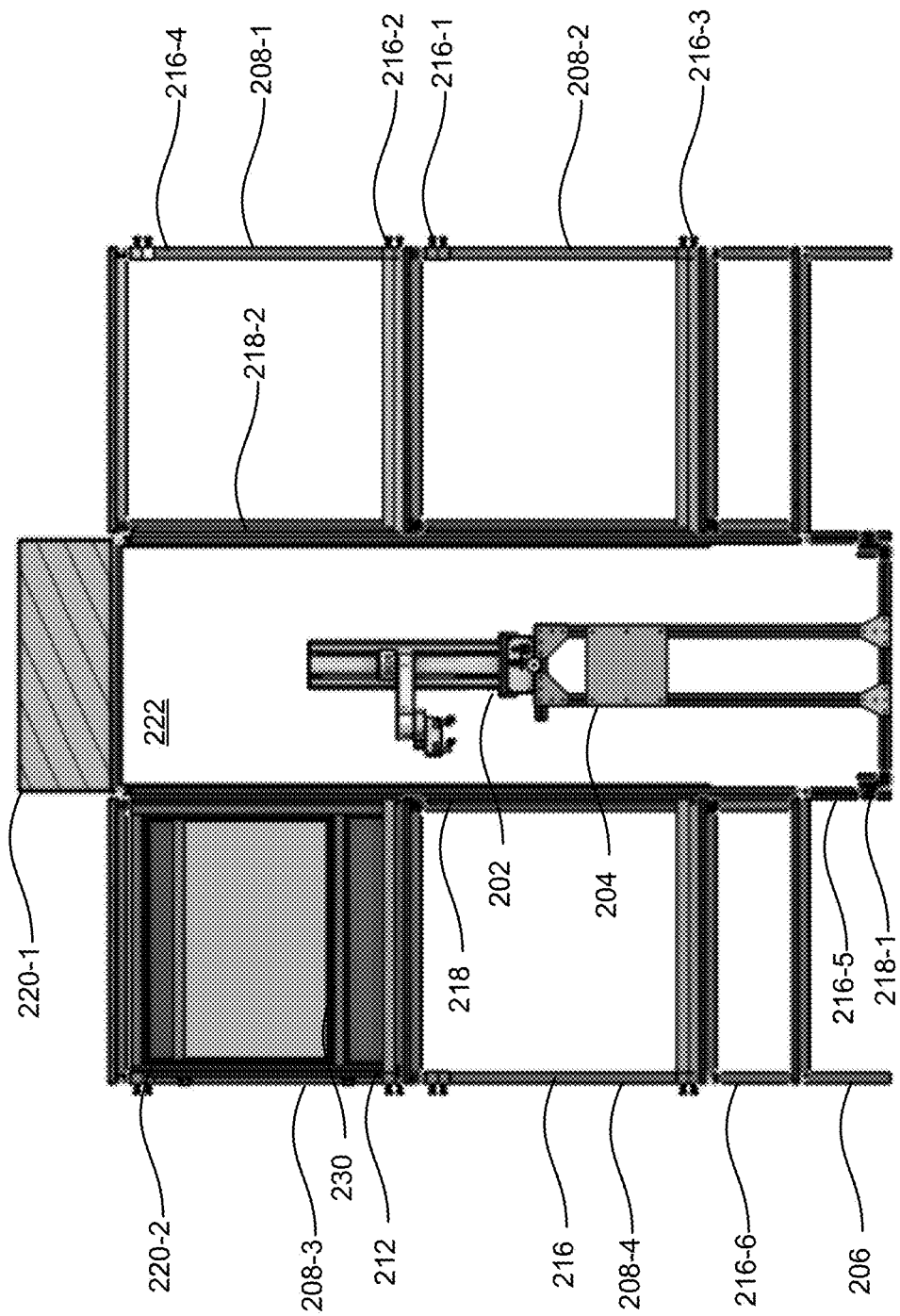
FIG. 4 is a side view of a modular clean room biological foundry, in accordance with an embodiment of the present disclosure.

Second sealing mechanism 214 can be implemented with a variety of embodiments, including a multi-segmented sliding doors mechanism (second sealing mechanism 214 of FIG. 4). This multi-segmented sliding door second sealing mechanism can be easily operated by the robotic material transfer system (e.g. articulated handling robot 202), by sliding an outer segment from one end portion of the module to a second end portion of the module, and opening or closing the second sealing mechanism. Since the sliding door second sealing mechanism is composed of multiple segments, it occupies a limited space when it is folded. The more segments the sliding door has, the less space it occupies in the folded position. However, one of skill in the art will appreciate that the present disclosure is not limited thereto.

By way of example, in some embodiments, second sealing mechanism 214 includes a horizontally oriented sliding door mechanism. For instance, referring briefly to FIG. 5, third module 208-3 includes third second sealing mechanism 214-3 with four horizontal segments. The advantage of this second sealing mechanism is that the robotic material transfer system that operates the second sealing mechanism does not have to work against gravity to open or close the second sealing mechanism.

In some embodiments, second sealing mechanism 214 includes mechanical mechanism 224 that is disposed on an exterior portion of the second sliding mechanism, such as a round knob, a cylindrical knob, a hemispherical knob, a crank, or the like. For instance, referring briefly to FIG. 5, second module 208-2 includes first second sealing mechanism 214-1 that is a door with first mechanical mechanism 224-1 that is a handle protruding outwardly from an exterior surface of the first second sealing mechanism). This includes mechanical mechanism enables the robotic material transfer system to easily operate the second sealing mechanism without exerting unwanted torques. For example, the robotic material transfer system could feature a manipulator shaped like a hollow tube, such as a hollow tube including a lead-in edge including a chamfer on the edge of an inner hole of the hollow tube. This manipulator can be easily positioned around the circular knob, enabling the robotic material transfer system to open and close the second sealing mechanism and access the interior of the module.

In alternative embodiments, second sealing mechanism 214 include a sliding door mechanism that opens and closes by sliding in a vertical direction. For instance, referring briefly to FIG. 5, fourth module 208-4 includes third second sealing mechanism 214-3 that includes four vertical segments. This vertical second sealing mechanism is advantageous if, in its folded position, it substantially overlaps with a region of the module other than an opening used to access the interior of the module by the robotic material transfer system, such as electronics enclosure 212 and/or air filtering mechanism 220. This way, the opening in the front of the module would be larger when the sliding mechanism is folded.

In some embodiments, second sealing mechanism 214 includes a rigid panel that removably couples to frame 206 and/or module 208. For instance, in some embodiments, the second sealing mechanism includes magnetic locks that couple to the frame of modular biological foundry system 200, such as in front of an opening of the module that is accessed by robotic material transfer system 202. Accordingly, the robotic material transfer system (e.g. an articulated handling robot) can handling the second sealing mechanism that is a rigid panel and separate the interior of the module from the modular biological foundry system with the rigid panel when it is necessary to separate a respective module from the modular biological foundry system. In some embodiments, the second sealing mechanisms sealing is stored inside the modular biological foundry system, so that the robotic material transfer system can rapidly pick one second sealing mechanism and use the second sealing mechanisms to seal a respective module whenever such sealing is needed.

In some embodiments, the second sealing mechanisms 214 includes one or more rolling door mechanisms, one or more pivoting door mechanisms, one or more multi-segmented pivoting door mechanisms, sliding panel mechanisms that can slide over one or more modules, and the like.

In some embodiments, a rear portion of module 208 there is an access mechanism that allows an operator to access the module for maintenance and to perform manual operations, such as installing instrument 300 within an interior of the module. For instance, in some embodiments, the access mechanism includes a door. In some embodiments, the rear portion of the module includes one or more spaces, or apertures, to insert or remove rigid cartridges 1100.

In some embodiments, rigid cartridge 1100 is utilized to store a material utilized in the manufacture of a cellular engineering target, such as cell culture media, reagents, pharmaceutical ingredients, etc.). In some embodiments, the cartridge is initially an empty container that will then accommodate a material, such as waste material produced as an instrument accommodated by the module performs a manufacturing task. Accordingly, the presence of apertures that facilitate accommodating cartridges on the rear end portion of the module allows a user to insert new cartridges and remove old cartridges from the apertures without affecting the sterility or the clean-room conditions inside the module and the rest of the modular biological foundry system. In some embodiments, the apertures are the rear end portion of the module include physical barrier that separates an external environment (e.g., atmosphere) from the interior of the module. In some embodiments, the rear of the module includes a plurality of ports and/or a plurality of valves that is accommodated by the apertures, which allows the modular biological foundry system to connect an interior of the cartridge with the instrument in the module, such as once the cartridge has been removably coupled with a respective aperture at the rear end portion of the module. These ports and/or valves enable a sterile connection between the cartridge and the instrument of the module, such that a cartridge replacement process at a respective module is performed without any external fluids (e.g., atmospheric air) or contaminants entering the module. A user outside of the modular biological foundry system can add and remove the cartridges, without affecting or compromising the clean-room conditions inside of the module and the modular biological foundry system.

The modules are placed within frame 206. The frame is a rigid structure that accommodates the modules 208. In some embodiments, the frame includes a plurality of beams, a plurality of planar or substantially planar surfaces, one or more sealing mechanisms (e.g., sealing mechanism 218), one or more second sealing mechanisms 224, one or more conduits for wires and the like, one or more electronic systems accommodated by electronics enclosure 212, one or more air filtering mechanisms 220, or a combination thereof. One of skill in the art will appreciate that any other feature or sub-system that is necessary to support the operation of the modules within the modular biological foundry system is within the domain of the present disclosure. In this way, the frame keeps the modules in a fixed, pre-determined position within the modular biological foundry system 200. In this way, each module and/or instrument is associated with a fixed address (e.g., address of instrument 108 of FIG. 2, address of module 112 of FIG. 2, which is used by the robotic material transfer system for spatial determinations when moving the cartridge. In some embodiments, the frame includes electrical power and/or network interface connectivity for communicating with computer system 100 over communications network 106. In this way, the frame allows the modules to operate into a shared clean-room environment, where the manufacturing process to produce the cellular engineering targets can be carried out in a sterile manner.

The frame can host multiple rows of modules 208 and multiple columns of modules 208. For instance, in some embodiments, the frame includes an arrangement of modules 208 in which the modules are placed in a straight line, in a rectangle, in a circle, or any other straight or curvilinear shape (e.g., an open shape, a closed shape, or a combination of both open and closed shapes).

In some embodiments, modular biological foundry system 200 includes multiple frames 206 that are placed side by side, creating aisles or groups of frames 206. In some embodiments, each aisle or group of frames 206 includes a unique transport path and/or articulated handling robot. In other embodiments, the aisles or groups of frames 206 share one or more transport paths and/or articulated handling robot. For instance, in such embodiments, a single robot material transfer system can facilitate conducting the manufacture of cellular engineering targets are each instrument 300 of each module 208 of each aisle or groups of frames 206 while moving one or more cartridges 1100 between each instrument 300 or each module 208.

In some embodiments, besides accommodating modules 208, frame 206 includes one or more solid side walls or panels that seal an interior of the modular biological foundry system from an environment. In this way, the solid side walls provide a self-contained clean room that is completely isolated from the outside environment. Each module 208 interfaces with this clean room environment of the frame through an opening on a front end portion of a module. In some embodiments, the open front end portion of the module is sealable, in case the module needs to be removed, such as by the sealing mechanism 214, 224 described supra. Inside the frame, the whole environment is controlled (i.e. it's a sterile clean room). And, inside the frame, there are only robotic systems. No human operator is present within the modular biological foundry system while the system is in operation. This ensures the efficiency of the system and prevents external sources of contamination (including human operators) from affecting the process.

In some embodiments, a lower end portion of frame 206 includes an enclosure that hosts the electronic systems providing power and network connectivity to all the modules hosted in the frame. In some embodiments, an upper end portion of the frame includes air filtering mechanism 220 (e.g., air filtering mechanism 220 of FIG. 4), which ensures that the environment provided by the modular biological foundry system where the robotic material transfer system operates (between the various modules of the frame) is clean-room grade and sterile. In some embodiments, in the bottom part of the vertical walls of the frame there are discharge filters, which allow the air at the bottom of the modular biological foundry system to exit—while the higher internal pressure prevents external air from infiltrating modular biological foundry system. The whole volume that is included inside the frame and the modules is completely closed off from the external environment. This allows the modular biological foundry system to operate as an independent clean room within an external environment that might have a lower level of control.

In some embodiments, at a lower end portion of frame 206, a sealing mechanism, such as a gasket, ensures that there is a seal between the elongated members of the frame that accommodate the modules and a base (e.g., transport path 204) that supports the robotic material transfer system. In some embodiments, this sealing mechanism is a gasket (e.g., gasket 218 of FIG. 6) between a lower end portion of the frame (which optionally includes the modules) and the base structure of the robotic material transport system. This way, the frame and the robotic material transfer system can be designed as separate systems and assembled in place. Additionally, the sealing mechanism at the lower end portion of the frame ensures that the lower end portion of the modular biological foundry system is completely sealed off from an environment, such that here is a continuous separation between the interior space 222 of the modular biological foundry system and the environment where the modular biological foundry system is located.

In some embodiments, the modular biological foundry system is not only protected from external air infiltrating it. It is also protected, at the level of the production floor, from cleaning liquids or reagents infiltrating it. For example, when manufacturing operators mop the production floor, the gasketed structure of the bottom of the modular biological foundry system prevents that splashes or drops of cleaning liquids infiltrate the internal clean-room environment.

In some embodiments, the frame makes it possible to isolate the internal clean-room environment of the modular biological foundry system from the external environment. This means that the modular biological foundry system can be placed (and operated) in lower-grade clean rooms, while guaranteeing that the cells are manufactured in highly controlled, sterile conditions.

In some embodiments, the frame provides an area of about 100 square feet (sq. ft.), of about 150 sq. ft., about 160 sq. ft., about 175 sq. ft., about 200 sq. ft., about 250 sq. ft., about 300 sq. ft., about 350 sq. ft., about 400 sq. ft., about 450 sq. ft., about 500 sq. ft., about 550 sq. ft., about 600 sq. ft., about 650 sq. ft., about 700 sq. ft., about 750 sq. ft., about 850 sq. ft., about 950 sq. ft., about 1000 sq. ft., or about 1,500 sq. ft. In some embodiments, a height of the frame is about 3 feet (ft), about 4 feet, about 5 feet, about 6 feet, about 7 feet, about 8 feet, about 9 feet, about 10 feet, about 11 feet, or about 12 feet. In some embodiments, a width of the frame is about 5 feet, about 6 feet, about 8 feet, about 10 feet, about 12 feet, about 14 feet, about 16 feet, about 18 feet, about 20 feet, about 24 feet, about 28 feet, about 32 feet (e.g., 33 feet). However, the present disclosure is not limited thereto.

Additionally, in some embodiments, creating an isolated production space inside the modular biological foundry system enables the use of a wide range of systems to enforce sterility. These systems can be employed because, within the modular biological foundry system, there are no human operators. Therefore, sterilization and cleaning systems that would be dangerous for human operators can be used inside of the modular biological foundry system, while the frame makes sure that they are included in the controlled environment. This protects the manufacturing personnel that operate outside the modular biological foundry system, while ensuring superior sterility inside the modular biological foundry system.

In some embodiments, automatic systems to ensure the sterility of the clean-room environment inside the modular biological foundry system include, but are not limited to, the use of: gases (like ozone or $CO_2$), ultraviolet light, chemical cleaning agents (sprayed or in liquid form), radiation, extreme temperatures (high or low), etc. Multiple sterilization techniques can also be applied at the same time, or at different times during the same manufacturing process. In all cases, the fact that the frame isolates the inside of the modular biological foundry system from the outside allows the system to resort to the most appropriate sterilization techniques, without endangering the human operators.

A further advantage is that these cleaning methods can be executed by a robotic arm or by another automatic system within the modular biological foundry system. This ensures that the cleaning/sterilization procedures are executed in a repeatable, measurable, and validated manner.

In some embodiments, the manufacturing process of a cellular manufacturing target is completed by moving each cellular manufacturing target t from one module to the next, so that each machine can perform its task on the cellular manufacturing target. Note that, in the context on individualized medicine, the size of a batch is one—meaning that each batch includes only one product, because each cellular manufacturing target is different from the others. This robotic manufacturing architecture is very efficient when managing small batches, i.e. batches composed of a few products. The limit case is that a batch includes a single product. Batches that include a few identical products can also be managed easily, by "entraining" a set of products that are manufactured one after the other by the same sequence of modules.

In all module and batch configurations, it is essential to have a robotic material transfer system that moves the products between the different modules of the modular biological foundry system. The robotic material transfer system accesses each module through an opening in the front side of the module. A wide range of robotic material transfer systems can be used in modular biological foundry system, including but not limited to: a robotic arm on a rail, a robotic gantry, a conveyor belt system, a magnetic rail system, a wheeled robot moving on the floor, a legged robot, an aerial robot, etc. In some embodiments, the robotic material transfer system includes a flexure gripping device (e.g., included as a hand of an articulated handling robot 202). Additional details and information regarding a flexure gripping device can be found at U.S. Pat. No. 10,773,392, entitled "Flexure Gripping Device," filed Mar. 7, 2019, which is hereby incorporated by reference in its entirety.

In some embodiments, a plurality of robotic material transfer systems is disposed within modular biological foundry system 200. For example, in some embodiments, the robotic material transfer systems includes a conveyor belt (e.g., coupled to a side portion of frame 206) that can be used to quickly supply reagents and the, such as while an articulated handling robot performs operations within modules 208 that is less frequent or less predictable. In some embodiments, computer system 100 allows for utilizing different robot material transfer systems for various payloads. As a non-limiting example, in some embodiments, a first articulated handling robot 202-1 is utilized to transport small and/or lighter items (e.g., rigid cartridge 1100 of FIG. 18C), whereas a second articulated handling robot 202-4 is utilized to transport larger and/or heavier items. This flexibility in the robotic material transfer system is particularly relevant for a manufacture of cellular engineering targets, where, in some embodiments, by adding a media to sustain a cellular growth, a batch of cellular engineering targets can start from a few milliliters in volume and increase in volume up to several liters of liquid material. Additionally, in some embodiments, a plurality of robotic material transfer systems is combined to provide increased throughput when manufacturing cellular engineering targets at the modular biological foundry system. For example, in some embodiments, a first material transport system (e.g., a first articulated handling robot and/or first conveyor belt) and a second material transport system (e.g., a second articulated handling robot and/or second conveyor belt) provides more throughput for the modular biological foundry system than just using a single robotic material transfer system.

Since the modular biological foundry system is a completely closed off clean room, in some embodiments, the modular biological foundry system includes a gate mechanism to receive input material and to output finished products. In some embodiments, this gate system includes dedicated, automatic airlock. In such embodiments, the airlock of the gate is the only point of the modular biological foundry system where input materials can be inserted, and output products (finished cellular engineering targets or quality control samples) can be extracted.

In some embodiments, the airlock gate mechanism includes but not limited to a double-door mechanism (e.g., a first door and a second door each provide access to an interior of the gate mechanism). In this embodiment, a user can open an external door of the gate mechanism and place an input product inside of the interior. In some embodiments, the external door is then locked via a locking mechanism, such as a hatch or a key. In some embodiments, each door includes a sealing mechanism, such as a gasket 218, to ensure a clean room environment. However, the present disclosure is not limited thereto. In some embodiments, the modular biological foundry system determines that the external door is locked (e.g., via vision system, via light gate, via sensor, etc.,), a decontamination routine is performed that prepares the product (and the environment that surrounds the product in the airlock, such as the interior of the gate mechanism) to be inserted into the clean-room environment of the modular biological foundry system. In some embodiments, once the decontamination routine is completed, the modular biological foundry system autonomously opens the internal door of the airlock, and the robotic material transfer system is then able to retrieve the input product. In some embodiments, as a final step of the operation cycle, for the airlock gate mechanism, is represented by automatically closing the internal door. In some embodiments, this cycle is repeated in the opposite order when there are cellular engineering targets that need to be extracted from the modular biological foundry system—like completed cellular engineering targets or samples for quality control. When cellular engineering targets (e.g., rigid cartridge including cellular engineering targets) are extracted from the modular biological foundry system, the decontamination cycle begins only after the external door of the airlock gate mechanism has been opened and then closed. Accordingly, in some embodiments, the aforementioned decontamination process follows contact with the external environment, since the internal environment of the modular biological foundry system is already controlled and sterile by air filtering system 220 and sealing mechanism 214, 218, 224.

In some embodiments, since no human user is inside the airlock gate mechanism when both of the doors are locked, it is possible for the modular biological foundry system to use the same decontamination process that can be applied inside of the modular biological foundry system. For instance, because the airlock gate mechanism is separated from the external environment, these decontamination process do not pose a danger to the human user, who are outside of the modular biological foundry system and the airlock gate mechanisms when the modular biological foundry system and the airlock gate mechanisms are in operation.

In some embodiments, material can be inserted into the modular biological foundry system or extracted out of the modular biological foundry through the rigid cartridges that can be placed in the rear end portion of each module 208. However, in such embodiments, this approach based on the cartridges is used to provide raw materials and to remove waste materials from a respective module. In this way, in such embodiments, the rigid cartridges are supporting tasks and materials that might be needed by the modules as they perform the manufacturing tasks on the products. However, the only point of the system that allows for the passage of full products (either at the initial stage—before starting the process—or when they are completed) is the airlock system. The airlock system also allows for the passage of sampling containers or vials, which are used to extract samples for the products inside the modular biological foundry systems. Once extracted from modular biological foundry system, these samples can then be separately analyzed by human operators within a laboratory.

The vials or containers (e.g., rigid cartridges) including product samples can also be transferred to the external environment via a separate, smaller, high-throughput airlock. This is possible because the vials including these samples are small, and their flow is unidirectional (they are always coming from the inside of the modular biological foundry system and going outside). Lots of clean, sterile, unused sampling vials or containers can be supplied to the modular biological foundry system through special cartridges that can be inserted in a module without compromising the clean-room qualification of the modular biological foundry system.

Inside the airlock system, a docking station enables the human operators to place the input materials in a fixed and well-controlled position, so that they can be easily and repeatably picked up by the robotic material transfer system. The docking station also enables the robotic material transfer system to deposit outgoing products and quality control samples, so that they can be retrieved by the human operators outside of the modular biological foundry system.

Cell manufacturing processes are often characterized by unbalanced production steps. In other words, some steps in the cell manufacturing process take a significantly longer amount of time than the others. Consequently, some of the machines that are involved in a cell manufacturing process have cycle times that are longer than the cycle times of the other machines. For example, bioreactors typically require days (or even weeks) to complete cellular growth, while centrifuges are used for process steps that typically take only a few hours. This creates an unbalanced process and makes the use of production lines (e.g., serial production architectures) structurally inefficient for cellular manufacturing applications.

The modular structure of the modular biological foundry system compensates for this imbalance by offering the possibility to add multiple "slow" modules in parallel. An example is a modular biological foundry system including multiple (dozens, or even hundreds) bioreactor modules that work in parallel. This way, while an individual bioreactor module remains slow (the underlying process task has not changed, and the cells take the same time to grow), the overall cycle time of the modular biological foundry system is greatly reduced—proportionally to the number of bioreactor modules that are working in parallel. The possibility to overcome production bottlenecks by adding multiple modules in parallel is a significant advantage of the parallel structure of the modular biological foundry system. Only parallel systems can quickly address unbalanced production steps by increasing the number of "slow" machines. Note that this does not require any additional engineering cost or retooling time—the additional modules are simply mounted in the frame of the modular biological foundry system (which has been designed for this purpose), easily addressing the production bottleneck.

This modular biological foundry system architecture can also be employed to create groups of modules that coordinate their operations. For example, within a cell manufacturing modular biological foundry system, it is possible to create a group of "fast" modules that are operated by a fast robotic arm (i.e. the products are transferred between them by a rapid robotic material transfer system). This group of fast modules is composed of modules that, for example, can each perform their manufacturing task in less than two hours. In this example, the overall cycle time of the group of fast modules is no longer than 2 hours. And this group of fast modules includes a single unit for each type of module. Since all the modules contained in this group are fast, it is not necessary to duplicate them in order to increase their average cycle time.

The group of fast modules described in this example can be paired, within the same modular biological foundry system, with a group of "slow" modules. The slow modules (which are typically, but not exclusively, bioreactor modules) take much longer to complete their task. For example, a bioreactor might need 1 day to complete its task within the cell manufacturing process. In this case, the systems and methods of the present disclosure would need to include 12 bioreactor modules in the group of "slow" modules, so that their average cycle time is reduced to the same 2 hours cycle time that characterizes the fast modules. In this configuration, the group of fast modules (include only a first module for each fast module type) continuously feeds new batches to a large group of slow modules (including multiple modules for each slow module type). Each time a slow module is empty (because it has completed its task), the fast modules feed it with a new batch. The group of slow modules is operated by a larger, slower robotic arm (i.e. a robotic material transfer system with higher payload and lower speed). This material transfer system can be slower because it needs to deposit a batch in each position, and then leave it there for a long time, while the slow task is being completed. And this material transfer system can also be larger (i.e. with a higher payload) because, especially in the case of bioreactors, the volume of the product increases with time. Cells need more media as they grow, so the final size of the batch (at the end of the bioreactor step) can be of several liters (as opposed to less than a liter at the beginning of that manufacturing step). Therefore, the slow robotic arm managing the bioreactors might need a higher payload than the fast robotic arm managing the fast modules.

The architecture of the modular biological foundry system also allows for more modules and more robotic arms to be added when needed. By adding more modules and more robotic material transfer systems, it is possible to increase the throughput of the modular biological foundry system, making the process more rapid and more efficient.

The modular structure of the modular biological foundry system (where each individual module is mounted to the frame and can be separated by a sealing system) allows to take any module offline in case there is a failure maintenance is needed. In other words, if a module fails or needs to be serviced, it can be taken offline by sealing the door on its front side and by removing it from the frame. This does not affect the sterility or the clean room state of the rest of the modular biological foundry system, because the door (i.e. the sealing system) guarantees the physical separation between the module that is removed and the rest of the modular biological foundry system. This makes this parallel structure fault tolerant. Adding more modules not only increases efficiency, but also decreases the risk of overall failure of the modular biological foundry system (by increasing redundancy).

Once new modules that have a better performance for a given task become available, it is possible to add them to the modular biological foundry system without redesigning, modifying or affecting the rest of the system. For example, it is possible to add modules that are faster at performing a given task, if R&D activities develop such modules, or if better machines are commercially available. Likewise, it is possible to add to the modular biological foundry systems modules that are more reliable than the previous ones. These new modules can simply be added to the frame of the modular biological foundry system, without costly and time-consuming redesign processes.

Figure 9:
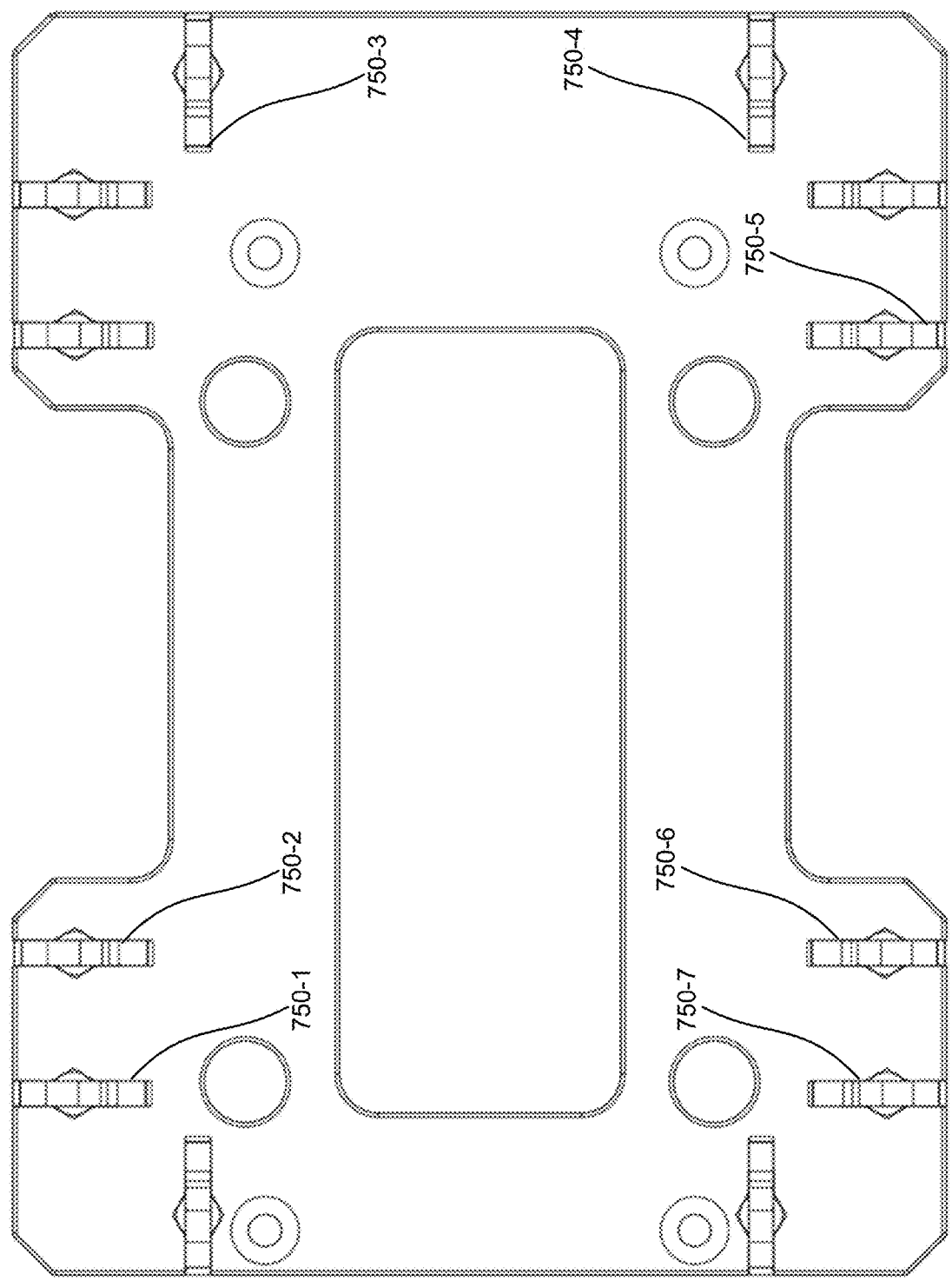
FIG. 9 is a top view of a docking device instrument, in accordance with an embodiment of the present disclosure.
Figure 10:
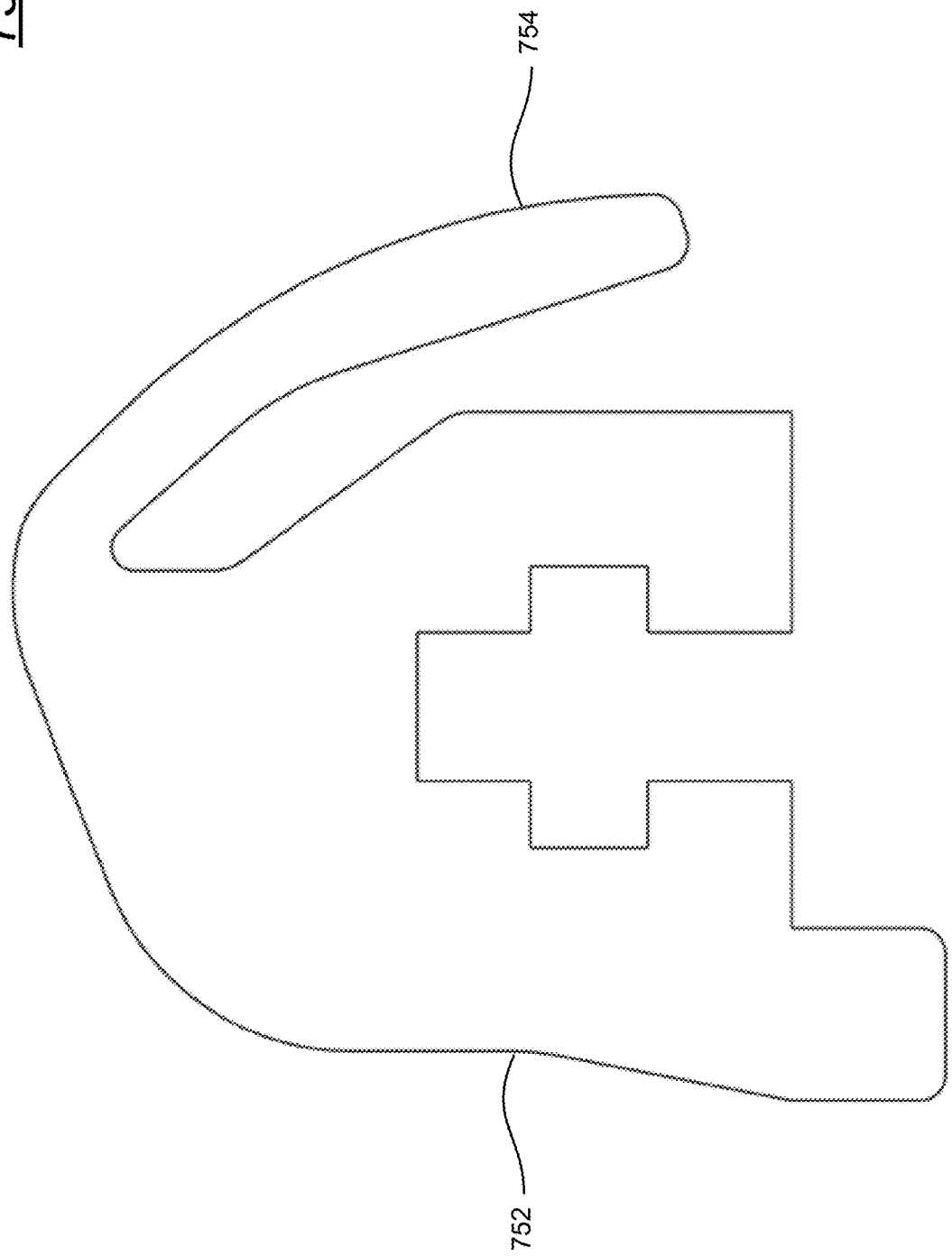
FIG. 10 is a side view of an engagement member of a docking device instrument, in accordance with an embodiment of the present disclosure.

It is also possible to add modules that are different than the previously installed modules. For example, it might be necessary to expand the manufacturing process by adding modules that incorporate new technologies. In the cell manufacturing space, and example of an upgrade of this kind might be represented by adding and electroporation module—replacing (or paired with) a previously used viral transduction module for the genetic engineering step of the cell manufacturing process. This extreme flexibility means that the modular biological foundry system is process-agnostic. By accepting new modules—which might be completely different from the previous ones—the modular biological foundry system can quickly adapt to new processes and start producing new kinds of therapies. FIG. 9 shows an extreme example of this flexibility, in which the same modular biological foundry system architecture can be used to manufacture two completely different types of pharmaceutical products (cell therapies and personalized capsules, in this example). The two processes, which have no manufacturing steps in common, can be implemented simply by mounting on the frame of the modular biological foundry system the right set of manufacturing modules. The manufacturing modules are completely different for the two modular biological foundry systems shown in the example in FIG. 9, but the overall modular structure of the modular biological foundry system is the same.

This also means that, while a therapy is under development, the modular biological foundry system has the flexibility to upgrade and improve the process by modifying its steps and their sequence. Modifications and upgrades like these do not require engineering or retooling costs (beyond building the modules that will be added). The system that is already in place is not affected by the additions. This flexibility is extremely important in the cell manufacturing space, because these manufacturing processes frequently evolve together with the clinical development of the therapies. It is therefore advantageous not to tie down the design of the process to the original choice of modules, which might turn out to be sub-optimal as the drug advances in its clinical path. The flexibility of the modular biological foundry system overcomes this limitation of state-of-the-art manufacturing systems.

Within the modular biological foundry system, the order of the manufacturing operations to be performed on a given batch can be changed simply by instructing the robotic material transfer system to modify the sequence of modules by which a batch will be processed. This makes iterating on the process sequence and parameters very simple, both on the hardware side (i.e. the machines used to perform the process can be changed) and on the software side (i.e. the instructions used to perform the process can be changed, and their order can be changed).

The modular structure of the modular biological foundry system also makes it very easy to achieve industrial scale (i.e. high, efficient throughput) once the first modular biological foundry system has been optimized. In this case, scaling is as easy as building new modular biological foundry systems, each identical to the first one. The structure of the modular biological foundry system is extremely modular, so it is very easy to build and assemble additional clusters, and each one will have the same performance of the first one, because all processes are completely automated. In other words, the fully automated (no labor-associated variability) and modular (easy-to-assemble, easy-to-deploy systems) nature of the modular biological foundry system makes it ideal to rapidly increase the production capacity for cell therapy products.

Additionally, since the modules and the robots are tightly packed inside modular biological foundry system, this manufacturing architecture requires much less space than a traditional labor-based approach. Within a modular biological foundry system there are only machines (no need to leave space for humans), and the modules can be stacked in vertical rows (further increasing machine density and production floor utilization). This results into a very high space efficiency when manufacturing cell therapies with the modular biological foundry system. A single modular biological foundry system occupies about 200 sq. ft., which is much less than a traditional labor-based cell manufacturing suite (which occupies about 1,000 sq. ft.). Moreover, the modular biological foundry system can realize N product simultaneously (where N is the number of units of the slowest module inside modular biological foundry system—usually the bioreactor module). Conversely, a traditional labor-based cell manufacturing suite can only manufacture one cellular manufacturing target at a time (to avoid the risk of mix-ups, human operators can only manage one batch).

Therefore, modular biological foundry systems are not only more efficient than traditional labor-based systems in terms of time and unit economics. They are also more efficient in terms of space. This is very important, because cell manufacturing processes require advanced clean rooms, which are very expensive (per square foot). This makes achieving industrial scale with modular biological foundry systems economically more convenient also from the point of view of the capital investments necessary to build cell manufacturing facilities.

Yet another aspect of the present disclosure is directed to providing a docking device (e.g., docking device instrument) for receiving a portable cell therapy cartridge. The docking device includes a base including a substantially planar upper surface. The substantially planar upper surface is configured to support a lower surface of a portable cell therapy cartridge. The docking device further includes an array of a plurality of engagement members. Each engagement member protrudes upwardly from the substantially planar upper surface of the base. Moreover, each engagement member in the array of the plurality of engagement members includes a fixed body protruding upwardly from the substantially planar upper surface of the base. Additionally, each engagement member in the array of the plurality of engagement members includes a spring integrally formed with the fixed body and extending inwardly from an upper end portion of the fixed body oblique to both the substantially planar upper surface of the base and the fixed body. From this, a deformable gap is formed interposing between a surface of the fixed body and a lower end surface of the spring. Accordingly, an upper end surface of the spring is configured to engage a surface of the portable cell therapy.

Referring to FIG. 7 through FIG. 10, a docking device instrument 300-1 is provided. Each docking device utilizes passive compliance and self-aligning features of engagement members 750. In some embodiments, since a manufacture of cellular engineering targets is automated (e.g., without human interference) from an initial input to a final output, it is important to keep a portion of the cellular engineering target, which are inside of rigid cartridges, or other containers, in place before the portion of the cellular engineering target is picked up by the robotic material transfer system, and, similarly, after the portion of the cellular engineering target is disposed (e.g., retrieved from interior of first module 208-1 and placed inside interior of second module 208-2). For instance, in some embodiments, the portion of the cellular engineering targets must be kept substantially stationary within a module, while an instrument accommodated by the module performs various manufacturing tasks to produce the cellular engineering targets. Accordingly, precise and repeatable positioning of instruments and regents within the modular biological foundry system 300 is achieved by using a docking device 300 that incorporates passive elastic and damping features via engagement members 750.

The docking device instrument utilized by a modular biological foundry system combines a positional accuracy of afforded pins with a tolerance to dimensional errors that is yielded by chamfers. This is achieved with elastic springs (e.g., spring 754 of FIG. 10) that deform when a rigid cartridge is inserted, keeping the rigid cartridge in place and aligning a position of the rigid cartridge based on corresponding positions of an array of the engagement members, such as automatically and passively centering the rigid cartridge on a substantially planar upper surface of a base of the docking device. Since these engagement members elastic and passive, they are extremely robust and do not require special maintenance to function properly. Moreover, since the engagement members are designed to operate in an elastic region of a material of the engagement members, the engagement members tolerate a very high number of cycles of engaging with the rigid cartridge.

By using an array of engagement members 750 all around the cartridge, the position of the rigid cartridge is self-aligned even if an articulated robot 202 deposits the rigid cartridge on the docking device off-center. Accordingly, when there is a positioning error in the placement of the rigid cartridge, springs 754 of engagement members 750 on one side of the docking device would be more compressed than the other engagement members n an opposing side of the docking device. From this, these compressed engagement members would push the rigid cartridge with more force, moving the rigid cartridge towards a center of the docking device, until the force exerted by the spring of each engagement member in the array of engagement members is balanced. This passive load-balancing process ensures that the docking device is self-aligning, in that the springs of the engagement members always pushes an instrument deposited into the docking device towards a center of the docking device, such as a central axis or a center of the array of engagement members. As a result, the docking device autonomously (and passively) eliminates any positioning error that might be resulting from the motion of the articulated handling robot and/or transport path of the modular biological foundry system.

Another advantage of the docking device of the present disclosure is that the spring of engagement members push against an instrument received by the docking device. This way, the springs of engagement members also exert forces along directions that are perpendicular to gravity. Therefore, the instrument received by the docking device is secured in place until the instrument is taken by the articulated handling robot. The additional forces exerted by engagement members of the docking device on the docked part make the docking device robust to vibrational forces and to external forces that are not in the direction of gravity. Moreover, since the docking device provides passive engagement members that do not require any external power (e.g., mechanical power and/or electrical power), nor a active control systems, the docking device of the present disclosure is fault-tolerant and keeps the instrument received by the docking device in place even in case of a power outage at a modular biological foundry system.

In some embodiments, engagement members 750 are disposed along a perimeter (e.g., contour) of an upper end portion and/or side portion of the docking device. In some embodiments, each engagement member of the docking device has a uniform shape, such that the engagement members are faster and cheaper to manufacture. Additionally, in some embodiments, each engagement member is removably coupled to the base of the docking device, which allows for modularity of the engagement member makes it possible to include any number of engagement members as needed to a docking device. For instance, in some embodiments, the array of engagement members includes at least 3 engagement members, at least 4 engagement members, at least 5 engagement members, at least 6 engagement members, at least 7 engagement members, at least 8 engagement members, at least 9 engagement members, at least 10 engagement members, at least 11 engagement members, at least 12 engagement members, at least 13 engagement members, at least 14 engagement members, at least 15 engagement members. However, the present disclosure is not limited thereto. Additional engagement members 750 will result into a stronger gripping force exerted on the instrument received by the docking device. Moreover, using a plurality of engagement members allows the docking device to adapt to any shape of instrument. For instance, in some embodiments, the array of engagement members is configured such that the docketing device is suitable for receiving an instrument that has a prismatic shape, such as an instrument including a substantially planar base of any shape extruded vertically. However, the present disclosure is not limited thereto. For instance, in some embodiments, the array of engagement members allows for receiving an instrument having a complex shape, which is completely secured in the docking device by the springs of the engagement members. Accordingly, the docking device can securely hold instruments with very complex base shapes. In some embodiments, these base shapes of the instruments received by the docking device can even include cavities (e.g., voids), convex profiles (e.g., a lower surface of the instrument has a convex curvature), irregularities, one or more curvilinear edges, or a combination thereof.

Yet another aspect of the present disclosure is directed to providing a rigid cartridge. The rigid cartridge includes a plurality of rigid walls defining a fixed interior. The plurality of rigid walls includes a plurality of rigid side walls. At least two adjacent edges in a plurality of edges formed by the plurality rigid side walls includes a radius of curvature greater than zero. A substantially planar upper rigid wall connected to an upper edge portion of each rigid side wall in the plurality of rigid side walls. The substantially planar upper rigid wall includes a plurality of apertures. Each respective aperture in the plurality of apertures is configured to receive and fixedly engage a corresponding connector which is a member of a group consisting of at least three connectors. Moreover, each respective connector in the at least three connectors provides communication with a corresponding port in a plurality of ports of the soft body bioreactor. Each respective aperture in a first subset of apertures in the plurality of apertures is encompassed by a corresponding annular hood protruding upwardly from the substantially planar upper rigid wall by a first height greater than or equal to a second height of the corresponding connector of the at least three connectors and integrally formed with the substantially planar upper rigid wall. Additionally, the plurality of apertures includes the first subset of apertures. Each respective aperture in the first subset of apertures is configured to receive and fixedly engage a fluidic connector of the at least three connectors configured to provide fluidic communication with at least a first port in the plurality of ports of the soft body bioreactor, and a second subset of apertures. Furthermore, each respective aperture in the second subset of apertures is configured to receive and fixedly engage an electrical connector of the at least three connectors configured to provide electrical communication with at least a second port in the plurality of ports of the soft body bioreactor. The rigid cartridge further includes a seamless lip defined by a lower edge portion of each rigid side wall in the plurality of rigid side walls. Each interior surface in a pair of opposing interior surfaces of two rigid side walls in the plurality of rigid side walls includes a respective first mating mechanism configured to engage a corresponding second mating mechanism of the soft body bioreactor, such that a pair of opposing end portions of the soft body bioreactor is removably coupled with the rigid cartridge.

Figure 11:
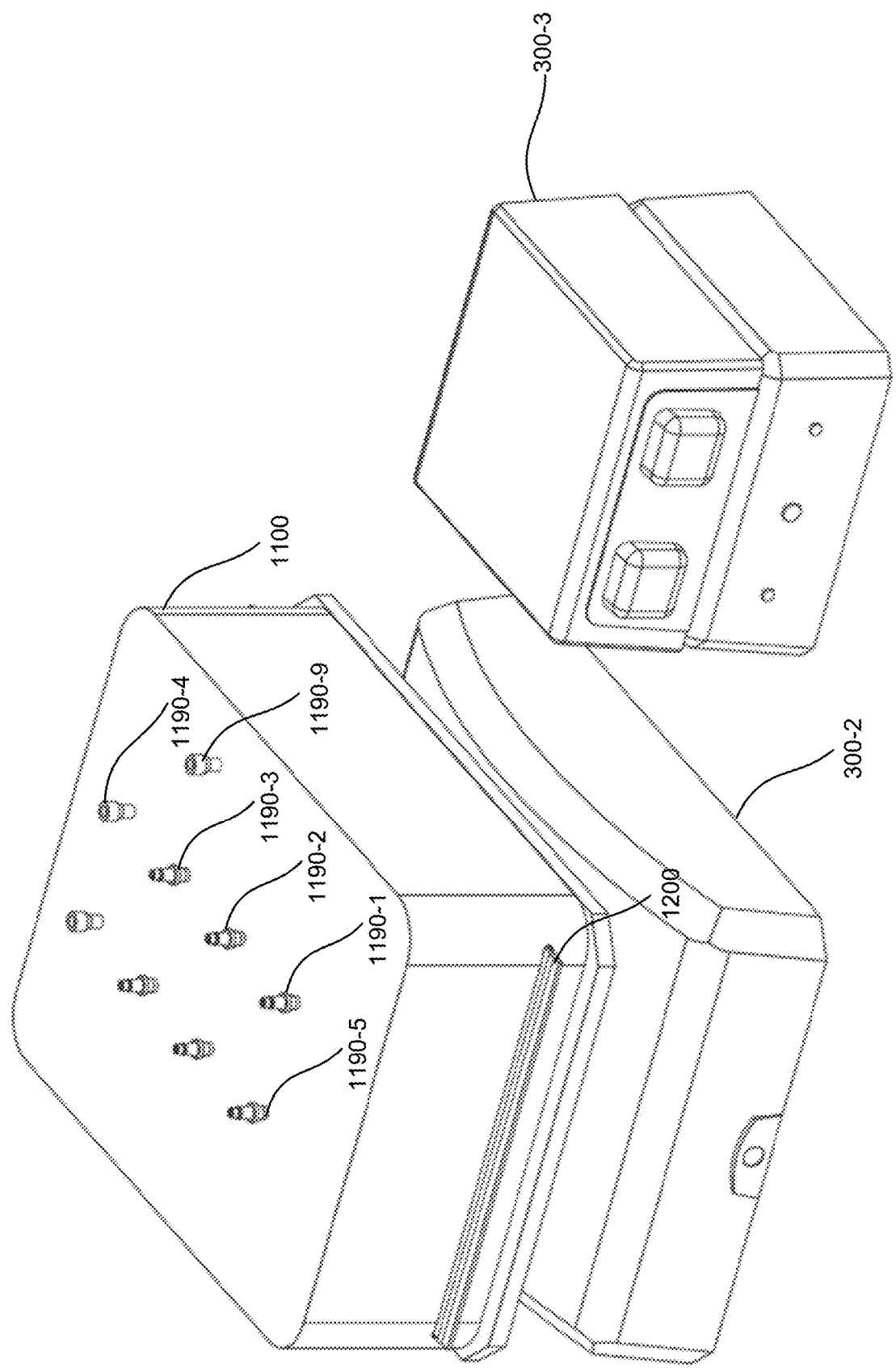
FIG. 11 is a perspective view of a plurality of instruments of a biological foundry including a rigid cartridge, in accordance with an embodiment of the present disclosure.
Figure 12:
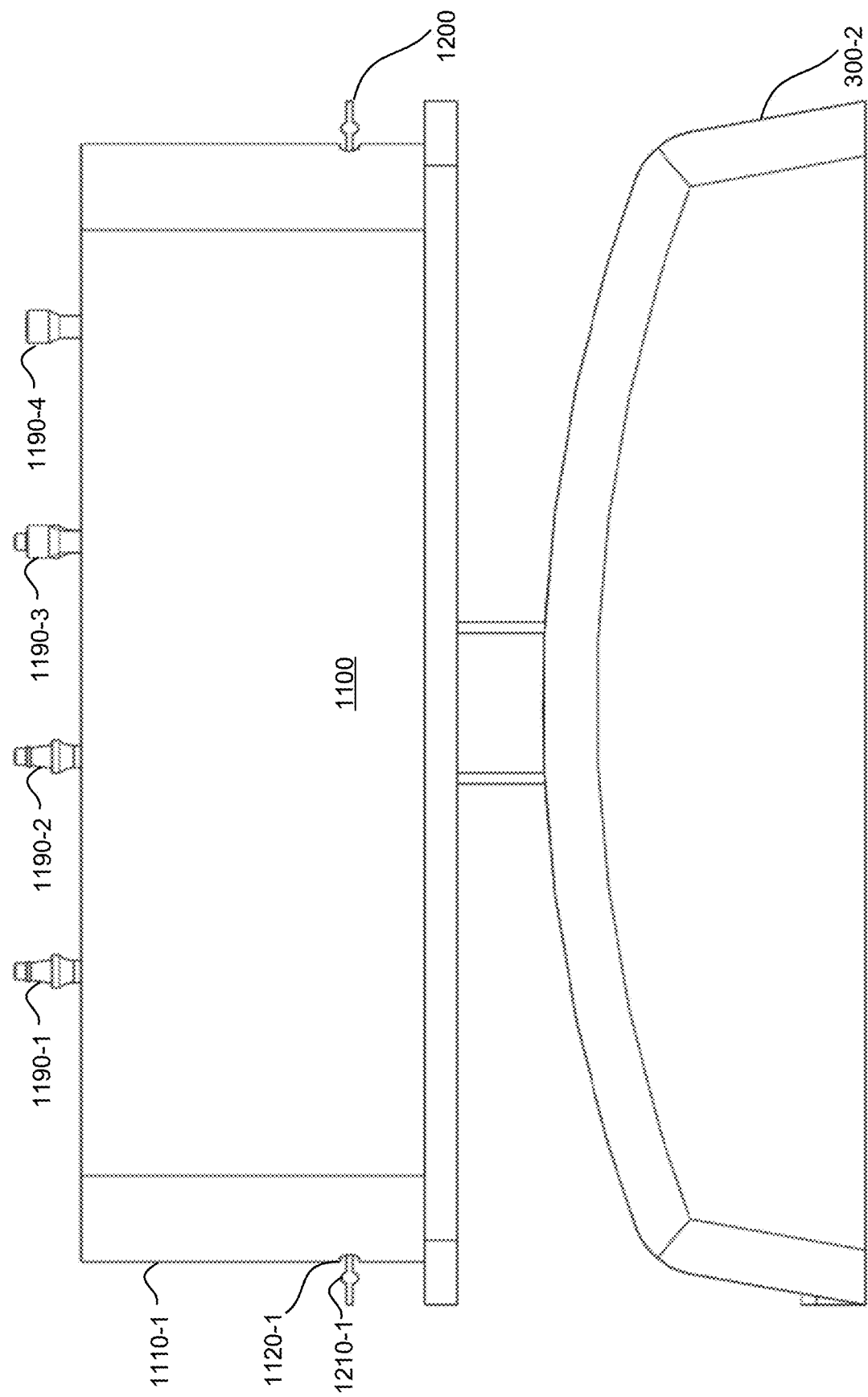
FIG. 12 is a side view of a plurality of instruments of a biological foundry including a rigid cartridge, in accordance with an embodiment of the present disclosure.

Referring to FIG. 12 through FIG. 24, a variety of rigid cartridge (e.g., instrument 300-1 of FIG. 11 are provided, which facilitates sampling of a cellular engineering targeted accommodated by a rigid cartridge and/or a soft body bioreactor, which is performed automatically by articulated handing robot 204 within the modular biological foundry system. Accordingly, the rigid cartridges of the present disclosure provides repeatability of automatic systems that ensures consistency of manufacture of a cellular engineering target since a sample is taken in the same way, such that multiple samples can be effectively compared, and the variations reflect variations in the cellular engineering target (and not variations in the operators' sampling procedures). This makes it easier and safer to ensure and control the quality of the cellular engineering target.

Specifically, rigid cartridge 1100 includes rigid walls 1110 that define a fixed interior. In some embodiments, fixed interior of rigid walls 1110 is utilized to store a portion of a cellular engineering target 2 manufactured by biological foundry system (e.g., rigid cartridge of FIG. 18C). In alternative embodiments, the fixed interior of the rigid walls accommodates a soft body bioreactor that accommodates the cellular engineering target, such as soft body bioreactor 1220 of FIG. 12. In this way, the rigid side walls protect the fixed interior of the rigid cartridge (e.g., from contamination and/or external forces, such as an articulated handling robot). Edges formed by the rigid side walls includes a radius of curvature greater than zero, which provided rounded or chamfered edges, allowing for an articulated handing robot to grasp the exterior of the rigid walls of the rigid cartridge device when the articulated handing robot is not accurate and/or precise in locating the rigid cartridge device.

Furthermore, in some embodiments, the rigid cartridge 1100 includes substantially planar upper rigid wall 1110-2 that is connected to an upper edge portion of each rigid side wall. The substantially planar upper rigid wall includes apertures (e.g., apertures 1180 of FIG. 14). Each respective aperture 1180 is configured to receive and fixedly engage a corresponding connector (e.g., connectors 1190 of FIG. 15), which allows for communication with the interior of the rigid cartridge. For instance, each respective connector provides communication with a corresponding port in a plurality of ports of the soft body bioreactor. However, the present disclosure is not limited thereto.

Figure 18A:
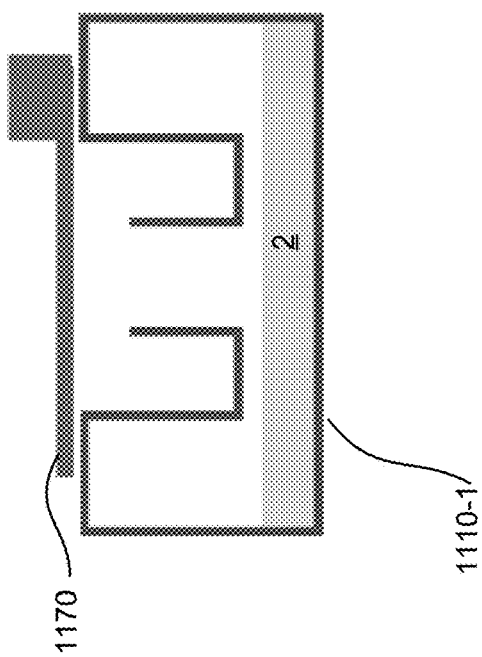
FIG. 18A is a side view of another rigid cartridge, in accordance with an embodiment of the present disclosure.
Figure 18B:
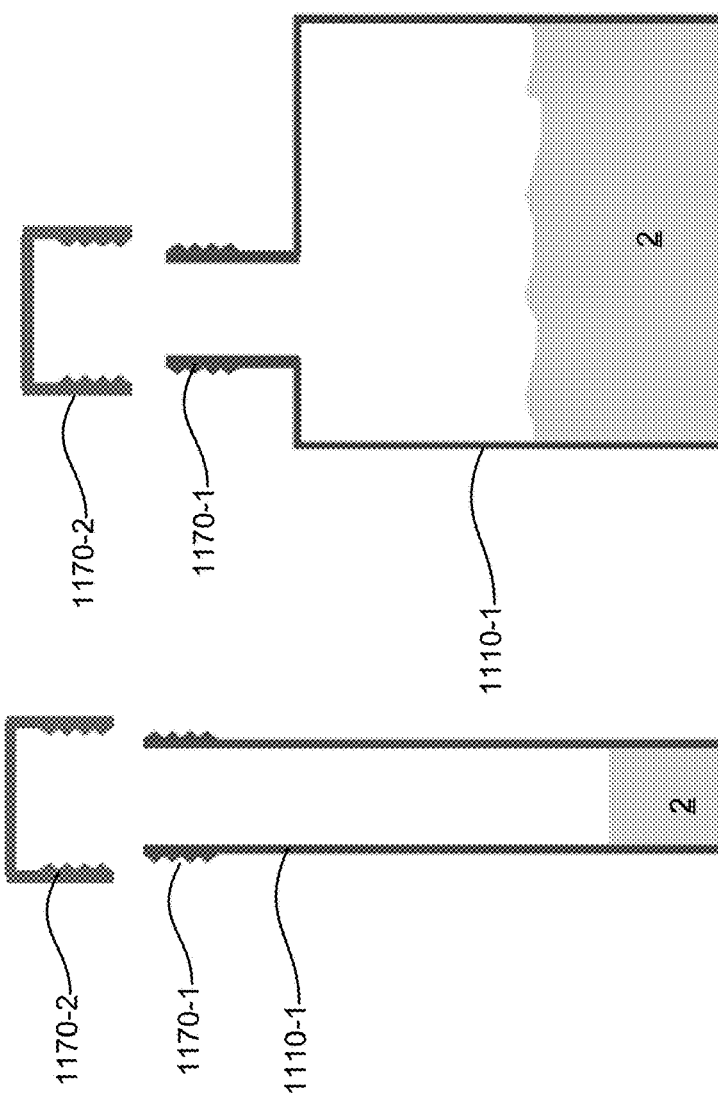
FIG. 18B is a side view of yet another rigid cartridge, in accordance with an embodiment of the present disclosure.

For instance, referring briefly to FIGS. 18A and 18B, a variety of rigid cartridges 1100 of a modular biological foundry system are provided. Each rigid cartridge 1100 accommodates a portion of an engineering target (e.g., a cell therapy cellular manufacturing target in liquid form) that must be sampled and/or transferred between rigid cartridges. Accordingly, each rigid cartridge includes rigid walls 1110 that define a fixed interior for accommodating a portion of a cellular engineering target.

In some embodiments, rigid cartridge 1100 includes aperture 1180 that engages connector 1190 that forms a sampling port. The sampling port connector 1190 allows for an external sampling system of biological foundry system access to the cellular engineering target accommodated by the rigid cartridge. In some embodiments, the sampling port connector 1190 is separated from the external environment by a gate mechanism (e.g., gate mechanisms 1170 of FIG. 18C). In some embodiments, gate mechanism 1170 provides a sterile sealing mechanism, such as a cap. Accordingly, in accordance with a determination of an instruction (e.g., communicate via communications network 106 from computer system 100 of FIG. 1) executing a sampling procedure, articulated handling robot 202 opens the gate mechanism 1170, accesses the sampling port connector 1190, and removes a sample of the cellular engineering target accommodated inside the rigid cartridge. However, the present disclosure is not limited thereto. For instance, in some embodiments, the sample removal operation is performed with a sampling container (e.g. a bin, a container, a spoon, etc.), with a vacuum-based mechanism (e.g. a syringe, a pipette, etc.) or with another mechanism that allows for removal of a part of a cellular engineering target accommodated inside the rigid cartridge. After the articulated handling robot has retrieved a sample of the cellular engineering target, the articulated handling robot deposits the sample inside of a sampling container (e.g. a vial, a flask, a petri dish, etc.), such as a second rigid cartridge configured as a sampling container. The sampling container rigid cartridge includes a similar sampling port connector and a gate mechanism. Accordingly, in some embodiments, after the sample has been deposited into the sampling container rigid cartridge, the dealing system is activated (or put in place), and the sampling container is ready to be delivered to the quality control operators through the airlock system of the modular biological foundry system.

Accordingly, articulated handling robot 202 is able to autonomously execute one or more operations in coordination with rigid cartridge 110 including, opening gate mechanism 1170, accessing connectors 1190 including sampling port connectors, removing a sample of a cellular engineering target from an interior of a first rigid cartridge, depositing the sample into an interior of a second rigid cartridge, disconnecting from the connectors 1190, and closing the gate mechanism 1190. However, one of skill in the art will appreciate that the present disclosure is not limited thereto. In some embodiments, one or more (e.g., all) of these operations is executed automatically (e.g., via computer system 100 in communication with articulated handling robot 202 and transport path 202), and in a sterile manner, within the clean-room environment of the modular biological foundry system.

In some embodiments, a rigid cartridge 1100 includes a consumable mechanism (e.g., non-reusable mechanism, such as a perforated seal), ingredient, or reagent that is used during a sampling process. Accordingly, in some embodiments, the consumable mechanism of the rigid cartridge is then autonomously disposed of by the robotic system of the modular biological foundry system. The disposal of consumable is also executed in an automatic and sterile manner. For example, consumables can be deposited by the robotic systems into a waste cartridge. Once the waste rigid cartridge is full, it is can be safely removed by a manufacturing operator from the outside of the modular biological foundry system. Both removing full waste cartridges and replacing them with empty waste cartridges are operations that are executed without affecting the clean-room, sterile conditions inside the modular biological foundry system. The waste cartridge can be equipped with its own sealing system, in order to isolate the waste material from the rest of the modular biological foundry system.

In some embodiments, the rigid walls of the rigid cartridge include includes polylactic acid (PLA), acrylonitrile butadiene styrene (ABS), polyethylene terephthalate (PET), PET glycol-modified (PETG), polyethylene cotrimethylene terephthalate (PETT), thermoplastic elastomer (TPE), thermoplastic polyurethane (TPU), thermoplastic copolyester (TPC), nylon, polycarbonate (PC), brass, copper, bronze, aluminum, or iron.

The automatic sampling approach also enables a user of computer system 100 to schedule a collection of samples of cellular engineering targets from multiple rigid cartridges 1100. In some embodiments, the collection of samples is scheduled remotely from the modular biological foundry system (e.g., through the communications network 106 that oversees a manufacture of cellular engineering targets at the modular biological foundry system). In such embodiments, the robotic material transfer system collects the samples from a subset of cellular engineering targets defined by the computer system manufacturing at the modular biological foundry system and place each respective sample into a separate and sealed rigid cartridge. The rigid cartridges including the samples are then placed into a mechanism, such as a track, a tray, a pallet, or the like that is stored inside the modular biological foundry system (e.g., portion of frame 206), until all the samples requested by the computer system have been collected by the robotic material transfer system. From this, the robotic material transfer system moves the rigid cartridges including the sample rack into the airlock system (e.g., first and/or second sealing mechanisms 214, 224), where a user at the modular biological foundry system can retrieve the collection of samples (e.g., on the rack) and then bring the collection of samples to an analytical lab where quality control operations are performed on the collection of samples, and similar operations. This way, a user of the computer system 100 can schedule a collection of samples and request an analyze of the collection of samples remotely from the modular biological foundry system. Moreover, in such embodiments, a user enters the modular biological foundry system once, in order to retrieve the collection of samples stored by the sealed rigid cartridges that have been prepared by the robotic material transfer system. This approach to the collection of samples via rigid cartridges 1100 and the robotic material transfer system minimizes a risk for contamination of cellular engineering targets manufactured at the modular biological foundry system and allows users to minimize time spent inside the modular biological foundry system.

Figure 18C:
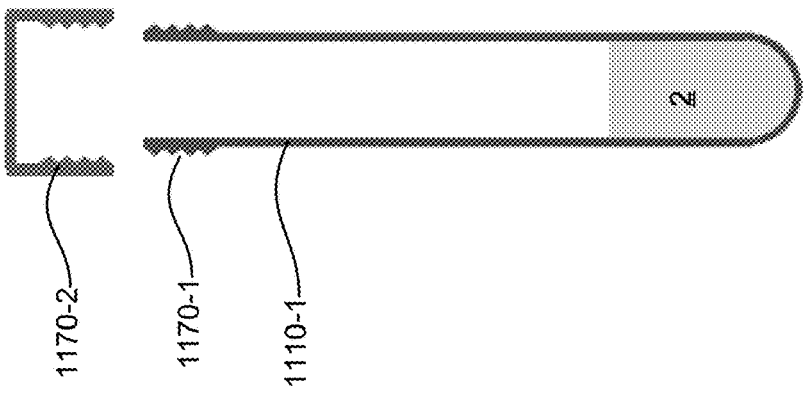
FIG. 18C is a side view of yet another rigid cartridge, in accordance with an embodiment of the present disclosure.

Referring to FIGS. 18B and 18C, various embodiments configurations for gate mechanism 1170 of rigid cartridge 1100 are provided, such as to facilitate a sampling port to access a cellular engineering target accommodated within an interior of the rigid cartridge. In some embodiments, the gate mechanism includes a thread, such as a thread on an interior surface of the gate mechanism (e.g., thread 1170-1) or an external thread, which allows for the gate mechanism to form a seal sealed with a threaded cap (e.g, gate mechanism 1170-2 of FIG. 18B). In such embodiments, the robotic material transfer system can grasp and removably couple the gate mechanism (e.g, screws/unscrews the cap 1170-2) when obtaining a sample of a cellular engineering target accommodated by an interior of the rigid cartridge. Referring to FIG. 18C, in some embodiments, the gate mechanism includes a sliding gate mechanism, such as a thread less sliding gate. Accordingly, the game mechanism includes at least an open position, which permits access to the interior of the rigid cartridge, and a closed position, which prevents access to the interior of the rigid cartridge. In some embodiments, when the gate mechanism is in the closed position, a sealing mechanism (e.g., sealing mechanism 218) ensures that a region around the gate mechanism remains sterile and sealed from an external environment when collecting a sample of a cellular engineering target from the interior of the rigid cartridge mechanism. In some embodiments, the sliding gate mechanism includes a spring that engages at a first end portion of the gate mechanism, which forces the gate mechanism towards a closed position and/or remain stationary. Accordingly, in such embodiments, if the robotic material transfer system needs to open the sealing mechanism, the robotic material transfer system can push or pull on a protruding feature located (e.g., handle 214 of FIG. 6) on the gate mechanism. A force exerted by the robotic material transfer system on the protruding feature of the gate mechanism will open the sealing mechanism, providing the robotic material transfer system with access to the interior of the rigid cartridge, and thus the cellular engineering target. Accordingly, in some embodiments, once an operation for collection of the sample of the cellular engineering target is deemed complete, the robotic material transfer system retracts (e.g., from the interior of the rigid cartridge and/or from applying the force on the protruding feature. In some embodiments, such action by the robotic material transfer system causes the spring to push the gate mechanism back in the closed configuration. In some embodiments, the gate mechanism includes a hinged door. In some embodiments, the gate mechanisms includes one or more rotating disks, such as a rotating disk with corresponding aperture. In some embodiments, the gate mechanism includes one or more shutter mechanisms. However, the present disclosure is not limited thereto.

Accordingly, the gate mechanism of each rigid cartridge 1100 allows for reusability, in that, the gate mechanism can be used multiple times by the robotic material transfer system to sample the cellular engineering target accommodated by the interior of the rigid cartridge. This multi-use usability of the gate mechanism can guarantee sterility and protection of the cellular engineering target. Moreover, this gate mechanism is preferable to single-use solutions, because the gate mechanism occupies a smaller volume than other single use mechanisms. Furthermore, the gate mechanism of the rigid cartridge does not limit a number of samples of the cellular engineering target that can be extracted from the rigid cartridge.

FIGS. 19A, 19B, and 19C shows various possible configurations for a channel 1900 that extends from an aperture (e.g., aperture 1180 of FIG. 14) of rigid cartridge 1100. which allows for communication with an interior of the rigid cartridge. In some embodiments, the channel is a tube that connects the gate mechanism with the cellular engineering target accommodated within the interior of the rigid cartridge that is to be sampled. However, the present disclosure is not limited thereto. In some embodiments, the channel includes a rigid channel. In some embodiments, the channel includes a straight channel. For instance, in some embodiments, the channel is rigid and straight, or substantially straight. In some embodiments, the channel is non-rigid (e.g., flexible). In some embodiments, the channel is in non-straight configuration, such that a shape of the channel includes be curvilinear shapes, shapes with right angles, or a combination thereof. Accordingly, the channel includes a length that is sufficient to reach a level of a liquid cellular engineering target even when the level is low, or when the cellular engineering target is in a corner of the cartridge. As such, the shape of the channel can be optimized, so that the robotic material transfer system conducting collecting a sample of the cellular engineering target from the rigid cartridge in an effective and time efficient manner.

In some embodiments, the robotic material transfer system includes a pressure-differential mechanism, such as a syringe and/or a pump, to collect the sample of the cellular engineering target via suction, which causes the channel to fill with the fluid sample of the cellular engineering target. At the end of this sampling procedure conducted by the robotic material transfer system, having the channel be empty from residual fluid is necessary. This emptying of the channel can be achieved by tilting the rigid cartridge that includes the cellular engineering target, such as via articulated handling robot 202 of the robotic material transfer system and/or an actuated base platform of frame 206. In such embodiments, when the rigid cartridge is inclined, gravity pushes the fluid cellular engineering target towards a lower end portion of the rigid cartridge. Accordingly, by controlling the inclination of the rigid cartridge, a designer of the systems and methods of the present disclosure can ensure that there is no fluid at the bottom of the channel. This way, the robotic material transfer system can retrieve the fluid cellular engineering target that remained in the channel. In some embodiments, as the channel is emptied of fluid, the channel is filled with air as there is no fluid anymore at a base of the channel (e.g., open end portion of the channel in the interior of the rigid cartridge. Tilting or inclining the cartridge that includes the cellular engineering target is especially easy if this tilting process makes use of a rocking bioreactor instrument 300 (e.g., instrument 300-2 of FIG. 12), that includes a substantially planar upper platform which tilts about an axis.

In some embodiments, in order to retrieve the sample, once a connection to aperture 1180 that includes channel 119 has been established by the robotic material transfer system, the robotic system can utilize a single-use pressure differential mechanism, such as a syringe or a pipette. These consumable, one-use single-use pressure differential mechanisms can be stored within (e.g., accommodated within an opening on a surface of the rigid cartridge) the modular biological foundry system in one or more rigid cartridges that are inserted in pre-determined slots by manufacturing operators (who are located outside of the modular biological foundry system). Accordingly, in some embodiments, the rigid cartridge is inserted in and/or removed from via second sealing mechanism 224 of module 208 of frame 206 of the modular biological foundry system without compromising or affecting the clean-room, sterile environment inside of the frame. Furthermore, in some embodiments, the single-use pressure differential mechanism is sealable, it can be used also as the sampling includes. For example, in some embodiments, threaded syringes can be "locked" by screwing a cap onto their threaded opening once the sampling procedure is completed. In such embodiments, after the cap is mounted on the syringe, the assembly (syringe+cap) constitutes a sealed container which can then be delivered a user through a sealing mechanism of the modular biological foundry system.

In some embodiments, the pressure differential mechanism (e.g. a syringe or a pipette) is operated by the robotic material transfer system, such that the robotic material transfer system includes an articulated handling robot 202 and/or flexure gripping device that allows flow controlled gripping of the pressure differential mechanism. In this way, the robotic material transfer system must be able to securely grasp and hold the pressure differential mechanism. At the same time, the gripper must also be able to actuate the pressure differential mechanism (e.g. actuate a piston of a syringe). For this reason, in some embodiments, the robotic material transfer system includes a composite gripper device that combines a grasping function with a pressure (e.g., suction) control function. This composite gripper device includes at least two separate actuation mechanisms to control the at least two separate functions, such a first actuation mechanism to control a grasping function and second actuation mechanism to control a suction function.

In some embodiments, the modular biological foundry includes a tool change system what allows the robotic material transfer system to utilize different mechanisms required to interact with one or more modules 208, one or more instruments 300, one or more rigid cartridges 1100, or a combination thereof. For instance, consider if a first gripper device is substantially different from a second gripper device that the robotic material transfer system needs to perform other tasks, it will be necessary to include the tool changing system within the modular biological foundry system. In this way, the robotic material transfer system can then use the tool changing system to swap different gripping devices to change the end effectors of the robotic material transfer system. Accordingly, the gripper device that is appropriate for a particular task (e.g., moving a rigid cartridge or sampling a cellular engineering target from the rigid cartridge) is automatically mounted on the robotic arm before the particular task is performed.

As described supra, the modular biological foundry system includes modules 208 that are accommodated by frame 206. In some embodiments, each module 208 carries out a single task or a defined set of tasks within a process to manufacture a cellular manufacturing target based on an instrument 300 accommodated by the module. Accordingly, after the module has completed the single task or the defined set of tasks, the robotic material transfer system moves the rigid cartridge to a second module 208 that performs a subsequent task or defined set of tasks.

In this way, each module 208 accommodates an instrument 300. In some embodiments, the module also includes one or more support systems that support a task performed by the instrument, such as electronics system (e.g., sensor system), air filter system, and the like. Since different modules 208 perform a wide variety of tasks within a manufacturing process for producing a cellular engineering target (e.g. a first module 208-1 performs centrifugation via a centrifuge instrument 300-1, a second module 208-2 performs freezing or thawing via a heat exchange instrument 300-2, a third module 208-3 includes a bioreactor instrument 300-3 to expand a cellular engineering target, etc.). Accordingly, the way in which the robotic material transfer system operates and interfaces with each module 208 and/or rigid cartridge 1100 is dependent on the specific features of the module and/or the rigid cartridge, or the instrument accommodated by the module. As such, in some embodiments, in order to allow the robotic material transfer system to operate autonomously with each module in the modular biological foundry system, a corresponding rigid cartridge for each type of module is provided.

As used herein, a "cartridge" is a container where a cellular engineering target and/or one or more reagents that is needed to complete a manufacture of the cellular engineering target is stored within an interior of the cartridge. The cartridge also allows the robotic material transfer system to easily manipulate the cellular engineering target and its ingredients, picking the cartridge up from a first module 208 and placing then the cartridge into a second module. In other words, the cartridges can be easily operated by the robotic material transfer system, which is desired to ensure that the entire cellular engineering target manufacturing process is performed autonomously within the modular biological foundry system. In this way, the cartridge is an interface between the robotic material transfer system and the instrument that is included within the module. Given that the instrument is typically designed to be operated by human users, the cartridge simplifies a task of facilitating operating the instrument via the robotic material transfer system. Furthermore, by allowing the robotic material transfer system to not only engage the cartridge but also operate an instrument 300 (instead of a user operating the instrument), the cartridge is an desired step in guaranteeing the sterility and the repeatability that is provided by the modular biological foundry system.

In some embodiments, the modular biological foundry system is modular both from the hardware (e.g., frame 206, modules 208, cartridges 1100, etc.) but also from an ability of the modular biological foundry to interface and communicate with computer system 100 point of view. In this way, the robotic material transfer system connects the various modules of the frame within modular biological foundry system by moving one or more cartridges 1100 between different addresses of the modules within the frame. At the same time, in some embodiments, the computer system 100 manages a flow of materials and manufacture of cellular engineering targets throughout the modular biological foundry system. In some embodiments, this oversight and management provided by the computer system is remote. In some embodiments, this oversight and management requires constant communication via communications network 106 between the modular biological foundry and the computer system, such that real-time data associated with the manufacture of the cellular engineering targets is provided from the biological foundry system to the computer system. However, the present disclosure is not limited thereto. In some embodiments, the computer system includes one or more board modules that represents each module. Each board includes module-specific drivers, which allows the computer system 200 to operate the instrument 300 that is accommodated in the module. In some embodiments, the board also includes a network interface that allows the module to communicate with the other modules in the modular biological foundry system, such as via communications network 106.

As described supra, rigid cartridges 1110 of the present disclosure allow different modules 208 to perform different operations with one or more instruments 300 on the same cellular engineering target, while protecting the sterility of the cellular engineering target and, therefore, enabling complete process automation (e.g., manufacture of the cellular engineering target without human interference).

Figure 20:
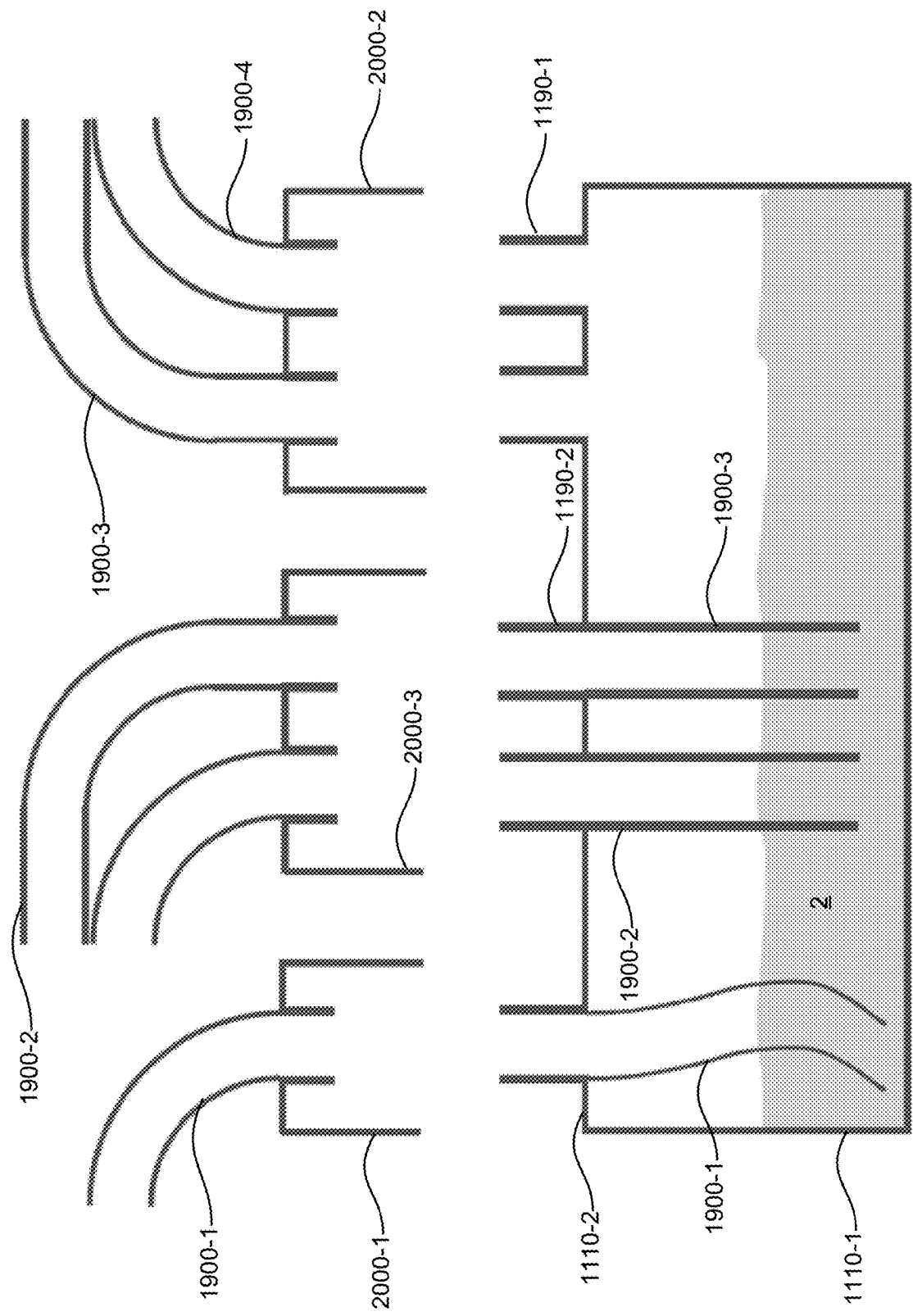
FIG. 20 is a side view of yet another rigid cartridge, in accordance with an embodiment of the present disclosure.

Referring briefly to FIG. 20, a view of first rigid cartridge 1100-1 that includes cellular manufacturing target 2 is provided. An interior of the rigid cartridge is defined by rigid side walls 1100 and is typically dedicated to storing the cellular engineering target that is in liquid, or substantially liquid, form, such as a solution including cells. In some embodiments, the cellular engineering target is in gel, semi-solid, or solid form, and the cartridge is also able to includes these different forms of the cellular engineering target. However, the most common form of cellular engineering targets is the liquid form—so the present disclosure will mainly focus on the liquid form. However, one of skill in the art of the present disclosure will appreciate that the present disclosure is not limited thereto.

In some embodiments, the cellular engineering target is stored in a fixed interior defined by rigid walls 1110 of the cartridge. In some embodiments, the cellular engineering target is accommodated by a soft body bioreactor that is removably coupled with the rigid cartridge (e.g., soft body bioreactor 1200 of FIG. 13). The advantage of a soft body bioreactor is that is does not obstacle the flow of fluids from and into the rigid cartridge, while, in contrast, a conventional rigid container would need to allow air to come in as fluid exits and air to get out as fluid enters. However, this issue is resolved by including one or more connectors 1190 that facilitate communication with the soft body bioreactor. For instance, in some embodiments, the connector includes a valve that allows for fluid to enter or exit the soft body bioreactor to enable liquid transfer via the robotic material transfer system.

An exterior of each rigid cartridge is a defined by rigid walls 1110. The rigidity provided by the rigid walls allows the robotic material transfer system to easily engage with the exterior of the rigid cartridge, such as picking the rigid cartridge from a first module 208-1 and placing the rigid cartridge in a fourth module 208-4 in accordance with instructions communicated via computer system 100. Moreover, in some embodiments, the rigid walls of the rigid cartridge also allow the rigid cartridge to be placed and secured in a docking device instrument (e.g., docking device 300-1 of FIG. 9), such that engagement members can engage the rigid cartridge without deforming the exterior of the rigid cartridge. Additionally, in some embodiments, the rigid walls of the rigid cartridge include the apertures that simplify the engagement (e.g., insertion and/or extraction) of the connector with one or more ports of the soft body bioreactor. In other words, the rigid exterior of the rigid cartridge makes provides a simple interface for the robotic material transport system to engage, and therefore move the rigid cartridge about the modular biological foundry system, to interface the rigid cartridge with the instruments accommodated by the modules, and to collect samples of the cellular engineering target from the rigid cartridge.

In some embodiments, the rigid cartridge includes two or more internal sections, which allows for different materials to be stored in each respective internal section of the two or more internal sections. In this way, each internal section of the rigid cartridge includes one or more apertures with corresponding connectors 1180, and, optionally, channels 1190, which allows the robotic material transfer system to sample from a respective internal section of the rigid cartridge and to connect the internal section with other rigid cartridges or systems, such as a reservoir of material. Examples of the connectors include a sampling connector, a fluid connector for input of liquid and/or gas into the rigid cartridge or for output of liquid and/or gas from the rigid cartridge. In some embodiments, the connectors enable the robotic material transfer systems to insert one or more sensors into the interior of the rigid cartridge, such as in contact with the cellular engineering target (e.g., bringing the sensors or probes in contact with the liquid cell cellular engineering target). Accordingly, the connectors of the rigid cartridge allow for sterile and automated access to the interior of the rigid cartridge, such as allowing access to the cellular engineering target.

In some embodiments, in order to safely connect support systems to connectors 1180, the robotic material transfer system engages a rigid socket and plug the rigid socket with the connector.

Figure 16:
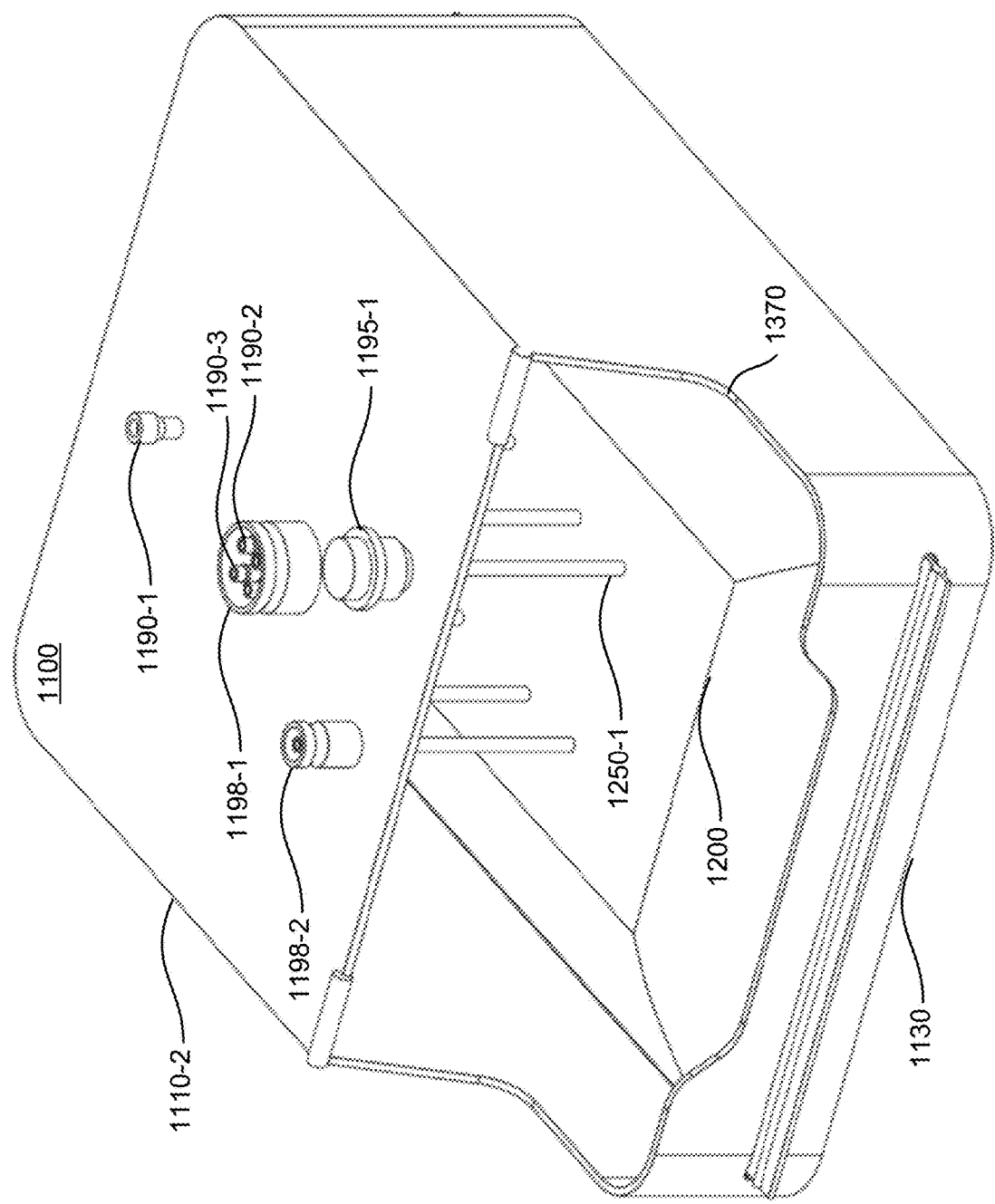
FIG. 16 is yet another perspective view of a plurality of instruments of a biological foundry including a rigid cartridge, in accordance with an embodiment of the present disclosure.
Figure 17:
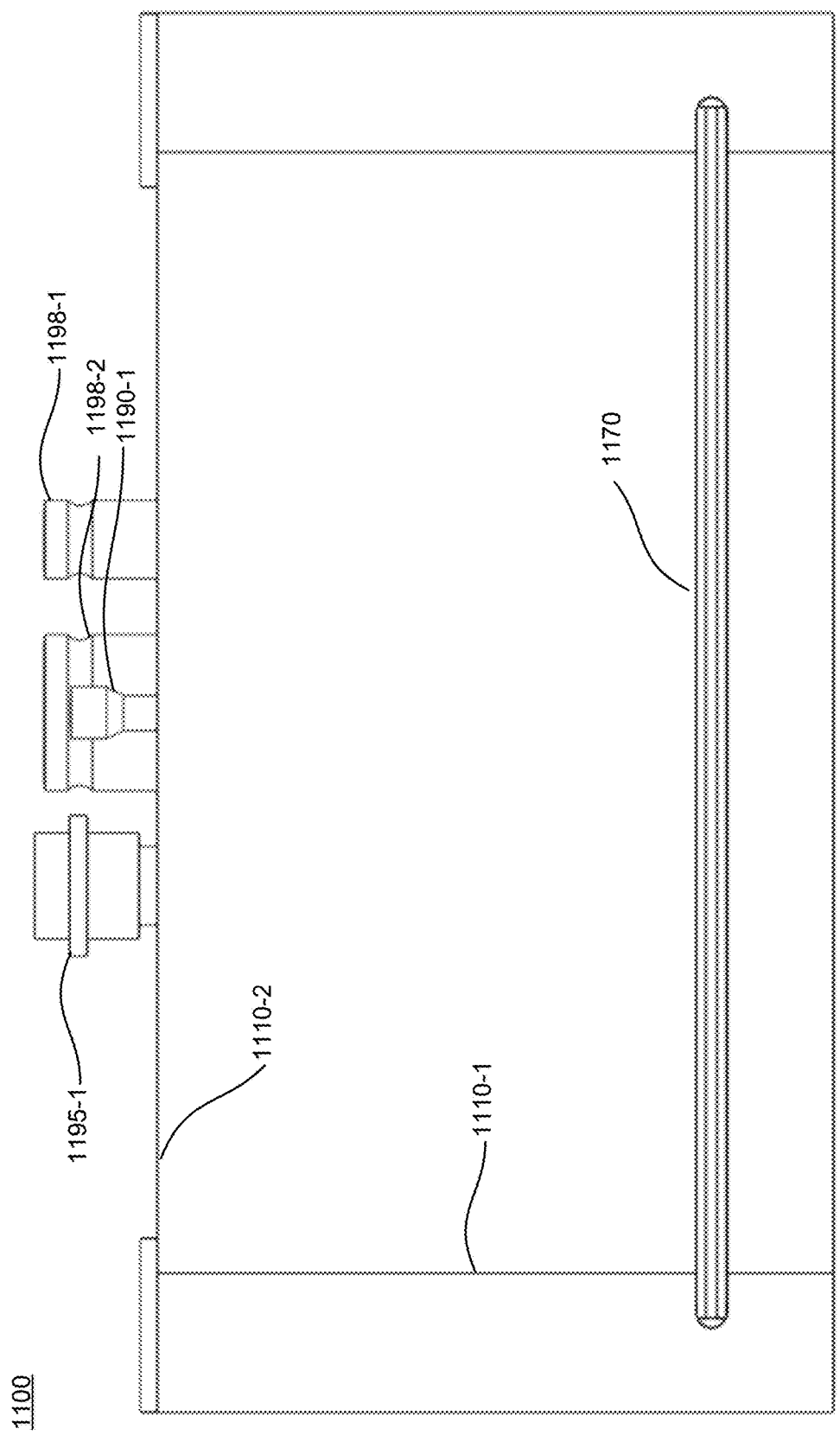
FIG. 17 is a side view of a rigid cartridge, in accordance with an embodiment of the present disclosure.

Referring to FIG. 16 and FIG. 20, in some embodiments, connector 1190 is surrounded by a mating mechanism, such as an annular hood (e.g., annular hood 1195), that protrudes from an upper surface of the rigid cartridge in order to guide the motion of the rigid sockets, making the connection/disconnection of the rigid sockets from the connectors an easy process, as well as rapid and repeatable for the robotic material transfer system. In such embodiments, both the sockets of the robotic material transfer system and the annular hood of the rigid connector are realized with rigid materials that simplify grasping for the robotic material transfer system. In some embodiments, the annular hood protrudes to a greater height than the connector, such that the connector is protected from horizontal motion of the robotic material transfer system. In some embodiments, the annular hood is cylindrical or substantially cylindrical. In some embodiments, the annular is configured to engage with a socket 2000, which allows for the robotic material transfer system to engage with the annular hood and communicate with the connector of the rigid cartridge. In some embodiments, these parts include compliant features (above described docking station), which help with self-alignment and repeatability. By placing a rigid socket at the end of a flexible channel 1190, it is possible to make it very simple for a robotic arm to connect that channel to the connectors of the rigid cartridge. In such embodiments, the robotic material transfer system does not have to directly manipulate the flexible tube (manipulating soft objects is problematic for industrial robots). Instead, the robotic material transfer system simply needs to grasp the rigid socket and insert the rigid socket in the corresponding connector or connectors on the rigid upper surface of the rigid cartridge.

Similarly, the connection between the socket of the robotic material transfer system and the connector and/or the annular hood of the rigid cartridge can be removed simply by disengaging the parts (e.g., grasping) and removing the rigid socket. In this way, in such embodiments, the robotic material transfer system does not interacts with soft parts, but rather the robotic material transfer system simply manipulates a rigid part (e.g., rigid cartridge, module, etc.), moves the rigid part, inserts the rigid part, extracts rigid parts, or a combination thereof from a first position in the modular biological foundry system to a second position.

Accordingly, in such embodiments, the sockets 2000 of the robotic handling system have a function in that the sockets allow the robotic material transfer system to repeatably mate flexible parts such as a flexible channel or soft body bag with the connector on the rigid cartridge. Furthermore, the sockets ensure a sterile connection, such that the cellular engineering target is protected from the external environment. The sockets also yield a repeatable, multi-use connection. It is possible to connect and disconnect a socket from a connector more than once. This avoids the problems of single-use systems (i.e. high costs, significant waste, need for more space, limits to the number of operations that can be performed).

In some embodiments, before engaging socket 200 with connectors 1190 and/or annular hoods 1195 of rigid cartridge 1100, the robotic material transfer system (e.g. articulated handling robot 202) conducts a sterilization process on one or more surfaces, such as each surface of the socket and/or each surface of the cartridge. In some embodiments, this sterilization process is carried out autonomously by a dedicated end effector for the robotic material transfer system (or by an add-on mechanism to other end effectors for the robotic material transfer system). In some embodiments, localized sterilization strategies utilized by the sterilization process include spraying sterilizing chemicals (e.g. isopropyl alcohol), applying sterilizing gases (e.g., ozone), using ultraviolet lights (e.g., UV-B and/or UV-C light) or any kind of sterilizing radiation, physically wiping the surface with a material, such as a first material imbued with sterilizing chemicals, or a combination thereof.

By sterilizing all the surfaces involved in the socket mating and connectors access process, the robotic system ensures that all the connections are sterile. This is essential to guarantee that the cellular engineering target is always included within closed, sterile systems. This feature meets and exceeds the safety features of conventional (non-automated) closed systems for the manufacturing of cell therapies. In fact, traditional closed systems are still operated by human technicians. Therefore, a big source of contamination is right in front of the system (the operator). On the contrary, in the modular biological foundry system structure described here, the closed systems (i.e. systems with tubes, bags, cartridges that accommodates and protect the cellular engineering target at all times) are operated by an entirely autonomous system within a completely sterile clean-room environment (inside the modular biological foundry system's frame). This minimizes the risk of contamination, creating a double barrier—the cell therapy products are protected both by the closed system that surrounds them, and by the isolated clean-room nature of the modular biological foundry system that includes all products and all machines (but no humans).

In some embodiments, an additional advantage of using rigid sockets 2000 that are placed at the ends of channels 1900 is allowing rigid cartridge 1100 to move while a process task is being completed at a respective module 208 via a corresponding instrument 300. For example, in some embodiments, the rigid cartridge includes the cellular engineering target can engage a surface an instrument, such on a rocking bioreactor instrument 300-2 of FIG. 13 (e.g., within a bioreactor module 208). Accordingly, the instrument includes an upper surface forming a platform that rocks back and forth, continuously mixing the cellular engineering target accommodated in the rigid cartridge and ensuring that the reagents reach every part of the cellular engineering target when supplied through the socket via the robotic material transfer system. In some embodiments, rigid walls 1110 form a seamless lip at a lower end portion of the rigid cartridge, which engages the upper surface of the instrument to secure (e.g., removably couple) the rigid cartridge and the instrument. In some embodiments, if these reagents are supplied through the channels that are flexible are connected via the sockets to the connectors on the upper rigid wall of the rigid cartridge, the rocking motion of the rigid cartridge on the upper surface of the instrument causes no issues. In some embodiments, the same approach of utilizes the flexible channels and the sockets can be applied to establish the flow of other liquids and gases as inputs or outputs to the rigid cartridge, while allowing the rocking motion of the cellular engineering target within the rigid cartridge. This rigid cartridge, which combines flexible elements (e.g., channel 1900, soft body bioreactor 1200, etc.) and rigid elements (e.g., rigid walls 1110, connectors 1900, sockets 2000, etc.) enables automation of complex tasks at the modular biological foundry system that are usually performed by operators.

The connectors of the rigid cartridge can be of any of the types previously described (see the section about sampling connectors). The connectors of the rigid cartridge can also be connected to any of the previously described types of channels. The socket-connectors architecture ensures a sterile, repeatable connection that can be established multiple times (reusable) by a fully automated system.

The cartridge configuration that has been described so far is ideal for use in a bioreactor module. Different cartridges can be designed for different purposes, and in order to adapt to different pieces of machinery. In this approach, every module within the modular biological foundry system can have its own cartridge, allowing the complete automation of each step of the manufacturing process. When possible, the systems and methods of the present disclosure can also design "general purpose" cartridges that are able to interface with multiple different modules.

Figure 21:
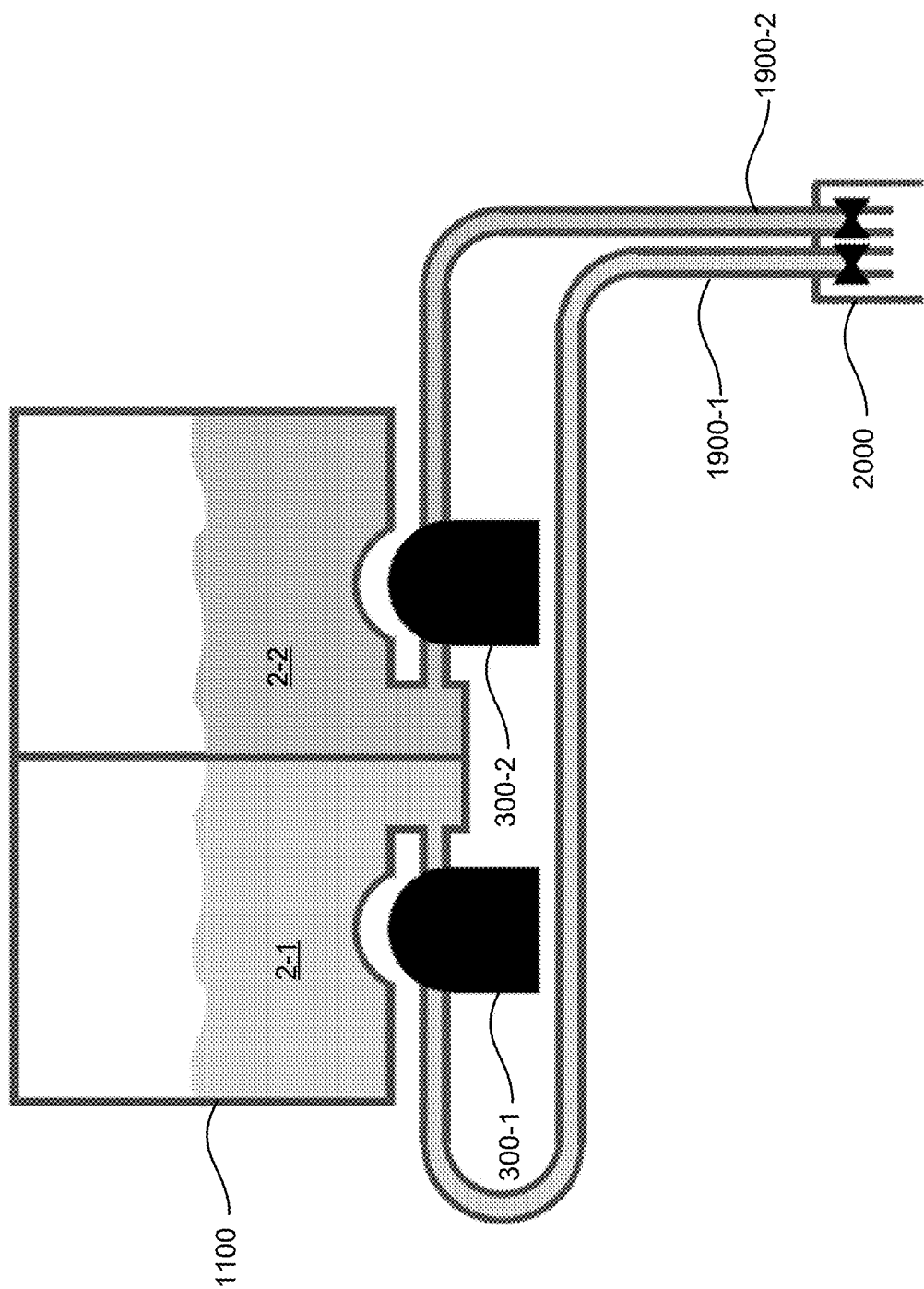
FIG. 21 is a schematic view of yet another rigid cartridge, in accordance with an embodiment of the present disclosure.

An example of a different type of cartridge is represented by the liquid reservoir cartridge (e.g., FIG. 21). This type of cartridge includes one or more internal sections. Each section includes a particular liquid—it could be an input material (e.g. media for cell culture) or an output material (e.g. waste). Each section is connected to one or more flexible channels through which liquid can exit the cartridge or enter the cartridge. All the channels connected to the various sections of the cartridge are bundled together in a single, flexible channel. At the end of it, there is a socket which includes a connectors interface termination for each fluid channel. The rigid socket that can be grasped by a robotic manipulation system and inserted into a rigid cartridge. This single insertion operation immediately established contact among multiple channels (originating from the cartridge) and multiple connectors on the cartridge.

In some embodiments, the socket can also be equipped with valves that stop the flow of fluid. The valves can be operated by the robotic material transfer system, by pushing or moving features (e.g. buttons, levers, etc.) on the outside of the socket. This way, the robotic arm can both insert the socket, and allow/block the flow of illiquid by operating the valves. Moreover, the presence of valves at the end of the channel (just before it is connected to the connectors on the rigid cartridge) eliminates the risk for liquid spills and cross-contamination. In some embodiments, the channel includes one-way valves, in order to ensure that the flow along a channel can only go in a pre-determined direction. And by adding filters, it is possible to prevent unwanted product components or reagents travel along channels where their presence must be avoided.

In some embodiments, one or more the flexible channels that originate from a liquid reservoir cartridge can be bundled together to form a single, flexible channel bundle and to avoid getting caught in protruding mechanical features. This channel bundle must have enough slack to enable the robotic material transfer system to grasp the socket, move it and insert it into its destination cartridge. At the same time, the channel bundles dimensions and its overall length are designed to avoid getting caught in other machines as the robotic material transfer system takes care of the connection/disconnection processes. Additionally, the channel bundle must also provide enough slack to enable the destination cartridge (to which the socket is connected) to move (e.g. on a rocking bioreactor instrument).

The channels that originate from a liquid reservoir cartridge (e.g., rigid cartridge 1100-4 of FIG. 21) can be designed so that the channels pass in front of a rigid surface that mimics the outer shape of a peristaltic pump instrument (e.g., instruments 300 of FIG. 21). This way, when the liquid reservoir rigid cartridge is placed on the peristaltic pump instrument by the robotic material transfer system, the channel will be automatically inserted in a portion of the peristaltic pump instrument. In some embodiments, a mating surface of the rigid cartridge, closely following an outer surface of the peristaltic pump instrument, will then keep the channel in place. In some embodiments, a rigid cartridge with multiple sections (i.e. accommodating multiple separate liquids) includes multiple channels. In this case, all the channels can be inserted in multiple peristaltic pump instruments at the same time. For this to occur, the rigid cartridge is placed by the robotic material transfer system on a set of multiple different peristaltic pumps instrument (e.g., one for each channel in which a designer of systems and methods of the present disclosure wants to control liquid flow through). And each channel must be kept in place by a mechanical feature on the outer surface of the rigid cartridge that mimics the outer shape of the peristaltic pump (e.g., FIG. 21). This way, the flow of each liquid in each channel can be controlled independently by separate peristaltic pump instruments.

Accordingly, this rigid cartridge isolates the flow of each liquid in a separate closed circuit, protected from the external environment. In other words, all fluids traveling from or to the liquid reservoir rigid cartridge are always accommodated within a closed, sterile set of channels. This approach meets or exceeds all the requirements of traditional closed systems for the manufacturing of cell therapies, in that this approach is completely automated—achieving superior safety (requires no human users; no sources of contamination) and superior efficiency.

In some embodiments, different partitions inside of the rigid cartridge (each including a different fluid) are defined by rigid walls 110. In some embodiments, the interior partitions include a mechanism that allows fluids to flow in and from the partitions without resistance. For example, in some embodiments, each interior partition of a rigid cartridge includes a valve and/or a filter mechanism. In particular, the valve lets air in as the stored liquid exits the reservoir. Likewise, the valve lets air out as new fluid enters the reservoir. The presence of the filter mechanism ensures that the air going through the valve does not contaminate the product, or the external environment. The same effect can be obtained by adding a flexible membrane (diaphragm) to a cartridge section, or by implementing the reservoir through a soft body bioreactor that is accommodated by the rigid cartridge (in this case, a separate soft body bioreactor is needed for each fluid reservoir inside the cartridge). The flexible membrane and the soft body bioreactor can expand and contract, and do not oppose fluid coming in or getting out.

Figure 22:
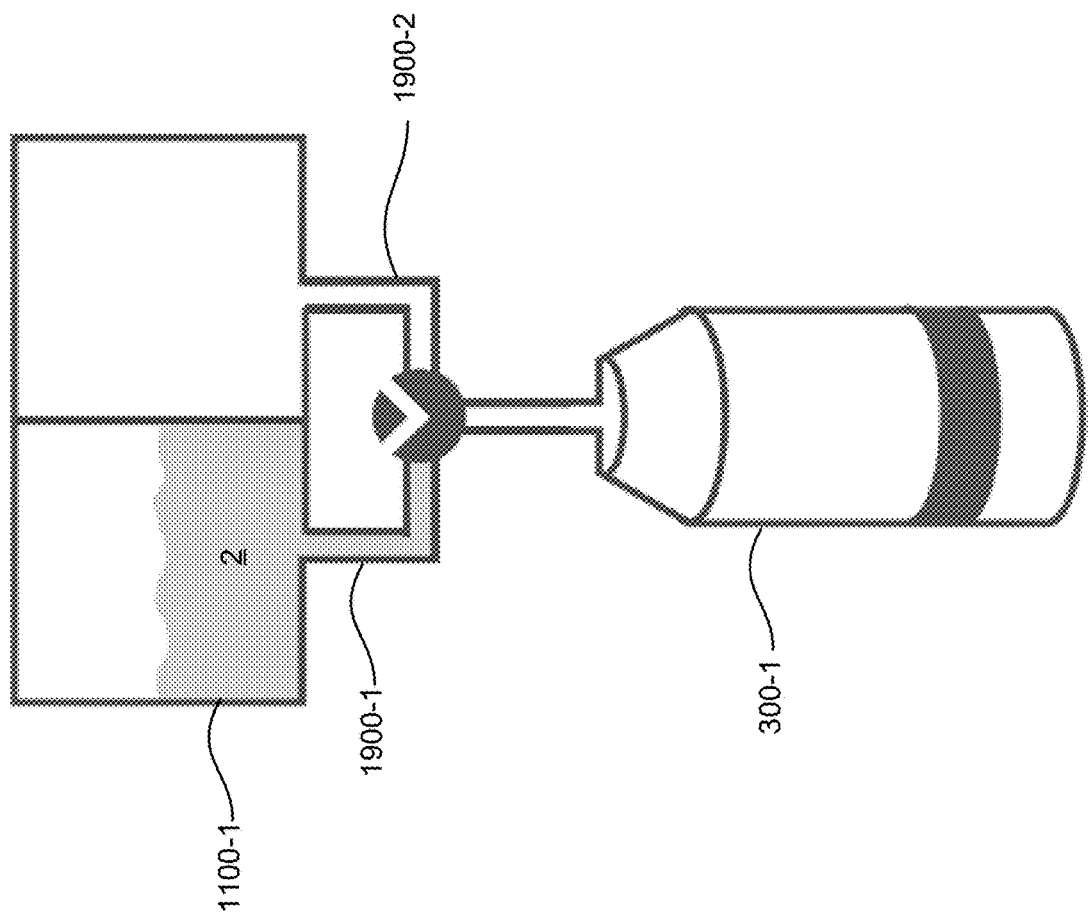
FIG. 22 is a schematic view of yet another rigid cartridge, in accordance with an embodiment of the present disclosure.

Another example of a special-purpose cartridge is a cartridge that is designed to automate the operation of a centrifuge (e.g., FIG. 22). A centrifuge for cell therapy manufacturing must transfer the cellular engineering target from an input reservoir to a centrifugation vessel, where the different components of the cellular engineering target are separated by density. Then, a piston pushes the different components of the cellular engineering target out of the centrifugation vessel, and into output reservoirs. The whole process must be executed in a sterile, closed system of channels and reservoirs.

The centrifugation cartridge includes a section to store the input material (this section accommodates the initial cellular engineering target at the beginning of the centrifugation task). The centrifugation cartridge is also equipped with one or more sections for the various parts of the output of the centrifugation task (these sections start our empty and are then progressively filled during the centrifugation task). All the different sections of the cartridge are connected to the centrifugation vessel through tubing and a multi-directional valve. The valve can be controlled from the outside of the cartridge by the robotic material transfer system (by operating a knob or a lever). This way, the robotic material transfer system can select the valve configuration that connects the centrifugation vessel with the cartridge section that is needed at a particular point of the centrifugation task. Note that the whole cartridge can be placed on one or more peristaltic pumps (like the fluid reservoir cartridge described before). Once the channels lock onto the peristaltic pumps, they can be used to control the flow rate of the liquids from/to the reservoirs.

To begin the process, the robotic material transfer system turns the valve so that the input liquid drips (or is moved by a peristaltic pump) into the centrifugation vessel. Once the fluid reaches the centrifugation vessel, the centrifuge starts rotating it. This separates the different components of the cellular engineering target by density. At this point, the piston moves upwards, pushing out of the centrifugation vessel one fraction of blood at a time (e.g., FIG. 22). Now, the robotic arm changes the position of the valve, so that the fractions of cellular engineering target that have been separated by the centrifuge can be directed into one or more separate output reservoirs. This process is repeated until all the useful fractions of the cellular engineering target have been pushed into the output reservoirs. In this case too, the presence of additional peristaltic pumps can help control the flow rate of the output liquids.

The reservoirs of liquid that are present into the centrifugation cartridge can be implemented either as soft bags accommodated a hard cartridge shell, or as hard containers that are equipped with valves and filters that let air in or out in order not to obstruct the motion of the fluids. It is also possible to substitute the valves and filters with soft membranes (diaphragms).

In some embodiments, multiple rigid cartridges 1100 can be positioned in the same module by the robotic material transfer system (e.g. articulated handling robot 202). Accordingly, all the rigid cartridges that have been placed inside of the module can be liked together by a robotic material transfer system, forming a single closed system, such as by linking one or more connectors 1190 from each rigid cartridge in the module 208. This combined, modular closed system unites multiple rigid cartridges and systems by using the sockets that are grasped by the robotic material transfer system, moved to a target location, and inserted in or extracted from a target rigid cartridge.

Figure 23:
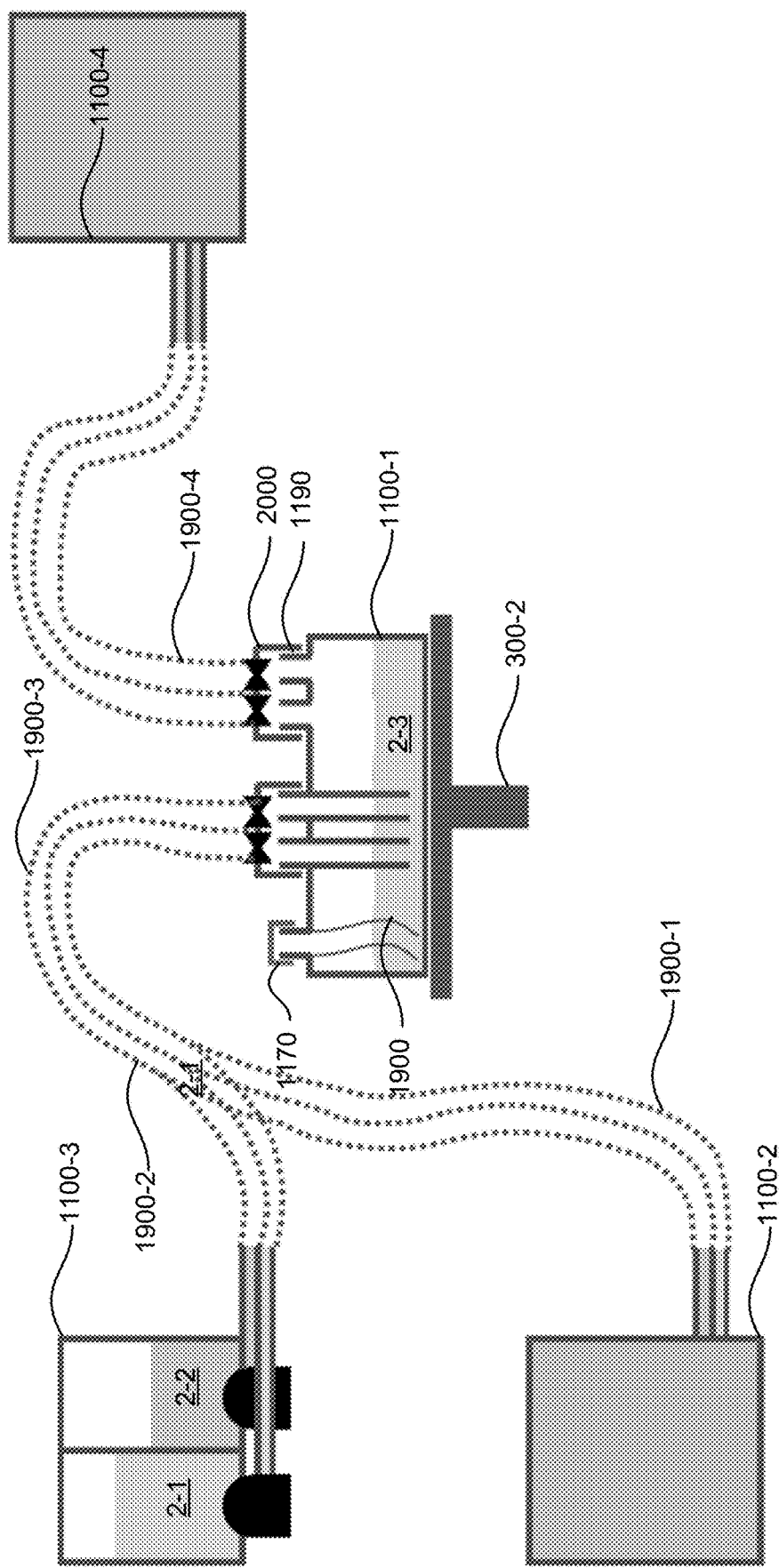
FIG. 23 is a schematic view of a modular clean room biological foundry, in accordance with an embodiment of the present disclosure.
Figure 24:
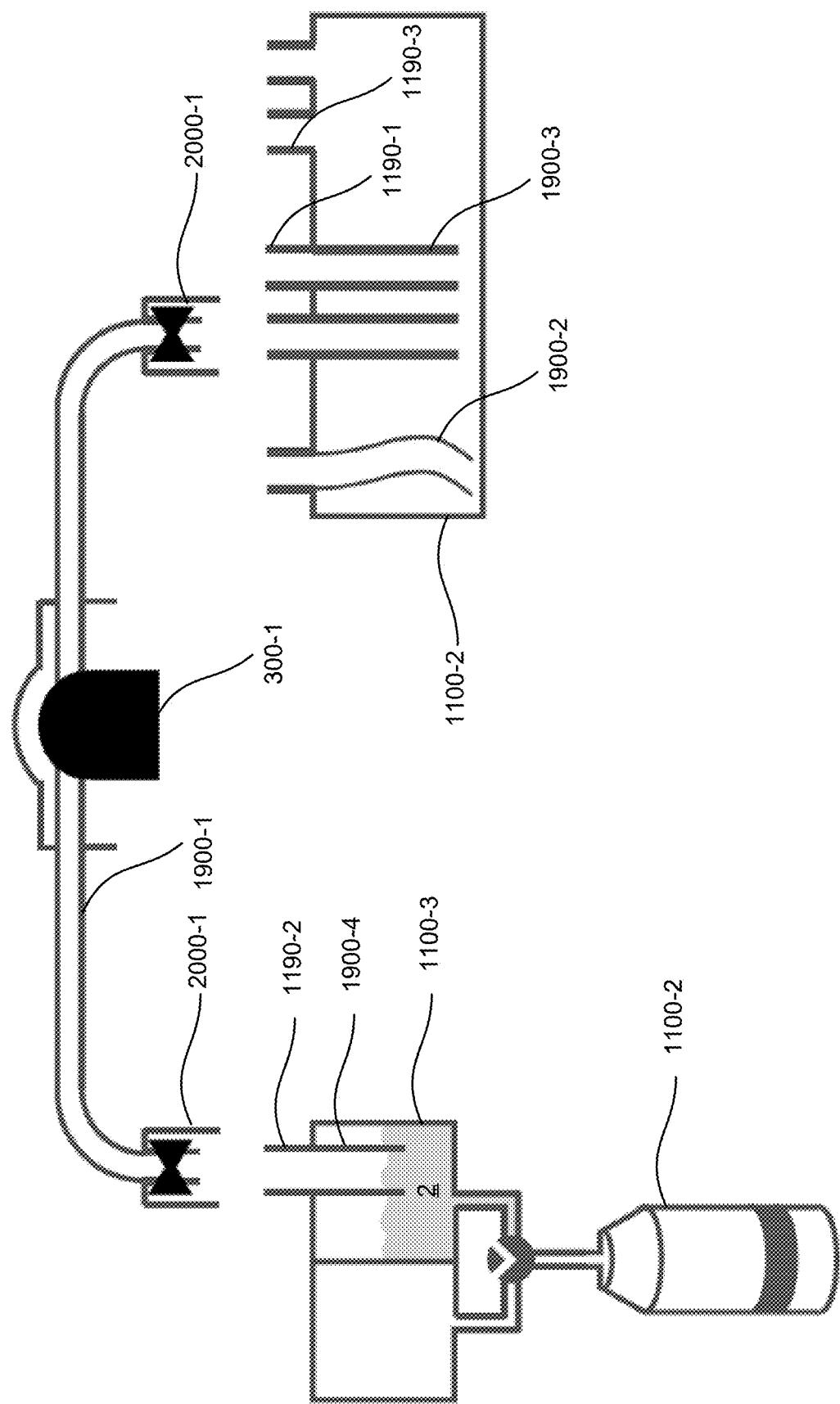
FIG. 24 is a schematic view of a modular clean room biological foundry, in accordance with an embodiment of the present disclosure.

For example, referring briefly to FIG. 23, in some embodiments, a rigid cartridge is disposed on (e.g., lip of rigid cartridges engages) an upper surface of a rocking bioreactor instrument, such that a lip of the rigid cartridge engaging an upper surface of the instrument. The connectors of the rigid cartridge allow the robotic material transfer system to sample the cellular engineering target whenever requested (or pre-scheduled) by a user at computer system 100. Accordingly, the robotic material transfer system engages the rigid cartridge with a second rigid cartridge (e.g., a liquid reservoirs material rigid cartridge), using the sockets. As such, these additional inputs and outputs allow the system to add materials to the cellular engineering target or remove materials from interior of the rigid cartridge via the connectors. The connectors also allow the robotic material transfer sensor to place sensors in the interior of the rigid cartridge, if needed. Since these connectors are sterile, the closed-system nature of the rigid cartridge is always guaranteed.

This modular closed-system architecture allows the combination of multiple cartridges and systems to automate every task of the manufacturing process of producing cellular engineering targets, while ensuring that the cellular engineering target is always accommodated in sterile channels and interior partitions of a rigid cartridge that are physically separated from the external environment by rigid walls 11100.

In some embodiments, a channel can bundle multiple smaller channels together, to form a coupling of channels.

For instance, in some embodiments, each channel includes slack (e.g., excess length) and includes a flexible material that allows the robotic material transfer system to move the socket and connect it to one or more connectors in a corresponding rigid cartridge. The rigid socket can also include valves (e.g., the valves can be automated, or they can be operated by the robotic material transfer system with mechanical features that are present on an exterior surface of the socket).

In some embodiments, the instruments include peristaltic pumps, that allow the channel tubing to interface with peristaltic pumps instruments, that in turn control the flow rate of the fluids inside the channels and the interior of the rigid cartridge.

In some embodiments, the rigid cartridges 1100, connectors 1190, channels 1900, and sockets 2000 can be combined and connected by the robotic material transfer system, in order to realize a larger closed modular biological foundry system that allows a cellular engineering target manufacturing task to be carried out. As such, multiple rigid cartridges and subsystems can be connected using sockets and connectors. In some embodiments, peristaltic pump instruments can engage the channels regulate flow rate. In some embodiments, the valves in the sockets and in the connectors help the system constrain the direction of the flow in the channels. In some embodiments, the rigid cartridges can be connected with other rigid cartridges (or placed inside of other rigid cartridges) to achieve more advanced, composite functions.

In some embodiments, by automatically combining the above described elements, a robotic material transfer system can dynamically create any kind of closed system at a modular biological foundry system and enable a cellular engineering target manufacturing task to be carried out. This approach is very general, and enables the automatic assembly and disassembly of sterile closed systems at the modular biological foundry system that can: store fluids in separate rigid cartridges; transfer fluids (with a controlled flow rate) between rigid cartridges; and process fluids (e.g., modifying the cellular engineering target as part of the various cell therapy manufacturing tasks).

Referring briefly to FIG. 21, an example of a large modular closed system that is automatically assembled by a robotic inside of a module (in the modular biological foundry system). In some embodiments, a first liquid reservoir rigid cartridge is be connected by a robotic material transfer system (e.g. a robotic arm) to a set of peristaltic pump instruments, and then plugged by the robotic material transfer system into the second rigid cartridge. This allows the modular biological foundry system to supply new reagents to the cellular engineering target of the second rigid cartridge, and to remove waste liquid.

In some embodiments, a liquid cabinet (e.g., FIG. 23) can be plugged into the rigid cartridge (e.g., instead of the liquid reservoir rigid cartridge). The liquid cabinet is much larger than a cartridge and can include a much larger quantity of input or output liquids than the liquid reservoir cartridge. The liquid cabinet also includes integrated pumps that control the flow to and from its reservoirs. In some embodiments, this is different from the liquid reservoir cartridge, which is designed to be used for a single cellular engineering target (or for a limited number of cell therapy products), because its size is limited by its volume and by the payload of the robotic material transfer system. On the other hand, the liquid cabinet is designed to service a large number of different cellular engineering targets produced at the modular biological foundry system, because its volume and weight can be much bigger than those of a cartridge, and its pumping systems are already integrated in its channels. The liquid cabinet can be plugged into multiple cartridges by a robotic material transfer system, one after the other (as they are transported into the module by the robotic material transfer system). This is also enabled by the socket system, which is sterile and multiuse. Additionally, the valves in the ensure that the flow always goes in the right direction. Unidirectional valves can also be added to the socket, in order to prevent fluid backflow in an undesired direction (this reduces the risk of spills and cross-contamination).

In some embodiments, a gas cabinet (e.g., FIG. 23) with gas reservoirs can be plugged by a robotic material transfer system into a large number of cartridges, one after the other, as the robotic material transfer system brings them into that module. The gas cabinet includes gas reservoirs for both input gases and output gases. It also includes integrated compressors, gas mixers, filters, and all the gas processing equipment that is necessary to support the cell manufacturing task carried out in that module.

The reservoirs of the liquid and gas cabinets can be replenished (or emptied) from the outside of the modular biological foundry system by a user. In this way, these refill and/or emptying operations do not affect the clean room conditions and the sterility of the modular biological foundry system.

In some embodiments, completing the manufacturing process for a single cellular engineering target requires a rigid cartridge that accommodates the engineering target to go through multiple modules 208. This means that the cellular engineering target can require to be carried in multiple rigid cartridges, one after the other, according to the rigid cartridge configuration needed by the modules that are used to implement the manufacturing process. While a single cellular engineering target might need multiple cartridge, a single rigid cartridge can only be used for a single cellular engineering target. After it has been used for a cellular engineering target, a cartridge must be extracted from the modular biological foundry system and either disposed of or cleaned and sterilized before being ready to be used for another cellular engineering target.

In some embodiments, the modular biological foundry system can be equipped with slots where bins of cartridges (e.g., sealed bins including empty, clean cartridges) can be inserted. In some embodiments, the modular biological foundry system includes slots for bins where the robotic material transfer system deposits used rigid cartridges, such that these used cartridges are then removed with the bin, such as once the bin is full.

In some embodiments, adding bins with new cartridges or removing bins with old cartridges can be done by a manufacturing operator from outside the modular biological foundry system, without affecting the clean-room sterile conditions inside the modular biological foundry system.

In some embodiments, the use of multiple rigid cartridges for a single cellular engineering target determines the need for a module 208 within the modular biological foundry system in which a cellular engineering target is transferred from an interior of one cartridge to an interior of a second cartridge in a sterile and automated manner (e.g., within a closed system of the modular biological foundry system, and with a process that is entirely executed by the robotic material transfer system), hereinafter known as a "cartridge transfer module."

In some embodiments, in the cartridge transfer modules, a liquid cellular engineering target can be moved from one cartridge (e.g., origin cartridge) to another cartridge (e.g., destination cartridge) by simple automatic liquid transfer, such as connectors 1900 and sockets 2000, including, but not limited to, pipettes and syringes, operated by a robotic material transfer system, are able to transfer the liquid cellular engineering target from an output (or sampling) connectors in the origin cartridge, to an input connectors in the destination cartridge. In some embodiments, a limit of pipettes and syringes is that they can only move a limited amount of liquid at a time. Therefore, when using these devices, the liquid transfer process must be repeated several times, until the origin cartridge is empty, and the destination cartridge is full. Since the cartridge transfer module is completely automated, these operations can be executed within the module, without requiring the involvement of the robotic material transfer system (e.g. the articulated handling robot 202).

However, if the volume of liquid to be transferred from the origin cartridge to the destination cartridge is significant, it might take too many iterations to complete the transfer with that have a small volumetric capacity (i.e. pipettes or syringes). In this case, the cartridge transfer process can be completed quickly by establishing a continuous flow of liquid between the two rigid cartridges. When it is necessary to establish a continuous flow of liquid between two rigid cartridges, another embodiment can be implemented in the cartridge transfer module (e.g., FIG. 24). In this approach, a robotic material transfer system places a transfer channel cartridge (which is designed for a one-time use) onto a peristaltic pump instrument. The robotic material transfer system achieves this by grasping the rigid pump socket that holds a flexible channel (e.g., FIG. 24). At the two extremities of the flexible channel there are rigid sockets 2000, which engage the connectors of each rigid cartridge, such as each fluid connector. The robotic material transfer system (e.g., a robotic arm, or a robotic gantry) then engages a socket of the channel with an output connect (from where liquid will be extracted) of the origin cartridge and a second socket of the channel with an input socket (from where liquid will be inserted) of the destination cartridge.

In some embodiments, the electrical connector of the rigid cartridge includes a pressure control mechanism (e.g., valve), a pH sensor, a dissolved oxygen sensor, a temperature sensor, a flow rate sensor, a mass sensor, or a combination thereof.

In some embodiments, the fluidic connector of the rigid cartridge includes a pressure control mechanism, an inlet port, a sampling port, an outlet port, or a combination thereof. In some embodiments, the fluidic connector includes a valve configured to control a flow of a fluid through a corresponding fluidic port.

In some embodiments, a first internal diameter at an upper end portion of a respective connector is less than a second internal diameter at a lower end portion of the respective connector. This allows the robotic material transfer system to engage the connector easily given the defined curvature.

In some embodiments, at least one rigid wall in the plurality of rigid walls further includes a gate mechanism configured to provide access to the fixed internal cavity of the rigid housing. In some embodiments, a length of the gate mechanism is greater than or equal to a cross-sectional area of the soft body bioreactor 1200, which allows for the soft body bioreactor to be received by the interior of the rigid cartridge from at least on orientation of the soft body bioreactor.

In some embodiments, each rigid coupling mechanism protrudes from the substantially upper planar surface of the at least one rigid wall of the rigid housing.

In some embodiments, the rigid cartridge further includes a corresponding cap (e.g., cap 1198) for each respective connector in the plurality of connectors. The corresponding cap encompasses the respective connector, which ensure that the cap is sterile. In some embodiments, the corresponding cap is configured to disengage the connector when a force is applied in a first direction, such as a horizontal direction.

In some embodiments, an exterior surface of the corresponding cap includes a third mating mechanism confirmed to engage a fourth mating mechanism of an articulated handling robot. In some embodiments, the fourth mating mechanism includes a groove or a protrusion around a circumference of the corresponding cap. In some embodiments, the corresponding cap is configured to disengage the respective connector in the plurality of connectors when subject to a lateral force.

In some embodiments, each rigid coupling mechanism of each respective port in the at least one electrical port is a push coupling mechanism.

In some embodiments, the robotic material transfer system then actuates one or more valves of the socket, so that flow is allowed from the origin cartridge to the destination cartridge. In some embodiments, the valve is a one-way valve, in order to regulate the flow according to the requirements of the process. Moreover, in some embodiments, the valve include a filter to reduce the risk of contamination. Once the cartridges are connected and set up by the robotic material transfer system, a continuous and sterile connection is established from the origin cartridge to the destination cartridge. Accordingly, the peristaltic pump can activated and transfer the liquid from the origin cartridge to the destination cartridge. Once the transfer is completed, the robotic material transfer system can close the valves of the socket valves, disengage the sockets from one or more connectors of the rigid cartridge, disposes of the origin cartridge, disposes of the transfer channel cartridge, or a combination thereof. From this, the robotic material transfer system moves the destination cartridge (including the cellular engineering target) into the next module required by a manufacturing process.

In some embodiments, each cartridge, each module and in general each machine in the modular biological foundry system can be equipped with a corresponding barcode that communicate identity information (ID) and/or spatial positioning information (e.g., addresses of FIG. 2A). In some embodiments, multiple cameras or vision systems is disposed on stationary or mobile assemblies (e.g. on the gripper device of the robotic material transfer system, in the modules, on the frame of the modular biological foundry system, etc.). With this video sensors and the corresponding barcode, each cellular engineering target and each step of the process of manufacture of cellular engineering targets are automatically tracked by the robotic material transfer system and/or computer system 100. Therefore, the robotic material transfer system automatically maintains a full, real-time audit trail for each cellular engineering target. Each step in the process, one or more numerical values (or measurements) associated with the manufacturing step (e.g., temperature, concentration, elapsed time, velocity, etc.), and/or a time stamp is automatically logged and communicated via communications network to the computer system 100.

This level of real-time, automatic tracking enables the robotic manufacturing system to guarantee that there is never confusion between multiple cellular engineering targets. This is a significant difference with respect to labor-based systems. Manufacturing processes that rely on human operators can only produce one cellular engineering target at a time in order to avoid mix-ups. The robotic material transfer system described herein can manufacture multiple cellular engineering targets in parallel (at the same time), because each of the cellular engineering targets is completely tracked by the barcode tags and by the vision system of modular biological foundry system. It is also possible to implement the tracking system using radio-frequency tags, magnetic tags or other types of tags that do not rely on video data. In any case, it is the presence of tags and of an automatic cellular engineering target tracking system that ensure the absence of mix-ups and enable the parallel manufacturing of different cell therapy products.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. For instance, the computer program product could contain instructions for operating the user interfaces described with respect to FIG. 2. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A rigid cartridge for housing and removably coupling with a soft body bioreactor, wherein the rigid cartridge comprises:
a plurality of rigid walls defining a fixed interior; wherein the plurality of rigid walls comprises:
a plurality of rigid side walls, wherein at least two adjacent edges in a plurality of edges formed by the plurality rigid side walls comprises a radius of curvature greater than zero, and
a substantially planar upper rigid wall connected to an upper edge portion of each rigid side wall in the plurality of rigid side walls, wherein the substantially planar upper rigid wall comprises:
a plurality of apertures, wherein:
each respective aperture in the plurality of apertures is configured to receive and fixedly engage a corresponding connector which is a member of a group consisting of at least three connectors,
each respective connector in the at least three connectors provides communication with a corresponding port in a plurality of ports of the soft body bioreactor, and
each respective aperture in a first subset of apertures in the plurality of apertures is encompassed by a corresponding annular hood protruding upwardly from the substantially planar upper rigid wall by a first height greater than or equal to a second height of the corresponding connector of the at least three connectors and integrally formed with the substantially planar upper rigid wall, and wherein
the plurality of apertures comprises:
the first subset of apertures, wherein each respective aperture in the first subset of apertures is configured to receive and fixedly engage a fluidic connector of the at least three connectors configured to provide fluidic communication with at least a first port in the plurality of ports of the soft body bioreactor, and
a second subset of apertures, wherein each respective aperture in the second subset of apertures is configured to receive and fixedly engage an electrical connector of the at least three connectors configured to provide electrical communication with at least a second port in the plurality of ports of the soft body bioreactor; and
a seamless lip defined by a lower edge portion of each rigid side wall in the plurality of rigid side walls, and wherein:
each interior surface in a pair of opposing interior surfaces of two rigid side walls in the plurality of rigid side walls comprises a respective first mating mechanism configured to engage a corresponding second mating mechanism of the soft body bioreactor, thereby removably coupling a pair of opposing end portions of the soft body bioreactor with the rigid cartridge.

2. The rigid cartridge of claim 1, wherein the electrical connector comprises a pressure control mechanism, a pH sensor, a dissolved oxygen sensor, a temperature sensor, a flow rate sensor, a mass sensor, or a combination thereof.

3. The rigid cartridge of claim 1, wherein the fluidic connector comprises a pressure control mechanism, an inlet port, a sampling port, an outlet port, or a combination thereof.

4. The rigid cartridge of claim 1, wherein, the fluidic connector comprises a valve configured to control a flow of a fluid through a corresponding fluidic port.

5. The rigid cartridge of claim 1, wherein a first internal diameter at an upper end portion of a respective connector is less than a second internal diameter at a lower end portion of the respective connector.

6. The rigid cartridge of claim 1, wherein at least one rigid wall in the plurality of rigid walls further comprises a gate mechanism configured to provide access to the fixed internal cavity of the rigid housing.

7. The rigid cartridge of claim 6, wherein a length of the gate mechanism is greater than or equal to a cross-sectional area of the soft body bioreactor.

8. The rigid cartridge of claim 6, wherein the gate mechanism is a hinge gate mechanism or a hinge gate mechanism.

9. The rigid cartridge of claim 1, wherein each rigid coupling mechanism protrudes from the substantially upper planar surface of the at least one rigid wall of the rigid housing.

10. The rigid cartridge of claim 9, further comprising a corresponding cap for each respective connector in the plurality of connectors, wherein the corresponding cap encompasses the respective connector.

11. The rigid cartridge of claim 10, wherein an exterior surface of the corresponding cap comprises a third mating mechanism confirmed to engage a fourth mating mechanism of an articulated handling robot.

12. The rigid cartridge of claim 10, wherein the corresponding cap is configured to disengage the respective connector in the plurality of connectors when subject to a lateral force.

13. The rigid cartridge of claim 1, wherein each rigid coupling mechanism of each respective port in the at least one electrical port is a push coupling mechanism.

* * * * *